US006063983A

United States Patent [19]
Georgopoulos

[11] Patent Number: 6,063,983
[45] Date of Patent: *May 16, 2000

[54] MONOCLONAL LYMPHOCYTES AND METHODS OF USE

[75] Inventor: Katia Georgopoulos, Lexington, Mass.

[73] Assignee: The General Hospital Corporation, Boston, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/707,743

[22] Filed: Sep. 4, 1996

Related U.S. Application Data

[60] Provisional application No. 60/003,225, Sep. 5, 1995.

[51] Int. Cl.[7] .............................. C12N 5/00; C12N 15/63; C12N 15/09; A61K 48/00
[52] U.S. Cl. .................................... 800/3; 800/4; 800/18; 800/21; 800/25; 435/375; 435/325; 435/355; 435/372.3; 424/93.1
[58] Field of Search .................................. 800/2, 4, 3, 18, 800/21, 25; 435/375, 325, 6, 172.3, 69.1, 334, 354, 352, 339, 355, 366, 372.3, 373; 935/62, 33, 65; 514/44; 424/93.21, 93.1

[56] References Cited

FOREIGN PATENT DOCUMENTS 0 438 053A1 1/1991 European Pat. Off. .
WO 93/05796 9/1992 WIPO .

OTHER PUBLICATIONS

Winandy et al. Cul 83:289, 1995, May, 27, 1997.
Adams, B. et al. "Pax–5– encodes the transcription factor BSAP and is expressed in B lymphocytes, the developing CNS, and adult testis" *Genes & Development* 6: 1589–1607 (1992).
Akbar, A.N. et al. "A possible role for bcl–2 in regulating T–cell memory—a 'balancing act' between cell death and survival" *Immunology Today* 14(11): 526–531 (1993).
Ardavin, C. et al. "Thymic dendritic cells and T cells develop simultaneously in the thymus from a common precursor population" *Nature* 362; 761–763 (1993).
Asarnow, D.M. et al. "Limited Diversity of γδ Antigen Receptor Genes of Thy–1+ Dendritic Epidermal Cells" *Cell* 55: 837–847 (Dec. 2, 1988).
Beg, A.A. et al. "The IκB proteins: multifunctional regulators of Rel/NF–κB transcription factors" *Genes & Development* 7: 2064–2070 (1993).
Bigby, M. et al. "Ratio of Langerhan Cells to Thy–1+ Dendritic Epidermal Cells in Murine Epidermis Influences the Intensity of Contact Hypersensitivity" *The Journal of Investigative Dermatology* 89(5):495–499 (Nov. 1987).
Boise, L.H. et al. "bcl–x, a bcl–2–Related Gene that Functions as a Dominant Regulator of Apoptotic Cell Death" *Cell* 74: 597–608 (1993).
Bours, V. et al. "The Oncoprotein Bcl–3 Directly Transactivates through κB Motifs via Association with DNA–Binding p50B Homodimers" *Cell* 72: 729–739 (1993).
Cepko, C.L. et al "Construction and Applications of a Highly Transmissible Murine Retrovirus Shuttle Vector" *Cell* 37: 1053–1062 (1984).
Clevers, H.C. et al. "Transcription factors in early T–cell development" *Immunology Today* 14(2): 591–596 (1993).
Connelly, C.S. et al. "The Role of Transgenic Animals in the Analysis of Various Biological Aspects of Normal and Pathologic States" *Experimental Cell Research* 183: 257–276 (1989).
Delwel, R. et al. Four of the Seven Zinc Fingers of the Evi–1 Myeloid–Transforming Gene Are Required for Sequence–Specific Binding to GA(C/T)AAGA(T/C)AAGATAA, *Molecular and Cellular Biology* 13(7): 4291–4300 (1993).
Ehlich, A. et al. "Immunoglobulin Heavy and Light Chain Genes Rearrange Independently at Early Stages of B Cell Development" *Cell* 72: 695–704 (1993).
Fife, A. et al. "Gram negative septicaemia diagnosed on peripheral blood smear appearances" *Journal of Clinical Pathology* 47:82–84 (1994).
Fleming, W.H. et al. "Functional Heterogeneity Is Associated with the Cell Cycle Status of Murine Hematopoietic Stem Cells" *J. Cell Biol.* 122: 897–902 (1993).
Franzoso, G. et al. "The oncoprotein Bcl–3 can facilitate NF–κB–mediated transactivation by removing inhibiting p50 homodimers from select κB sites" *The EMBO Journal*, vol. 12, No. 10 3893–3901 (1993).
Furley, A.J. et al. "Developmentally Regulated Rearrangement and Expression of Genes Encoding the T Cell Receptor–T3 Complex" *Cell*, vol. 46: 75–87 (Jul. 1986).
Garni–Wagner, B.A. et al. "Natural Killer Cells in the Thymus" *The Journal of Immunology* 144(3): 796–803 (1990).
Georgopoulos, K. et al. "Functionally Distinct Isoforms of the CRE–BP DNA–Binding Protein Mediate Activity of a T–Cell–Specific Enhancer" *Molecular and Cellular Biology* 12(2): 747–757 (Feb. 1992).
Georgopoulos, K. et al. "A T cell–specific enhancer is located in a DNase I–hypersensitive area at the 3' end of the CD3–δ gene" *The EMBO Journal* 7(8): 2401–2407 (Aug. 1988).
Godfrey, D.I. and A. Zlotnik "Control points in early T–cell development" *Immunology Today* 14(11): 547–553 (1993).
Gogos, J.A. et al. "Sequence Discrimination by Alternatively Spliced Isoforms of a DNA Binding Zinc Finger Domain" *Science* 257: 1951–1955 (1992).
Hackett, Jr., J. et al. "Origin and Differentiation of Natural Killer Cells" *The Journal of Immunology* 136(8): 3124–3131 (1986).
Hackett, Jr., J. et al. "Transplantable progenitors of natural killer cells are distinct from those of T and B lymphocytes" *Proc. Natl. Acad. Sci USA* 83: 3427–3431 (1986).
Hardy, R.R. et al. "Resolution and Characterization of Pro–B and Pre–Pro–B Cell Stages in Normal Mouse Bone Marrow" *J. Exp. Med.* 173: 1213–1225 (May 1991).

(List continued on next page.)

Primary Examiner—Karen M. Hauda
Attorney, Agent, or Firm—Fish & Richardson P.C.

[57] ABSTRACT

A monoclonal preparation of lymphocytes, their production and use.

86 Claims, 36 Drawing Sheets

OTHER PUBLICATIONS

Havran, W.L. and J.P. Allison. "Developmentally ordered appearance of thymocytes expressing different T–cells antigen receptors" *Nature 335*: 443–445 (1988).

Havran, W.L. and J.P. Allision "Origin of Thy–1 + dendritic epidermal cells of adult mice from fetal thymic precursors" *Nature 344*: 68–70 (1990).

Havran, W.L. et al. "Limited diversity of T–cell receptor γ–chain expression of murine Thy–1 +dendritic epidermal cells revealed by Vγ3–specific monoclonal antibody" *Proc. Natl. Acad. Sci. USA 86*: 4185–4189 (1989).

Haynes, B. et al. "Ontogeny of T–cell precursors: a model for the initial stages of human T–cell development" *Immunology Today 10*(3): 87–90(1989).

Hestdal, K. et al. "Characterization and Regulation of RB6–8C5 Antigen Expression on Murine Bone Marrow Cells" *J. Immunol. 147*(1): 22–28 (Jul. 1, 1991).

Ho, I.–C. et al. "Human GATA–3: a lineage–restricted transcription factor that regulates the expression of the T cell receptor α gene" *The EMBO Journal 10*(5): 1187–1192 (1991).

Ho, I.–C. et al. "Sequence–Specific Binding of Human Ets–1 to the T Cell Receptor α Gene Enhancer" *Science 250*: 814–818 (1990).

Hsu, T. et al. "Multiple Zinc Finger Forms Resulting from Developmentally Regulated Alternative Splicing of a Transcription Factor Gene" *Science 257*: 1946–1950 (1992).

Ikuta, K. et al. "A Developmental Switch in Thymic Lymphocyte Maturation Potential Occurs at the Level of Hematopoietic Stem Cells" *Cell 62*: 863–874 (1990).

Ikuta, K. et al. "Lymphocyte Development From Stem Cells" *Annu. Rev. Immunol. 10*: 759–783 (1992).

Jiang, J. and M. Levine "Binding Affinities and Cooperative Interactions with bHLH Activators Delimit Threshold Responses to the Dorsal Gradient Morphogen" *Cell 72*: 741–752 (1993).

Juhlin, L. and W.B. Shelley "New Staining Techniques for the Langerhans Cell" *Acta Dermatovener 57*: 289–296 (1977).

Kang, S.–M. et al. "NF–κB Subunit Regulation in Nontransformed CD4$^+$T Lymphocytes" *Science 256*: 1452–1456 (1992).

Karasuyama, H. et al. "The Expression of $V_{pre-B}/λ.5$ Surrogate Light Chain in Early Bone Marrow Precursor B Cells of Normal and B Cell–Deficient Mutant Mice" *Cell 77*: 133–143 (Apr. 8, 1994).

Lagasse, E. and I.L. Weissman "BCL–2 Tansgene Inhibits Neutrophils Cell Death But Not Their Engulfment By Microphages" *J. Biochem. 0* (Suppl. 17D): 168 (Mar. 13–31, 1993).

Leiden, J.M. "Transcriptional regulation during T–cell development: The α TCR gene as a molecular model" *Immunology Today 13*(1): (Jan. 22–30, 1992).

Lenardo, M.J. and D. Baltimore "NF–κB: A Pleiotropic Mediator of Inducible and Tissue–Specific Gene Control" *Cell 58*: 227–229 (1989).

Li, E. et al. "Targeted Mutation of the DNA Methyltransferase Gene Results in Embryonic Lethality" *Cell 69*: 915–926 (1992).

Li, Y.–S. et al. "The Regulated Expression of B Lineage Associated Genes during B Cell Differentiation in Bone Marrow and Fetal Liver" *J. Exp. Med. 178*: 951–960 (1993).

Liang, P. et al. "Distribution and cloning of eukaryotic mRNAs by means of differential display: refinements and optimization" *Nucleic Acids Research 21*(14): 3269–3275 (1993).

Mann, R. et al. "Construction of a Retrovirus Packaging Mutant and Its Use to Produce Helper–Free Defective Retrovirus" *Cell 33*: 153–159 (1993).

Martin, D.I.K. et al. "Expression of an erythroid transcription factor in megakaryocytic and mast cell lineages" *Nature 344*: 444–447 (1990).

McDonnell, T.J. and S.J. Korsmeyer "Progression from lymphoid hyperplasia to high–grade malignant lymphoma in mice transgenic for the t(14;18)" *Nature 349*: 254–256 (1991).

McDonnell, T.J. et al. "bcl–2–Immunoglobulin Transgenic Mice Demonstrate Extended B Cell Survival and Follicular Lymphoproliferation" *Cell 57*: 79–88 (1989).

Metcalf, D. "The molecular control of cell division, differentiation commitment and maturation in haemopoietic cells" *Nature 339*:27–30 (1989).

Mombaerts, P. et al. "RAG–1–Deficient Mice Have No Mature B and T Lymphocytes" *Cell 68*: 869–877 (1992).

Mucenski, M.L. et al. "A Functional c–myb Gene is Required for Normal Murine Fetal Hepatic Hematopoiesis" *Cell 65*: 677–689 (1991).

Oltvai, Z.N. et al. "Bcl–2 Heterodimerizes In Vivo with a Conserved Homolog, Bax, That Accelerates Programed Cell Death" *Cell 74*: 609–619 (1993).

Oosterwegel, M. et al. "Cloning of Murine TCF–1, a T Cell–specific Transcription Factor Interacting with Functional Motifs in the CD3–ε and T Cell Receptor α Enhancers" *J. Exp. Med. 173*: 1133–1142 (May 1991).

Oosterwegel, M. et al. "Differential expression of the HMG box factors TCF–1 and LEF–1 during murine embryogenesis" *Development 118*: 439–448 (1993).

Philpott, K.L. et al. "Lymphoid Development in Mice Congenitally Lacking T Cell Receptor αβ–Expressing Cells" *Science 256*: 1448–1452 (Jun. 5, 1992).

Raulet, D.H. et al. "Control of γδ T–Cell Development" *Immunological Reviews 120*:185–204 (1991).

Read, D. and J.L. Manley "Alternatively spliced transcripts of the *Drosophila tramtrack* gene encode zinc finger proteins with distinct DNA binding specificities" *The EMBO Journal 11*(3): 1035–1044 (1992).

Rodewald, H.–R. et al. "A Population of Early Fetal Thymocytes Expressing FcγRII/III Contains Precursors of T Lymphocytes and Natural Killer Cells" *Cell 69*: 139–150 (1992).

Rolink, A. and F. Melchers "Molecular and Cellular Origins of B Lymphocyte Diversity" *Cell 66*: 1061–1094 (1991).

Rudnicki, M.A. et al. "Inactivation of MyoD in Mice Leads to Up–Regulation of the Myogenic HLH Gene Myf–5 and Results in Apparently Normal Muscle Development" *Cell 71*: 383–390 (1992).

Sawyers, C.L. et al. "Leukemia and the Disruption of Normal Hematopoiesis" *Cell 64*: 337–350 (1991).

Sentman, C.L. et al. "bcl–2 Inhibits Multiple Forms of Apoptosis but Not Negative Selection in Thymocytes" *Cell 67*: 879–888 (1991).

Shinkai, Y. et al. "RAG–2–Dificient Mice Lack Mature Lymphocytes Owing to Inability to Initiate V(DJ Rearrangement" *Cell 68*: 855–867 (1992).

Skeath, J.B. et al. "Gene regulation in two dimensions" the proneural achaete and scute genes are controlled by combinations of axis–patterning genes through a common intergenic control region *Genes & Development 6*: 2606–2619 (1992).

Spangrude, G.J. "Enrichment of murine haemopoietic stem cells: diverging roads" *Immunology Today 10*(10): 344–350 (1989).

Spangrude, G.J. et al. "Purification and Characterization of Mouse Hematopoeitic Stem Cells" *Science 241*:58–62 (Jul. 1, 1988).

Spanopoulou, E. et al. "Functional immunoglobulin transgenes guide ordered B–cell differentiation in Rag–1–deficient mice" *Genes & Development 8*: 1030–1042 (1994).

Travis, A. et al. "LEF–1, a gene encoding a lymphoid–specific with protein, an HMG domain, regulates T–cell receptor α enhancer function" *Genes & Development 5*: 880–894 (1991).

Turner, Jr., C.A. et al. "Blimp–1, a Novel Zinc Finger–Containing Protein that Can Drive the Maturation of B Lymphocytes into Immunoglobulin–Secreting Cells" *Cell 77*: 297–306 (Apr. 22, 1994).

van de Wetering, M. et al. "Identification and cloning of TCF–1, a T lymphocyte–specific transcription factor containing a sequence–specific HMG box" *The EMBO Journal 10*(1): 123–132 (1991).

von Boehmer, H. "The Developmental Biology of T Lymphocytes" *Ann. Rev. Immunol. 6*: 309–326 (1988).

Waterman, M.L. et al. "A thymus–specific member of the HMG protein family regulates the human T cell receptor Cα enhancer" *Genes & Development 5*: 656–669 (1991).

Weintraub, H. "The MyoD Family and Myogenesis: Redundancy, Networks, and Thresholds" *Cell 75*: 1241–1244 (Dec. 31, 1993).

Xu, Y. et al. "LH–2: A LIM/homeodomain gene expressed in developing lymphocytes and neural cells" *Proc. Natl. Acad Sci. USA 90*: 227–231 (1993).

Yokoyama, W.M. "Flow Cytometry Analysis Using the Becton Dickinson FACScan" in *Current Protocols in Immunology,* J.E. Coligan et al. (Eds.), Brooklyn, NY: Greene Publishing Associates, 5.4.1–5.4.14 (1992).

Zervos, A.S. et al. "Mxi 1, a Protein that Specifically Interacts with Max to Bind Myc–Max Recognition Sites" *Cell 72*: 223–232 (1993).

Kollman et al., "The concurrent maturation of mouse and human thymocytes in human fetal thymus implanted in NIH–beige–nude–xid mice is associated with the reconstitution of the murine immune system" *J. Exp. Med.* 177:821–832 (1993).

Krowka et al., "Human T cells in the SCID–hu mouse are phenotypically normal and functionally competent", *J. Immunology* 146:3751–3756 (1991).

McCune et al., "The SCID–hu mouse: murine model forthe analysis of human hematolymphoid differentiation and function", *Science* 241:1632–1639 (1988).

Namikawa et al., "Long–term human hematopoiesis in the SCID–hu mouse", *J. Exp. Med.* 172:1055–1063 (1990).

Georgopoulos et al., "Tissue–specific nuclear factors mediate expresion of the CD3–delta gene during T cell development" EMBO Journal 9:109–115 (199).

Georgopoulos et al., "Ikaros, an early lymphoid–specific transcription factor and a putative mediator for T cell commitment" Science 258:808–812 (1992).

Georgopoulos et al., Ikaros an early lymphoid restricted regulatory protein, a putative modulator for T cell specification J. Cellular Biochem. vol. suppl. 17A:B631 (1993).

Singh et al., "Molecular cloning of an enhancer binding protein: isolation by screening of an expression library with a recognition site DNA" Cell 52:415–423 (1988).

Georgopoulos et al., "The Ikaros gene is rquired for the development of all lymphoid lineages" *Cell* 79:143–156 (1994).

Molnar et al., "The Ikaros gene encodes a family of functionally diverse zinc finger DNA–binding proteins" *Mol. Cell. Biol.* 14:8292–8303 (1994).

Winandy et al. "A dominant mutation in the Ikaros gene leads to rapid development 9of leukemia an dlymphoma" *Cell* 83:289–299 (1995).

FIG. 6A

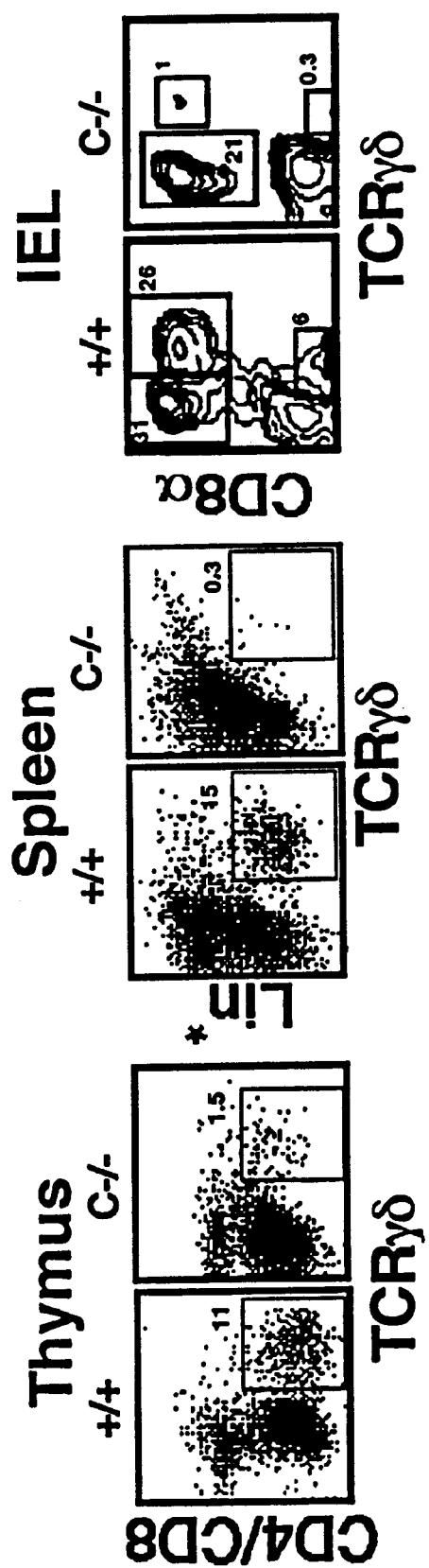

MONOCLONAL LYMPHOCYTES AND METHODS OF USE

This application claims benefit from the previously filed Provisional Application No. 60/003,225, filed Sep. 5, 1995, which is hereby incorporated by reference.

This invention was made with government support from the National Institute of Health. Accordingly, the government retains certain rights in the invention.

BACKGROUND OF THE INVENTION

The invention relates to preparations, preferably monoclonal preparations, of lymphocytes, their production and use.

SUMMARY OF THE INVENTION

In general, the invention features, a method of providing a proliferation-deregulated cell, e.g., a hematopoietic cell, e.g., stem cell, e.g., a totipotent or a pluripotent stem cell, or a descendent of a stem cell, e.g., a lymphocyte, e.g., a transformed lymphocyte. The method includes: providing a mammal having an Ikaros-deregulated cell, e.g., a hematopoietic cell, e.g., stem cell, e.g., a totipotent or a pluripotent stem cell, or a descendent of a stem cell, e.g., a lymphocyte; and isolating a proliferation-deregulated cell, e.g., a hematopoietic cell, e.g., stem cell, e.g., a totipotent or a pluripotent stem cell, or a descendent of a stem cell, e.g., a lymphocyte, e.g., a transformed lymphocyte from the mammal.

In preferred embodiments: the mammal is a non-human mammal, e.g., a swine, a nonhuman primate, e.g., a monkey, a goat, or a rodent, e.g., a rat or a mouse.

In a preferred embodiment, the method further includes: allowing the Ikaros-deregulated cell to divide and give rise to a proliferation-deregulated cell, e.g., a transformed lymphocyte; providing a plurality of the proliferation-deregulated cells e.g., lymphocytes or transformed lymphocytes from the mammal.

In preferred embodiments: the proliferation-deregulated cell e.g., a lymphocyte, e.g., a transformed lymphocyte, is isolated from a lymphoma of the mammal.

In preferred embodiments: the mammal is heterozygous at the Ikaros locus; the mammal carries a mutation at the Ikaros gene, e.g., a point mutation in or a deletion for all or part of the Ikaros gene, e.g., a mutation in the DNA binding region, e.g., a point mutation in, or a deletion for all or part of one or more of F1, F2, F3, or F4; the mammal is heterozygous or homozygous for an Ikaros transgene, e.g., a transgene having, e.g., a mutation in the DNA binding region, e.g., a point mutation in, or a deletion for all or part of one or more of F1, F2, F3, or F4; the mammal carries a mutation in the control region of the Ikaros gene which results in the preferential expression of PPID subunits as opposed to NPID subunits.

In preferred embodiments: the mammal carries a mutation at the Ikaros gene, e.g., a point mutation or a deletion, which, inactivates one or both of transcriptional activation or dimerization, which decreases the half life of the protein, or which inactivates one or both of the C terminal Zinc finger domains; the mammal carries a C terminal deletion.

In preferred embodiments: the proliferation-deregulated cell is a homozygous mutant Ikaros cell e.g., a lymphocyte; the proliferation-deregulated lymphocyte is a T lymphocyte, e.g., a CD4+CD8−, CD8+CD4−, CD4+CD8+, or CD4−CD8− lymphocyte; the proliferation-deregulated cell is heterozygous or homozygous for an Ikaros transgene.

In preferred embodiments, the cell is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments: the mammal is immunized with an antigen; the cell is exogenously supplied and one or both of the mammal or the mammal which donates the cell are immunized with an antigen. The antigen can be: an alloantigen; a xenoantigen; an autoantigen; a protein; or an antigen which gives rise to an anti-idiotypic lymphocyte.

In a preferred embodiment: the Ikaros-deregulated cell, e.g., a lymphocyte, is supplied exogenously to the mammal, e.g., to a homozygous wild-type Ikaros mammal or a mammal carrying a mutation at the Ikaros gene, e.g., a point mutation or a deletion for all or part of the Ikaros gene. If exogenously supplied, the cell can be a human or a nonhuman, e.g., a swine, nonhuman primate, e.g., a monkey, a goat, or a rodent, e.g., a rat or a mouse, lymphocyte.

In another aspect, the invention features, a method of providing a clonal population of cells, e.g., a hematopoietic cells, e.g. g., a stem cells, e.g., totipotent or a pluripotent stem cells, or descendants of a stem cell, e.g., a lymphocytes. The method includes: providing a mammal having an Ikaros-deregulated cell, e.g., a lymphocyte; isolating one or more cells, e.g., lymphocytes, from the mammal, provided that if one cell is isolated, the cell is allowed to proliferate into a clonal population of cells lymphocytes.

In preferred embodiments: the mammal is a non-human mammal, e.g., a swine, a nonhuman primate, e.g., a monkey, a goat, or a rodent, e.g., a rat or a mouse.

In a preferred embodiment: the clonal population of cells is isolated from a lymphoma of the mammal.

In preferred embodiments: the mammal is an Ikaros-deregulated animal; the mammal is heterozygous at the Ikaros locus; the mammal carries a mutation at the Ikaros gene, e.g., a point mutation in or a deletion for all or part of the Ikaros gene, e.g., a mutation in the DNA binding region, e.g., a point mutation in, or a deletion for all or part of one or more of F1, F2, F3, or F4; the mammal is heterozygous or homozygous for an Ikaros transgene, e.g., a transgene having, e.g., a mutation in the DNA binding region, e.g., a point mutation in, or a deletion for all or part of one or more of F1, F2, F3, or F4; the mammal carries a mutation in the control region of the Ikaros gene which results in the preferential expression of PPID subunits as opposed to NPID subunits.

In preferred embodiments: the mammal carries a mutation at the Ikaros gene, e.g., a point mutation or a deletion, which, inactivates one or both of transcriptional activation or dimerization, which decreases the half life of the protein, or which inactivates one or both of the C terminal Zinc finger domains; the mammal carries a C terminal deletion.

In a preferred embodiment: the clonal population is heterozygous or homozygous for an Ikaros transgene; the clonal population consists of heterozygous Ikaros cells; the clonal population includes or consists of homozygous mutant Ikaros cells; the clonal population includes or consists of heterozygous and homozygous mutant Ikaros cells, e.g., lymphocytes; the clonal population of lymphocytes includes or consists of T lymphocytes, e.g., of CD4+CD8−, CD8+CD4−, CD4+CD8+, or CD4−CD8− lymphocytes.

In preferred embodiments, the cells is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments: the mammal is immunized with an antigen; the lymphocyte is exogenously supplied and one or both of the mammal or the mammal which donates the lymphocyte are immunized with an antigen. The antigen can be: an alloantigen; a xenoantigen or an autoantigen; a protein; or an antigen which gives rise to an anti-idiotypic lymphocyte.

In a preferred embodiment: the Ikaros-deregulated cell e.g., a lymphocyte is supplied exogenously to the mammal, e.g., a homozygous wild-type Ikaros mammal or a mammal carrying a mutation at the Ikaros gene, e.g., a point mutation or a deletion for all or part of the Ikaros gene. If exogenously supplied, the cell can be a human or a nonhuman, e.g., a swine, a nonhuman primate, e.g., a monkey, a goat, or a rodent, e.g., a rat or a mouse, lymphocyte.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of providing a lymphocyte, or a substantially homogenous population of lymphocytes, which recognize a selected antigen. The method includes: providing a mammal having an Ikaros-deregulated lymphocyte; isolating one or more lymphocytes from the mammal.

In preferred embodiments: the mammal is a non-human mammal, e.g., a swine, a nonhuman primate, e.g., a monkey, a goat, or a rodent, e.g., a rat or a mouse.

In preferred embodiments: the lymphocyte or the substantially homogenous population of lymphocytes is isolated from a lymphoma of the mammal.

In another preferred embodiment: the mammal is an Ikaros-deregulated animal; the mammal is heterozygous at the Ikaros locus; the mammal carries a mutation at the Ikaros gene, e.g., a point mutation in or a deletion for all or part of the Ikaros gene, e.g., a mutation in the DNA binding region, e.g., a point mutation in, or a deletion for all or part of one or more of F1, F2, F3, or F4; the mammal is heterozygous or homozygous for an Ikaros transgene, e.g., a transgene having, e.g., a mutation in the DNA binding region, e.g., a point mutation in, or a deletion for all or part of one or more of F1, F2, F3, or F4; the mammal carries a mutation in the control region of the Ikaros gene which results in the preferential expression of PPID subunits as opposed to NPID subunits.

In preferred embodiments: the mammal carries a mutation at the Ikaros gene, e.g., a point mutation or a deletion, which, inactivates one or both of transcriptional activation or dimerization, which decreases the half life of the protein, or which inactivates one or both of the C terminal Zinc finger domains; the mammal carries a C terminal deletion.

In a preferred embodiment: the lymphocyte is, or the substantially homogenous population of lymphocytes includes a heterozygous or homozygous lymphocyte for an Ikaros transgene; the lymphocyte is, or the substantially homogenous population of lymphocytes includes a heterozygous Ikaros lymphocytes; the lymphocyte is, or the substantially homogenous population of lymphocytes includes a homozygous mutant Ikaros lymphocytes; the substantially homogenous population of lymphocytes includes a mixture of heterozygous Ikaros lymphocytes and homozygous mutant Ikaros lymphocytes; the lymphocyte is, or the substantially homogenous population of lymphocytes includes T lymphocytes, e.g., of CD4+CD8−, CD8+CD4− or CD4+CD8+ lymphocytes.

In preferred embodiments, the lymphocyte is: a helper T cell; cytolytic T cell; a suppressor T cell; a T cell which secretes one or more anti-inflammatory cytokines, e.g., IL4, IL-10, or IL-13; a T cell which is antigen or idiotype specific; a suppressor T cell which is anti-idiotypic for an auto antibody or for an antibody which recognizes an allograft or xenograft tissue.

In a preferred embodiment: the Ikaros-deregulated lymphocyte is supplied exogenously to the mammal, e.g., a homozygous wild-type Ikaros mammal or a mammal carrying a mutation at the Ikaros gene. If exogenously supplied, the lymphocyte can be a human or a nonhuman, e.g., a swine, a monkey, a goat, or a rodent, e.g., a rat or a mouse, lymphocyte.

In preferred embodiments: the mammal is immunized with an antigen; the lymphocyte is exogenously supplied and one or both of the mammal, or the mammal which donates the lymphocyte, are immunized with an antigen. The antigen can be: an alloantigen; a xenoantigen or an autoantigen; a protein; or an antigen which gives rise to an anti-idiotypic lymphocyte.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a proliferation-deregulated cell, e.g., a hematopoietic cell, e.g., a stem cell, e.g., a totipotent or a pluripotent stem cell, or a descendent of a stem cell, e.g., a lymphocyte, or an Ikaros-deregulated cell, e.g., a hematopoietic cell, e.g., a stem cell, e.g., a totipotent or a pluripotent stem cell, or a descendent of a stem cell, e.g., a lymphocyte, or a population, or substantially purified preparation, of such cells, produced, preferably, by a method of the invention.

In another aspect, the invention features, cell, e.g., a hematopoietic cell, e.g., a stem cell, e.g., a totipotent or a pluripotent stem cell, or a descendent of a stem cell, e.g., a lymphocyte, or, a clonal population, or substantially purified preparation, of cells produced, preferably, by a method of the invention described herein. Preferably, the cells are proliferation-deregulated or Ikaros-deregulated cells.

In another aspect, the invention features, a lymphocyte or, a substantially homogenous population, or substantially purified preparation, of lymphocytes produced, preferably, by a method of the invention described herein which lymphocytes or population recognize a selected antigen. Preferably, the lymphocytes are proliferation-deregulated or Ikaros-deregulated lymphocyte, e.g., transformed.

In another aspect, the invention features, a method of culturing a proliferation- or Ikaros-deregulated cell, e.g., a hematopoietic cell, e.g., a stem cell, e.g., a totipotent or a pluripotent stem cell, or a descendent of a stem cell, e.g., a lymphocyte, e.g., a cell having at least one mutant allele at the Ikaros locus. The method includes: introducing the cell into a mammal, wherein, preferably, the mammal is other than the one from which the cell has been isolated originally; and culturing the cell.

In a preferred embodiment, the method further includes: allowing the cell to proliferate in the mammal.

In preferred embodiments: the mammal is heterozygous at the Ikaros locus; the mammal carries a mutation at the Ikaros gene; the mammal is a homozygous wild-type Ikaros mammal; the mammal is a non-human mammal, e.g., a swine, a nonhuman primate, e.g., a monkey, a goat, or a rodent, e.g., a rat or a mouse, or an immunocompromised mouse or a nude mouse.

In another preferred embodiment: the donor is Ikaros-deregulated; the donor of the cell is heterozygous or homozygous for an Ikaros transgene, e.g., a transgene having, e.g., a mutation in the DNA binding region, e.g., a point mutation in, or a deletion for all or part of one or more of F1, F2, F3, or F4; the donor of the cell is heterozygous at the Ikaros locus; the donor of the cell carries a mutation at the Ikaros gene, e.g., a mutation in the DNA binding region, e.g., a point mutation in or a deletion for all or part of the Ikaros gene, e.g., a point mutation in, or a deletion for all or part of one or more of F1, F2, F3, or F4; the donor carries a mutation in the control region of the Ikaros gene which results in the preferential expression of PPID subunits as opposed to NPID subunits the donor of the cell is a homozygous wild-type Ikaros mammal; the donor of the cell is a human or non-human mammal, e.g., a swine, a monkey, a goat, or a rodent, e.g., a rat or a mouse. In the case of an Ikaros wild-type donor, e.g., a human donor, the Ikaros lesion can be made in vitro.

In preferred embodiments: the donor of the cells carries a mutation at the Ikaros gene, e.g., a point mutation or a deletion, which, inactivates one or both of transcriptional activation or dimerization, which decreases the half life of the protein, or which inactivates one or both of the C terminal Zinc finger domains; the donor of the cells carries a C terminal deletion.

In a preferred embodiment: the cell is heterozygous or homozygous for an Ikaros transgene; the cell is a heterozygous Ikaros cell; the lymphocyte is a homozygous mutant Ikaros lymphocyte; the lymphocytes is a T lymphocyte, e.g., a CD4+CD8−, CD8+CD4−, CD4+CD8+, or CD4−CD8− lymphocyte.

In preferred embodiments, the cell is a lymphocyte and is: a helper T cell; cytolytic T cell; a suppressor T cell; a T cell which secretes one or more anti-inflammatory cytokines, e.g., IL4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of culturing a proliferation- or Ikaros-deregulated cell, e.g., a hematopoietic cell, e.g., a stem cell, e.g., a totipotent or a pluripotent stem cell, or a descendent of a stem cell, e.g., a lymphocyte, e.g., a lymphocyte or other cell having at least one mutant allele at the Ikaros locus. The method includes: culturing the cell, in vivo or in vitro, in the presence of a cytokine, e.g., IL-2, preferably an exogenously administered cytokine.

In preferred embodiments: the donor of the cell is heterozygous or homozygous for an Ikaros transgene, e.g., a transgene having, e.g., a mutation in the DNA binding region, e.g., a point mutation in, or a deletion for all or part of one or more of F1, F2, F3, or F4; the donor of the cell is heterozygous at the Ikaros locus; the donor of the cell carries a mutation at the Ikaros gene, e.g., a point mutation in or a deletion for all or part of the Ikaros gene, e.g., a mutation in the DNA binding region, e.g., a point mutation in, or a deletion for all or part of one or more of F1, F2, F3, or F4; the donor of the cell carries a mutation in the control region of the Ikaros gene which results in the preferential expression of PPID subunits as opposed to NPID subunits; the donor of the lymphocyte is a homozygous wild-type Ikaros mammal; the mammal is a human or non-human mammal, e.g., a swine, a monkey, a goat, or a rodent, e.g., a rat or a mouse. In the case of an Ikaros wild-type donor, e.g., a human donor, the Ikaros lesion can be made in vitro.

In preferred embodiments: the donor of the cell carries a mutation at the Ikaros gene, e.g., a point mutation or a deletion, which, inactivates one or both of transcriptional activation or dimerization, which decreases the half life of the protein, or which inactivates one or both of the C terminal Zinc finger domains; the donor of the cell carries a C terminal deletion.

In another preferred embodiment: the cell is heterozygous or homozygous for an Ikaros transgene; the cell is a heterozygous Ikaros cell; the cell is a homozygous mutant Ikaros cell; the lymphocytes is a T lymphocyte, e.g., a CD4+CD8−, CD8+CD4−, CD4+CD8+, or CD4−CD8− lymphocyte.

In preferred embodiments, the cell is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of modulating the activity of a target tissue or cell, e.g., a target lymphocyte. The method includes: supplying the target; and exposing the target to a proliferation- or Ikaros-deregulated cell, e.g., a hematopoietic cell, e.g., a stem cell, e.g., a totipotent or a pluripotent stem cell, or a descendent of a stem cell, e.g., a lymphocyte, e.g., a lymphocyte having at least one mutant allele at the Ikaros locus, preferably provided that: the target is not Ikaros-deregulated; the target and the cell differ in genotype at a locus other than the Ikaros locus; the target and the cell are from different animals; the target and the cell are from different species; the target activity is modulated in a recipient mammal and either the target or the cell is from a donor mammal other than the recipient mammal; or the target is exposed to the cell in an in vitro system.

In a preferred embodiment: the donor of the Ikaros-deregulated cell is heterozygous or homozygous for an Ikaros transgene; the donor of the Ikaros-deregulated cell is heterozygous at the Ikaros locus; the donor of the Ikaros-deregulated cell carries a point mutation in or a deletion for all or part of the Ikaros gene, e.g., mutation in the DNA binding region, e.g., a point mutation in, or a deletion for all or part of one or more of F1, F2, F3, or F4; the donor carries a mutation in the control region of the Ikaros gene which results in the preferential expression of PPID subunits as opposed to NPID subunits; the donor of the Ikaros-deregulated cell is human or a non-human mammal, e.g., a swine, a monkey, a goat, or a rodent, e.g., a rat or a mouse. In preferred embodiments, e.g., in the case of the human donor, the manipulation that gives rise to Ikaros deregulation, e.g., an Ikaros lesion, can be made in vitro.

In preferred embodiments: the donor of the Ikaros-deregulated cell carries a mutation at the Ikaros gene, e.g., a point mutation or a deletion, which, inactivates one or both of transcriptional activation or dimerization, which decreases the half life of the protein, or which inactivates one or both of the C terminal Zinc finger domains; the donor of the Ikaros-deregulated cell carries a C terminal deletion.

In another preferred embodiment: the cell is heterozygous or homozygous for an Ikaros transgene; the cell is a heterozygous Ikaros cell; the cell is a homozygous mutant Ikaros cell; the lymphocyte is a T lymphocyte, e.g., a CD4+CD8−, CD8+CD4−, CD4+CD8+ or CD4−CD8− lymphocyte.

In preferred embodiments, the cell is a lymphocyte and is: a helper T cell; cytolytic T cell; a suppressor T cell; a T cell which secretes one or more anti-inflammatory cytokines, e.g., IL-4, IL-10, or IL- 13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In a preferred embodiment: the method is performed in an in vitro system; the method is performed in vivo, e.g., in a mammal, e.g., a rodent, e.g., a mouse or a rat, or a primate, e.g., a non-human primate or a human. If the method is performed in vitro, the donor of the target cell or tissue and the lymphocyte can be same or different. If the method is performed in vivo, there is a recipient animal and one or more donors.

In preferred embodiments: the method is performed in vivo and one or more of the recipient, the donor of the target cell or tissue, the donor of the cell, is immunized with an antigen; the method is performed in vitro and one or more of the donor of the target cell or tissue, the donor of the cell is immunized with an antigen. The antigen can be: an alloantigen; a xenoantigen or an autoantigen; a protein; or an antigen which gives rise to an anti-idiotypic lymphocyte.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, bone marrow tissue, lymph node tissue or thymic tissue.

In another preferred embodiment, the target is from a mammal, e.g., a human; the mammal is a non-human mammal, e.g., a swine, a monkey, a goat, or a rodent, e.g., a rat or a mouse.

In preferred embodiments, the activity of the target which is modulated is: the production of a cytokine; the proliferation or activation of a cell of the immune system; the production of an antibody; the lysis of an antigen presenting cell or the activation of a cytolytic T lymphocyte; the effect of target on resistance to infection; the effect of target on life span; the effect of target on body weight; the effect of target on the presence, function, or morphology of tissues or organs of the immune system; the effect of target on the ability of a component of the immune system to respond to a stimulus (e.g., a diffusable substance, e.g., cytokines, other cells of the immune system, or antigens); the effect of target on the ability to exhibit immunological tolerance to an alloantigen or a xenoantigen.

In preferred embodiments: the target and the cell differ in genotype at a locus other than the Ikaros locus; the target and the cell are from different animals; the target is not Ikaros-deregulated.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of evaluating the effect of a treatment on the ability of a cell, e.g., a hematopoietic cell, e.g., a stem cell, e.g., a totipotent or a pluripotent stem cell, or a descendent of a stem cell, e.g., a lymphocyte, to modulate the activity of a target tissue or cell, e.g., a target lymphocyte. The method includes: forming a reaction mixture which includes a proliferation- or Ikaros-deregulated cell, e.g., a hematopoietic cell, e.g., a stem cell, e.g., a totipotent or a pluripotent stem cell, or a descendent of a stem cell, e.g., a lymphocyte, e.g., a lymphocyte having at least one mutant allele at the Ikaros locus, and a target; administering the treatment; and determining the effect of the treatment on a parameter related to the ability of the lymphocyte to modulate the activity of the target.

In a preferred embodiment: the target and the cell differ in genotype at a locus other than the Ikaros locus; the target and the cell are from different animals; the target and the cell are from different species; the target activity is modulated in a recipient mammal and either the target or the cell is from a donor mammal other than the recipient mammal; or the target is exposed to the cell in an in vitro system; the target is not Ikaros-deregulated.

In a preferred embodiment: the donor is Ikaros-deregulated; the donor of the proliferation- or Ikaros-deregulated cell is heterozygous or homoygous for an Ikaros transgene; the donor of the proliferation- or Ikaros-deregulated cell is heterozygous at the Ikaros locus; the donor of the proliferation- or Ikaros-deregulated cell carries a point mutation in or a deletion for all or part of the Ikaros gene, e.g., a mutation in the DNA binding region, e.g., a point mutation in, or a deletion for all or part of one or more of F1, F2, F3, or F4; ; the donor carries a mutation in the control region of the Ikaros gene which results in the preferential expression of PPID subunits as opposed to NPID subunits; the donor of the proliferation- or Ikaros-deregulated lymphocyte is a human or non-human mammal, e.g., a swine, a monkey, a goat, or a rodent, e.g., a rat or a mouse. In preferred embodiments, e.g., in the case of a wild-type donor, e.g., a human donor, the manipulation that gives rise to Ikaros deregulation, e.g., an Ikaros lesion, can be made in vitro.

In preferred embodiments: the donor of the proliferation- or Ikaros-deregulated cell carries a mutation at the Ikaros gene, e.g., a point mutation or a deletion, which, inactivates one or both of transcriptional activation or dimerization, which decreases the half life of the protein, or which inactivates one or both of the C terminal Zinc finger domains; the donor of the proliferation- or Ikaros-deregulated cell carries a C terminal deletion.

In another preferred embodiment: the cell is heterozygous or homozygous for an Ikaros transgene, e.g., a transgene having, e.g., a point mutation in, or a deletion for all or part of one or more of F1, F2, F3, or F4; the lymphocyte is a heterozygous Ikaros cell; the cell is a homozygous mutant Ikaros cell; the lymphocyte is a T lymphocyte, e.g., a CD4+CD8−, CD8+CD4−, CD4+CD8+ or CD4−CD8− lymphocyte.

In preferred embodiments, the cell is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In a preferred embodiment: the method is performed in an in vitro system; the method is performed in vivo, e.g., in a mammal, e.g., a rodent, e.g., a mouse or a rat, or a primate, e.g., a non-human primate or a human. If the method is performed in vivo, there is a recipient animal and one or more donors. The recipient can differ in species or genotype, or be from a different animal, from one or both (if there are two), donors. The donors, if there are two, can differ by genotype or species, or can be from different animals.

In preferred embodiments: the method is performed in vivo, and one or more of the recipient, the donor of the target cell or tissue, the donor of the cell, is immunized with an antigen; the method is performed in vitro, and one or both of the donor of the target cell or tissue, the donor of the cell is immunized with an antigen. The antigen can be: an alloantigen; a xenoantigen or an autoantigen; a protein; or an antigen which gives rise to an anti-idiotypic lymphocyte.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, bone marrow tissue, lymph node tissue or thymic tissue.

In another preferred embodiment, the target is from a mammal, e.g., a human; the mammal is a non-human mammal, e.g., a swine, a monkey, a goat, or a rodent, e.g., a rat or a mouse.

In preferred embodiments the treatment can include: the administration of a drug, chemical, or other substance; the administration of ionizing radiation; the administration of an antibody, e.g., an antibody directed against a molecule or cell of the immune system; administration of a substance or other treatment which suppresses the immune system; or administration of a substance or other treatment which promotes or activates, or which inhibits, the function of the immune system; introduction of a nucleic acid, e.g., a nucleic acid which encodes or expresses a gene product, e.g., a component of the immune system; the introduction of a protein, e.g., a protein which is a component of the immune system.

In preferred embodiments, the parameter related to the ability of a cell to modulate the activity of a target is any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to exhibit immunological tolerance to an alloantigen or a xenoantigen.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of evaluating the effect of cell-, e.g., a hematopoietic cell-, e.g., a stem cell-, e.g., a totipotent or a pluripotent stem cell-, or a descendent of a stem cell-, e.g., a lymphocyte-function on an immune response in a mammal. The method includes: supplying the function by supplying (preferably exogenously) an Ikaros-deregulated hematopoietic cell, e.g., a lymphocyte having at least one mutant allele at the Ikaros locus to the mammal; and evaluating the effect of the hematopoietic cell function on a parameter related to the immune response in the mammal.

In preferred embodiments: the mammal is heterozygous at the Ikaros locus; the mammal carries a mutation at the Ikaros gene, e.g., a mutation in the DNA binding region, e.g., a point mutation, or a deletion for all or part of one or more of F1, F2, F3, or F4; the mammal carries a mutation in the control region of the Ikaros gene which results in the preferential expression of PPID subunits as opposed to NPID subunits; the mammal is a homozygous wild-type Ikaros mammal; the mammal is a non-human mammal, e.g., a swine, a nonhuman primate, e.g., a monkey, a goat, or a rodent, e.g., a rat or a mouse, or an immunocompromised mouse or a nude mouse; the mammal is heterozygous or homozygous for an Ikaros transgene.

In preferred embodiments: the donor is Ikaros-deregulated; the donor of the hematopoietic cell is homozygous or heterozygous for an Ikaros transgene, e.g., a transgene having, e.g., a mutation in the DNA binding region, e.g., a point mutation in, or a deletion for all or part of one or more of F1, F2, F3, or F4; the donor of the hematopoietic cell is heterozygous at the Ikaros locus; the donor of the hematopoietic cell carries a mutation at the Ikaros gene, e.g., a point mutation in or a deletion for all or part of the Ikaros gene, e.g., a mutation in the DNA binding region, e.g., a point mutation in, or a deletion for all or part of one or more of F1, F2, F3, or F4; the donor of the hematopoietic cell is a homozygous wild-type Ikaros mammal; the donor carries a mutation in the control region of the Ikaros gene which results in the preferential expression of PPID subunits as opposed to NPID subunits; the donor of the hematopoietic cell is a human or non-human mammal, e.g., a swine, a monkey, a goat, or a rodent, e.g., a rat or a mouse. In preferred embodiments, e.g., in the case of an Ikaros wild-type donor, e.g., a human donor, the manipulation that gives rise to Ikaros deregulation, e.g., an Ikaros lesion, can be made in vitro.

In preferred embodiments: the donor of the hematopoietic cell is homozygous or heterozygous for a mutation at the Ikaros gene, e.g., a point mutation or a deletion, which, inactivates one or both of transcriptional activation or dimerization, which decreases the half life of the protein, or which inactivates one or both of the C terminal Zinc finger domains; the donor of the hematopoietic cell is homozygous or heterozygous for a C terminal deletion.

In a preferred embodiment: a cell of an immune system component which exhibits the immune response and the hematopoietic cell differ in genotype at a locus other than the Ikaros locus; a cell of an immune system component which exhibits the immune response and the hematopoietic cell are from different animals; or a cell of an immune system component which exhibits the immune response and the hematopoietic cell are from different species.

In another preferred embodiment: the hematopoietic cell is heterozygous or homozygous for an Ikaros transgene, e.g., a transgene having, in the DNA binding region, e.g., a point mutation in, or a deletion for all or part of one or more of F1, F2, F3, or F4; the hematopoietic cell is a heterozygous Ikaros hematopoietic cell; the hematopoietic cell is a homozygous mutant Ikaros hematopoietic cell; the lymphocyte is a T lymphocyte, e.g., a CD4+CD8−, CD8+CD4−, CD4+CD8+ or CD4−CD8− lymphocyte.

In preferred embodiments: the hematopoietic cell is heterozygous or homozygous for a mutation at the Ikaros gene, e.g., a point mutation or a deletion, which, inactivates one or both of transcriptional activation or dimerization, which decreases the half life of the protein, or which inactivates one or both of the C terminal Zinc finger domains; the hematopoietic cell is heterozygous or homozygous for a C terminal deletion.

In preferred embodiments, the hematopoietic cell is a lymphocytre and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments: the method is performed in vivo, and one or more of the recipient mammal, the donor of the hematopoietic cell, is immunized with an antigen. The antigen can be: an alloantigen; a xenoantigen or an autoantigen; a protein; or an antigen which gives rise to an anti-idiotypic lymphocyte.

In a preferred embodiment: the parameter related to the immune response can be any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In preferred embodiments: the mammal is a nonhuman primate, e.g., a monkey, a swine, a goat, or a rodent, e.g., a mouse or rat; the mammal is wild-type; the mammal is an animal model for a human disease, e.g., a NOD mouse; the mammal is immunocompromised by irradiation, chemotherapy or genetic defect, e.g., it is a SCID mouse or a nude mouse.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of evaluating the effect of a cell-, e.g., a hematopoietic cell-, e.g., a stem cell-, e.g., a totipotent or a pluripotent stem cell-, or a descendent of a stem cell-, e.g., a lymphocyte-function, on an immune response in an in vitro system. The method includes: supplying the function by supplying an Ikaros-deregulated hematopoietic cell e.g., a lymphocyte, e.g., a lymphocyte having at least one mutant allele at the Ikaros locus, to the in vitro system; and evaluating the effect of the hematopoietic cell function on a parameter related to immune response in the in vitro system.

In another preferred embodiment: the donor is Ikaros-deregulated; the donor of the hematopoietic cell is heterozygous or homozygous for an Ikaros transgene, e.g., a transgene having, e.g., a mutation in the DNA binding region, e.g., a point mutation in, or a deletion for all or part of one or more of F1, F2, F3, or F4; the donor of the hematopoietic cell is heterozygous at the Ikaros locus; the donor of the hematopoietic cell carries a mutation at the Ikaros gene, e.g., a point mutation in or a deletion for all or part of the Ikaros gene, e.g., a mutation in the DNA binding region, e.g., a point mutation in, or a deletion for all or part of one or more of F1, F2, F3, or F4; the donor of the hematopoietic cell is a homozygous wild-type Ikaros mammal; the donor carries a mutation in the control region of the Ikaros gene which results in the preferential expression of PPID subunits as opposed to NPID subunits; the donor of the hematopoietic cell is a human or non-human mammal, e.g., a swine, a monkey, a goat, or a rodent, e.g., a rat or a mouse. In preferred embodiments, e.g., in the case of an Ikaros wild-type donor, e.g., a human donor, the manipulation that gives rise to Ikaros deregulation, e.g., an Ikaros lesion, can be made in vitro.

In preferred embodiments: the donor of the hematopoietic cell is heterozygous or homozygous for a mutation at the Ikaros gene, e.g., a point mutation or a deletion, which, inactivates one or both of transcriptional activation or dimerization, which decreases the half life of the protein, or which inactivates one or both of the C terminal Zinc finger domains; the donor of the hematopoietic cell is heterozygous or homozygous for a C terminal deletion.

In a preferred embodiment: a cell of an immune system component which exhibits the immune response and the hematopoietic cell differ at a locus other than the Ikaros locus; a cell of an immune system component which exhibits the immune response and the hematopoietic cell are from different animals; or a cell of an immune system component which exhibits the immune response and the hematopoietic cell are from different species.

In another preferred embodiment: the hematopoietic cell is heterozygous or homozygous for an Ikaros transgene, e.g., a transgene having, e.g., a point mutation in, or a deletion for all or part of one or more of F1, F2, F3, or F4; the hematopoietic cell is a heterozygous Ikaros hematopoietic cell; the hematopoietic cell is a homozygous mutant Ikaros hematopoietic cell; the lymphocyte is a T lymphocyte, e.g., a CD4+CD8−, CD8+CD4−, CD4+CD8+ or CD4−CD8− lymphocyte.

In preferred embodiments: the hematopoietic cell is heterozygous or homozygous for an Ikaros transgene, e.g., a transgene having a point mutation or a deletion, which, inactivates one or both of transcriptional activation or dimerization, which decreases the half life of the protein, or which inactivates one or both of the C terminal Zinc finger domains; the hematopoietic cell is heterozygous or homozygous for an Ikaros transgene, e.g., a transgene having a C terminal deletion.

In preferred embodiments, the hematopoietic cell is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments: the donor of the mutant Ikaros hematopoietic cell or the donor of the immune system component or both are immunized with an antigen. The antigen can be: an alloantigen; a xenoantigen or an autoantigen; a protein; or an antigen which gives rise to an anti-idiotypic lymphocyte.

In a preferred embodiment the parameter related to the immune response can be any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diff-usable substance, e.g., cytokines, other cells of the immune system, or antigens); the ability to present an antigen; the ability to exhibit immunological tolerance to an alloantigen or a xenoantigen.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of modulating, e.g., promoting or inhibiting, an immune response of a subject, e.g., a subject mammal, e.g., a primate, e.g., a human or nonhuman primate, e.g., a swine, a nonhuman primate, e.g., a monkey, a goat, or a rodent, e.g., a rat or a mouse. The method includes: introducing into the subject an Ikaros-deregulated cell, e.g., a hematopoietic cell, e.g., a stem cell, e.g., a totipotent or a pluripotent stem cell, or a descendent of a stem cell, e.g., a lymphocyte, e.g., a lymphocyte from a donor mammal having a heterozygous Ikaros lymphocyte, e.g., an Ikaros stem cell or lymphocyte described herein.

In a preferred embodiment, the method further includes: prior to introduction of a cell into the subject, treating the cell to inhibit proliferation, e.g., by irradiating the cells.

In another preferred embodiment: the donor is Ikaros-deregulated; the donor mammal is heterozygous at the Ikaros locus; the mammal carries a mutation at the Ikaros gene, e.g., a deletion for all or part of the Ikaros gene; the mammal is heterozygous or homozygous for an Ikaros transgene.

In another preferred embodiment: the donor mammal is a human or a non-human mammal, e.g., a swine, a monkey, a goat, or a rodent, e.g., a rat or a mouse. In preferred embodiments, e.g., in the case of an Ikaros wild-type donor, e.g., a human donor, the manipulation that gives rise to Ikaros deregulation, e.g., an Ikaros lesion, can be made in vitro.

In a preferred embodiment: the cell is heterozygous or homozygous for an Ikaros transgene, e.g., a transgene having, e.g., a mutation in the DNA binding region, e.g., a point mutation in, or a deletion for all or part of one or more of F1, F2, F3, or F4; the cell is a heterozygous Ikaros cell; the cell is a homozygous mutant Ikaros cell; the lymphocyte is a T lymphocyte, e.g., a CD4+CD8−, CD8+CD4−, CD4+CD8+, CD4−CD8− lymphocyte. In preferred embodiments: the cell is heterozygous or homozygous for an Ikaros transgene, e.g., a transgene having a point mutation or a deletion, which, inactivates one or both of transcriptional activation or dimerization, which decreases the half life of the protein, or which inactivates one or both of the C terminal Zinc finger domains; the cell is heterozygous or homozygous for an Ikaros transgene, e.g., a transgene having a C terminal deletion.

In preferred embodiments, the cell is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments: the method is performed in vivo, and the donor mammal which produces the Ikaros cell or the subject mammal or both are immunized with an antigen. The antigen can be: an alloantigen; a xenoantigen or an autoantigen; a protein; or an antigen which gives rise to an anti-idiotypic lymphocyte.

In another aspect, the invention features, a method of reconstituting an immune system. The method includes: supplying a recipient mammal, e.g., a human or a nonhuman mammal, e.g., a swine, a nonhuman primate, e.g., a monkey, a goat, or a rodent, e.g., a rat or a mouse, and introducing, preferably exogenously, into the animal, an immune system component from a donor mammal, e.g., a human or a nonhuman mammal, e.g., a swine, a monkey, a goat, or a rodent, e.g., a rat or a mouse, which is Ikaros-deregulated, e.g., which carries at least one mutant allele at the Ikaros locus. In preferred embodiments, e.g., if the donor mammal is human, the manipulation that gives rise to Ikaros deregulation, e.g., an Ikaros lesion, can be made in vitro.

In preferred embodiments, the component is an Ikaros deregulated cell, e.g., a hematopoietic cell, e.g., a pluripotent stem cell, or a descendent of a stem cell, e.g., a lymphocyte.

In preferred embodiments, the component is from a donor mammal, e.g., a human or a nonhuman mammal, e.g., a swine, a monkey, a goat, or a rodent, e.g., a rat or a mouse.

In a preferred embodiment, the method further includes: prior to introduction of a component into the subject, treating the lymphocyte to inhibit proliferation, e.g., by irradiating the component.

In a preferred embodiment, the donor mammal carries a mutation at the Ikaros gene, e.g., a deletion of all or part of the Ikaros gene.

In another preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue.

In a preferred embodiment: the immune system component is from the same species as the recipient mammal; the immune system component is from species different from the species of the recipient mammal.

In preferred embodiments: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In a preferred embodiment: the immune system component is a lymphocyte heterozygous or homozygous for an Ikaros transgene, e.g., a transgene having, e.g., a mutation in the DNA binding region, e.g., a point mutation in, or a deletion for all or part of one or more of F1, F2, F3, or F4; the immune system component is a heterozygous Ikaros lymphocyte; the immune system component is a homozygous mutant Ikaros lymphocyte; the immune system component is a T lymphocyte, e.g., a CD4+CD8−, CD8+CD4−, CD4+CD8+ or CD4−CD8− lymphocyte.

In preferred embodiments: the immune system component is a lymphocyte heterozygous or homozygous for an Ikaros transgene, e.g., a transgene having a point mutation or a deletion, which, inactivates one or both of transcriptional activation or dimerization, which decreases the half life of the protein, or which inactivates one or both of the C terminal Zinc finger domains; the immune system component is a lymphocyte heterozygous or homozygous for an Ikaros transgene, e.g., a transgene having a C terminal deletion.

In preferred embodiments, the immune system component is: a helper T cell; or cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; a lymphocyte which is an antigen-nonspecific T cell.

In preferred embodiments: the method is performed in vivo, and the recipient mammal or the donor mammal or both are immunized with an antigen. The antigen can be: an alloantigen; a xenoantigen or an autoantigen; a protein; or an antigen which gives rise to an anti-idiotypic lymphocyte.

In a preferred embodiment, the method further includes: determining a value for a parameter related to immune system function. The parameter related to the immune system function can be any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a method of evaluating the interaction of an Ikaros-deregulated cell, e.g., a hematopoietic cell, e.g., a stem cell, e.g., a totipotent or a pluripotent stem cell, or a descendent of a stem cell, e.g., a lymphocyte, e.g., a lymphocyte having at least one mutant allele at the Ikaros locus with an immune system component. The method includes: supplying an animal, e.g., a swine, a nonhuman primate, e.g., a monkey, a goat, or a rodent, e.g., a rat or a mouse; introducing the cell and the immune component into the animal; and evaluating the interaction between the Ikaros-deregulated cell and the immune system component.

In a preferred embodiment, the method further includes: prior to introduction of a cell into the subject, treating the lymphocyte to inhibit proliferation, e.g., by irradiating the cell.

In a preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal; the immune system component is from the same species as the lymphocyte; the immune system component is from species different from the species from which the lymphocyte is obtained.

In another preferred embodiment: the cell is from the same species as the animal; the cell is from a species which is different from the species of the animal.

In another preferred embodiment: the recipient mammal is a wild-type animal; an animal model for a human disease, e.g., a NOD mouse; the animal is immunocompromised by irradiation, chemotherapy, or genetic defect, e.g., the animal is a SCID mouse or a nude mouse; the recipient is deficient in an immune function, e.g., the recipient has been thymectomized, depleted of an immune system component, e.g., of cells or antibodies; the recipient has been administered chemotherapy or irradiation.

In a preferred embodiment: the cell is heterozygous or homozygous for an Ikaros transgene, e.g., a transgene having a mutation in the DNA binding region, e.g., , a point mutation in, or a deletion for all or part of one or more of F1, F2, F3, or F4; the cell is a heterozygous Ikaros cell; the lymphocyte is a homozygous mutant Ikaros lymphocyte; the lymphocyte is a T lymphocyte, e.g., a CD4+CD8−, CD8+CD4−, CD4+CD8+, CD4−CD8− lymphocyte.

In preferred embodiments: the cell is heterozygous or homozygous for an Ikaros transgene, e.g., a transgene having a point mutation or a deletion, which, inactivates one or both of transcriptional activation or dimerization, which decreases the half life of the protein, or which inactivates one or both of the C terminal Zinc finger domains; the cell is heterozygous or homozygous for an Ikaros transgene, e.g., a transgene having a C terminal deletion.

In preferred embodiments, the cell is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments evaluating can include evaluating any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In preferred embodiments: the method is performed in vivo, and one or more of the animal, the donor of the Ikaros deregulated cell, the donor of the immune system component, is immunized with an antigen. The antigen can be: an alloantigen; a xenoantigen or an autoantigen; a protein; or an antigen which gives rise to an anti-idiotypic lymphocyte.

In another aspect, the invention features, a method of evaluating the interaction of an Ikaros-deregulated cell, e.g., a hematopoietic cell, e.g., a stem cell, e.g., a totipotent or a pluripotent stem cell, or a descendent of a stem cell, e.g., a lymphocyte, e.g., a lymphocyte having at least one mutant allele at the Ikaros locus, with an immune system component including: supplying the cell and the immune system component; exposing the cell to the immune system component in vitro; and evaluating the interaction between the cell and the immune system component.

In preferred embodiments the donor of the lymphocyte is: a human or a nonhuman mammal, e.g., a swine, a monkey, a goat, or a rodent, e.g., a rat or a mouse, which carries at least one mutant allele at the Ikaros locus.

In preferred embodiments the donor of the immune system components is: a human or a nonhuman mammal, e.g., a swine, a monkey, a goat, or a rodent, e.g., a rat or a mouse, which carries at least one mutant allele at the Ikaros locus. In preferred embodiments, e.g., if the donor mammal is human, the manipulation that gives rise to Ikaros deregulation, e.g., an Ikaros lesion, can be made in vitro.

In a preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal; the immune system component is from the same species as the lymphocyte; the immune system component is from species different from the species from which the lymphocyte is obtained.

In another preferred embodiment: the cell is from the same species as the animal; the cell is from species different from the species of the animal.

In a preferred embodiment: the cell is heterozygous or homozygous for an Ikaros transgene, e.g., a transgene having, e.g., a mutation in the DNA binding region, e.g., a point mutation in, or a deletion for all or part of one or more of F1, F2, F3, or F4; the cell is a heterozygous Ikaros cell; the cell is a homozygous mutant Ikaros cell; the lymphocyte is a T lymphocyte, e.g., a CD4+CD8−, CD8+CD4−, CD4+CD8+, CD4−CD8− lymphocyte.

In preferred embodiments: the cell is heterozygous or homozygous for an Ikaros transgene, e.g., a transgene having a point mutation or a deletion, which, inactivates one or both of transcriptional activation or dimerization, which decreases the half life of the protein, or which inactivates one or both of the C terminal Zinc finger domains; the cell is heterozygous or homozygous for an Ikaros transgene, e.g., a transgene having a C terminal deletion.

In preferred embodiments, the cell is a lymphocyte and is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In preferred embodiments evaluating can include evaluating any of: the production of a cytokine; the proliferation or activation of a cell of the immune system; the production of an antibody; the lysis of an antigen presenting cell or the activation of a cytolytic T lymphocyte; resistance to infection; life span; body weight; the presence, function, or morphology of tissues or organs of the immune system; the ability of a component of the immune system to respond to a stimulus (e.g., a diffusable substance, e.g., cytokines, other cells of the immune system, or antigens); the ability to present an antigen; the ability to exhibit immunological tolerance to an alloantigen or a xenoantigen.

In preferred embodiments: the method is performed in vitro, and the donor of the mutant Ikaros cell or the donor of the immune system component or both are immunized with an antigen. The antigen can be: an alloantigen; a xenoantigen or an autoantigen; a protein; or an antigen which gives rise to an anti-idiotypic lymphocyte.

In preferred embodiments the cell expresses a T cell receptor and the cell is stimulated or activated by contacting the cell with an agent which interacts or binds with the T cell receptor, e.g., an antigen or an anti-T cell receptor antibody.

In another aspect, the invention features, a mammal, e.g., a nonhuman mammal, e.g., e.g., a swine, a nonhuman primate, e.g., a monkey, a goat, or a rodent, e.g., a rat or a mouse, having an exogenously introduced immune system component, the component being from a human or nonhuman mammal, e.g., a swine, a nonhuman primate, e.g., a monkey, a goat, or a rodent, e.g., a rat or a mouse, or cell culture which is Ikaros-deregulated or which carries at least one mutant allele at the Ikaros locus. In preferred embodiments, e.g., if the immune system component is from a wild-type animal, e.g., a human, the manipulation that gives rise to Ikaros deregulation, e.g., an Ikaros lesion, can be made in vitro.

In preferred embodiments, the component is from a human or nonhuman mammal, e.g., a swine, a nonhuman primate, e.g., a monkey, a goat, or a rodent, e.g., a rat or a mouse, which is Ikaros-deregulated.

In a preferred embodiment: the immune system component is a lymphocyte heterozygous or homozygous for an Ikaros transgene, e.g., a transgene having, a mutation in the DNA binding region, e.g., a point mutation in, or a deletion for all or part of one or more of F1, F2, F3, or F4; the immune system component is a heterozygous Ikaros lymphocyte; the immune system component is a homozygous mutant Ikaros lymphocyte; the immune system component is a T lymphocyte, e.g., a CD4+CD8−, CD8+CD4−, CD4+CD8+, CD4−CD8− lymphocyte.

In preferred embodiments: the immune system component is a lymphocyte heterozygous or homozygous for an Ikaros transgene, e.g., a transgene having a point mutation or a deletion, which, inactivates one or both of transcriptional activation or dimerization, which decreases the half life of the protein, or which inactivates one or both of the C terminal Zinc finger domains; the immune system component is a lymphocyte heterozygous or homozygous for a C terminal deletion.

In preferred embodiments, the immune system component is: a helper T cell; cytolytic T cell; a suppressor T cell; a T cell which secretes one or more anti-inflammatory cytokines, e.g., IL-4, IL- 10, or IL- 13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the animal; the immune system component is from species different from the species of the animal.

In preferred embodiments: the mammal or the donor animal which produces the immune system component or both are immunized with an antigen. The antigen can be: an alloantigen; a xenoantigen or an autoantigen; a protein; or an antigen which gives rise to an anti-idiotypic lymphocyte.

In another aspect, the invention features, a reaction mixture, preferably an in vitro reaction mixture, including an immune system component, the component being from an animal or cell culture which is Ikaros-deregulated or which carries at least one mutant allele at the Ikaros locus, and a target tissue or cell, e.g., target lymphocyte, wherein preferably, the immune system component and the target differ in genotype at a locus other than the Ikaros locus; the component and the target are from different species, or the component and the target are from different animals.

In preferred embodiments, the component is from an animal or cell culture which is Ikaros-deregulated.

In a preferred embodiment: the immune system component is a lymphocyte heterozygous or homozygous for an Ikaros transgene, e.g., a transgene having a mutation in the DNA binding region, e.g., a point mutation in, or a deletion for all or part of one or more of F1, F2, F3, or F4; the immune system component is a heterozygous Ikaros lymphocyte; the immune system component is a homozygous mutant Ikaros lymphocyte; the immune system component is a T lymphocyte, e.g., a CD4+CD8−, CD8+CD4−, CD4+CD8+, CD4−CD8− lymphocyte.

In preferred embodiments: the immune system component is a lymphocyte heterozygous or homozygous for an Ikaros transgene, e.g., a transgene having a point mutation or a deletion, which, inactivates one or both of transcriptional activation or dimerization, which decreases the half life of the protein, or which inactivates one or both of the C terminal Zinc finger domains; the immune system component is a lymphocyte heterozygous or homozygous for a C terminal deletion.

In preferred embodiments, the immune system component is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In another preferred embodiment: the immune system component is any of a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue; the immune system component is from the same species as the target cell; the immune system component is from species different from the species of the target cell.

In a preferred embodiment: the target is selected from a group consisting of T or B lymphocytes, macrophages, inflammatory leukocytes, e.g., neutrophils or eosinophils, mononuclear phagocytes, NK cells or T lymphocytes; the target is an antigen presenting cell, e.g., a professional antigen presenting cell or a nonprofessional antigen presenting cell; the target is spleen tissue, lymph node tissue, bone marrow tissue or thymic tissue In preferred embodiments: the donor of the immune system component or the donor of the target or both are immunized with an antigen. The antigen can be: an alloantigen; a xenoantigen or an autoantigen; a protein; or an antigen which gives rise to an anti-idiotypic lymphocyte.

In preferred embodiments the donor of the components is: a human or nonhuman mammal, e.g., a swine, a nonhuman primate, e.g., a monkey, a goat, or a rodent, e.g., a rat or mouse. In preferred embodiments, e.g., in the case of a wild-type donor, e.g., a human, the manipulation that gives rise to Ikaros deregulation, e.g., an Ikaros lesion, can be introduced in vitro.

In preferred embodiments the donor of the target is: a human or nonhuman mammal, e.g., a swine, a nonhuman primate, e.g., a monkey, a goat, or a rodent, e.g., a rat or mouse.

In another aspect, the invention features, a reaction mixture preferably an in vitro reaction mixture, having an immune system component, the component being from a human or nonhuman mammal, e.g., an animal, e.g., a swine, a nonhuman primate, e.g., a monkey, a goat, or a rodent, e.g., a rat or a mouse, or cell culture, which is Ikaros deregulated or which carries a mutant allele at least one Ikaros locus, and an exogenously introduced cytokine, e.g., IL-2. If the donor is a human, the Ikaros lesion can be made in vitro.

In a preferred embodiment: the immune system component is a lymphocyte heterozygous or homozygous for an Ikaros transgene, e.g., a transgene having, e.g., a point mutation in, or a deletion for all or part of one or more of F1, F2, F3, or F4; the immune system component is a heterozygous Ikaros lymphocyte; the immune system component is a homozygous mutant Ikaros lymphocyte; the immune system component is a T lymphocyte, e.g., a CD4+CD8−, CD8+CD4−, CD4+CD8+, CD4−CD8− lymphocyte.

In preferred embodiments, the immune system component is: a helper T cell; cytolytic T cell; a suppressor T cell; a T cell which secretes one or more anti-inflammatory cytokines, e.g., IL-4, IL-10, or IL-13; a T cell which is antigen or idiotype specific; a suppressor T cell which is anti-idiotypic for an auto antibody or for an antibody which recognizes an allograft or xenograft tissue; the lymphocyte is an antigen-nonspecific T cell.

In another preferred embodiment: the immune system component is any of a T cell, a T cell progenitor, a totipotent hematopoietic stem cell, a pluripotent hematopoietic stem cell, a B cell, a B cell progenitor, a natural killer cell, a natural killer cell progenitor, bone marrow tissue, spleen tissue, or thymic tissue.

In preferred embodiments: the donor of the immune system component is immunized with an antigen. The antigen can be: an alloantigen; a xenoantigen or an autoantigen; a protein; or an antigen which gives rise to an anti-idiotypic lymphocyte.

In another aspect, the invention features, a method of promoting the proliferation of a cell, e.g., a hematopoietic cell, e.g., a stem cell, e.g., a totipotent or a pluripotent stem cell, or a descendent of a stem cell, e.g., a lymphocyte. The method includes: administering to the cell a compound which inhibits the formation of non-proliferative Ikaros dimers (NPID). The method can be performed in vivo or in vitro.

In preferred embodiments, the compound is: a competitive or noncompetitive inhibitor of the association of NPID subunits; the compound binds to an Ik-1, Ik-2, or Ik-3 isoform, preferably to the F5 and F6 region of exon 7 of the isoform; a fragment of an Ikaros protein, e.g., a fragment which includes F5 and F6 or an Ik-1, Ik-2, or Ik-3 binding portion thereof; the compound is a fragment of an Ikaros protein equal to or less than 150, 100, 70, 58, 52, 50, 40, or 30 amino acids in length; a fragment of an Ikaros protein which includes the C-terminal 150 amino acid residues of exon 7, more preferably the 58 C-terminal amino acid residues; a fragment which includes F5 and the first 20 amino acid residues of F6; a fragment which includes F5 and the first 22 amino acid residues of F6; an interaction deficient Ikaros species; an Ikaros peptide wherein one or more of F1, F2, F3, or F4 is nonfunctional or deleted; an Ikaros protein or fragment which binds any of IK-1, Ik-2, or Ik-3, and which permits activation at a less than wild type level, e.g., the I3 variant described herein.

In preferred embodiments the cell expresses a T cell receptor and the cell is stimulated or activated by contacting the cell with an agent which interacts or binds with the T cell receptor, e.g., an antigen or an anti-T cell receptor antibody.

In preferred embodiments the compound is: a protein or peptide; a peptomimetic, a small molecule; a nucleic acid which encodes an inhibitor.

In another aspect, the invention features, a method of promoting the engraftment or proliferation of an autologous, allogeneic, or xenogeneic hematopoietic stem cell in an a recipient animal, e.g., a rodent, e.g., a rat or mouse, a swine, or a human or nonhuman primate. The method includes administering a hemapoietic stem cell, preferably an Ikaros-deregulated stem cell, to the recipient.

In preferred embodiments the method further includes administering, to the stem cell or the recipient, or both, a compound which: is a competitive or noncompetitive inhibitor of the association of NPID subunits; binds to an Ik-1, Ik-2, or Ik-3 isoform, preferably to the F5 and F6 region of exon 7 of the isoform; a fragment of an Ikaros protein, e.g., a fragment which includes F5 and F6 or an Ik-1, Ik-2, or Ik-3 binding portion thereof; is a fragment of an Ikaros protein equal to or less than 150, 100, 70, 58, 52, 50, 40, or 30 amino acids in length; is a fragment of an Ikaros protein which includes the C-terminal 150 amino acid residues of exon 7, more preferably the 58 C-terminal amino acid residues; is a fragment which includes F5 and the first 20 amino acid residues of F6; a fragment which includes F5 and the first 22 amino acid residues of F6; an interaction deficient Ikaros species; is an Ikaros peptide wherein one or more of F1, F2, F3, or F4 is nonfunctional or deleted; is an Ikaros protein or fragment which binds any of IK-1, Ik-2, or Ik-3, and which permits activation at a less than wild type level, e.g., the 13 variant described herein.

In preferred embodiments the compound is: a protein or peptide; a peptomimetic, a small molecule; a nucleic acid which encodes an inhibitor.

In another aspect, the invention features, a method of providing a cell, e.g., a hematopoietic cell, e.g., a stem cell, e.g., a totipotent or a pluripotent stem cell, or a descendent of a stem cell, e.g., a lymphocyte, having enhanced proliferation including deregulating the Ikaros locus of the cell.

In another aspect, the invention features, a purified preparation of Ikaros deregulated cells, e.g., hematopoietic cells, e.g., a stem cells, e.g., totipotent or pluripotent stem cells, or descendants of a stem cell, e.g., lymphocytes.

In another aspect, the invention features a recombinant or substantially pure preparation of an Ikaros polypeptide having any of: a mutation, e.g., a point mutation or a deletion, which, inactivates (entirely or partially) one or both of transcriptional activation or dimerization, which decreases the half life of the protein, or which inactivates (entirely or partially) one or both of the C terminal Zinc finger domains, e.g., a C terminal deletion or a deletion of all or part of exon 7. The sequence of human and mouse Ikaros can be found in Molnar et al., *J Immunol.* 156:585–592, 1996, hereby incorporated by reference.

In preferred embodiments: the polypeptide has biological activity; the polypeptide includes an amino acid sequence at least 60%, 80%, 90%, 95%, 98%, or 99% homologous to a naturally occurring Ikaros polypeptide; the polypeptide includes an amino acid sequence essentially the same as a naturally occurring Ikaros polypeptide; the polypeptide is at least 20, 50, 100, or 150 amino acids in length; the polypeptide includes at least 20, most preferably at least 50, 100, or 150 contiguous amino acids from a naturally occurring Ikaros polypeptide; the polypeptide is either, an agonist or an antagonist, of a biological activity of a naturally occurring Ikaros polypeptide. For example, the polypeptide is an agonist or antagonist of a naturally occurring Ikaros polypeptide; the polypeptide is a vertebrate, e.g., a mammalian, e.g. a primate, e.g., a human, Ikaros polypeptide.

In preferred embodiments: the Ikaros polypeptide is encoded by the nucleic acid of a naturally occurring Ikaros polypeptide, or by a nucleic acid having at least 60%, 70%, 80%, 90%, 95%, 98%, or 99% homology with the nucleic acid of a naturally occurring Ikaros polypeptide.

In a preferred embodiment, the Ikaros polypeptide differs in amino acid sequence at up to 1, 2, 3, 5, or 10 residues, from a sequence of a naturally occurring Ikaros polypeptide. In other preferred embodiments, the Ikaros polypeptide differs in amino acid sequence at up to 1, 2, 3, 5, or 10% of the residues from a sequence of a naturally occurring Ikaros polypeptide. Preferably, the differences are such that: the Ikaros polypeptide exhibits a Ikaros biological activity, e.g., the Ikaros polypeptide retains a biological activity of a naturally occurring Ikaros polypeptide or the polypeptide is an antagonist of a naturally occurring Ikaros polypeptide.

In preferred embodiments, the Ikaros polypeptide includes all or a fragment of an amino acid sequence of a naturally occurring Ikaros polypeptide, fused, in reading frame, to additional amino acid residues, preferably to residues encoded by genomic DNA 5' to the genomic DNA which encodes a sequence of a naturally occurring Ikaros polypeptide.

In yet other preferred embodiments, the Ikaros polypeptide is a recombinant fusion protein having a first Ikaros portion and a second polypeptide portion, e.g., a second polypeptide portion having an amino acid sequence unrelated to an Ikaros polypeptide. The second polypeptide portion can be, e.g., any of glutathione-S-transferase, a DNA binding domain, or a polymerase activating domain. In preferred embodiment the fusion protein can be used in a two-hybrid assay.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed Ikaros polypeptide is expressed in a native cell, or in systems which result in the omission of postranslational modifications present when expressed in a native cell.

The invention includes an immunogen which includes an Ikaros polypeptide in an immunogenic preparation, the immunogen being capable of eliciting an immune response specific for the Ikaros polypeptide, e.g., a humoral response, an antibody response, or a cellular response. In preferred embodiments, the immunogen comprising an antigenic determinant, e.g., a unique determinant, from a protein represented by a naturally occurring Ikaros polypeptide.

The present invention also includes an antibody preparation specifically reactive with an epitope of the Ikaros immunogen or generally of an Ikaros polypeptide, preferably an epitope, which when bound to an antibody, results in the modulation of a biological activity.

Also included in the invention is a composition which includes an Ikaros polypeptide (or a nucleic acid which encodes it) and one or more additional components, e.g., a carrier, diluent, or solvent. The additional component can be one which renders the composition useful for in vitro, in vivo, pharmaceutical, or veterinary use.

In another aspect, the invention provides a substantially pure nucleic acid having or comprising a nucleotide sequence which encodes a polypeptide, the amino acid sequence of which includes, or is, the sequence of an Ikaros polypeptide having any of: a mutation, e.g., a point mutation or a deletion, which, inactivates (entirely or partially) one or both of transcriptional activation or dimerization, which decreases the half life of the protein, or which inactivates (entirely or partially) one or both of the C terminal Zinc finger domains, e.g., a C terminal deletion or a deletion of all or part of exon 7.

In preferred embodiments: the encoded polypeptide has biological activity; the encoded polypeptide includes an amino acid sequence at least 60%, 80%, 90%, 95%, 98%, or 99% homologous to a naturally occurring Ikaros polypeptide; the encoded polypeptide includes an amino acid sequence essentially the same as a naturally occurring Ikaros polypeptide; the encoded polypeptide is at least 20, 50, 100, or 150 amino acids in length; the encoded polypeptide includes at least 20, most preferably at least 50, 100, or 150 contiguous amino acids from a naturally occurring Ikaros polypeptide; the encoded polypeptide is either, an agonist or an antagonist, of a biological activity of a naturally occurring Ikaros polypeptide. For example, the encoded polypeptide is an agonist or antagonist of a naturally occurring Ikaros polypeptide; the encoded polypeptide is a vertebrate, e.g., a mammalian, e.g. a primate, e.g., a human, Ikaros polypeptide.

In preferred embodiments: the encoded Ikaros polypeptide is encoded by the nucleic acid of a naturally occurring Ikaros polypeptide, or by a nucleic acid having at least 60%, 70%, 80%, 90%, 95%, 98%, or 99% homology with the nucleic acid of a naturally occurring Ikaros polypeptide.

In a preferred embodiment, the encoded Ikaros polypeptide differs in amino acid sequence at up to 1, 2, 3, 5, or 10 residues, from a sequence of a naturally occurring Ikaros polypeptide. In other preferred embodiments, the encoded Ikaros polypeptide differs in amino acid sequence at up to 1, 2, 3, 5, or 10% of the residues from a sequence of a naturally occurring Ikaros polypeptide. Preferably, the differences are such that: the encoded Ikaros polypeptide exhibits an Ikaros biological activity, e.g., the encoded Ikaros polypeptide retains a biological activity of a naturally occurring Ikaros polypeptide or the encoded polypeptide is an antagonist of a naturally occurring Ikaros polypeptide.

In preferred embodiments, the encoded Ikaros polypeptide includes all or a fragment of an amino acid sequence of a naturally occurring Ikaros polypeptide, fused, in reading frame, to additional amino acid residues, preferably to residues encoded by genomic DNA 5' to the genomic DNA which encodes a sequence of a naturally occurring Ikaros polypeptide.

In yet other preferred embodiments, the encoded Ikaros polypeptide is a recombinant fusion protein having a first Ikaros portion and a second polypeptide portion, e.g., a second polypeptide portion having an amino acid sequence unrelated to an Ikaros polypeptide. The second polypeptide portion can be, e.g., any of glutathione-S-transferase, a DNA binding domain, or a polymerase activating domain. In preferred embodiment the fusion protein can be used in a two-hybrid assay.

In preferred embodiments, the subject Ikaros nucleic acid will include a transcriptional regulatory sequence, e.g. at least one of a transcriptional promoter or transcriptional enhancer sequence, operably linked to the Ikaros gene sequence, e.g., to render the Ikaros gene sequence suitable for use as an expression vector.

In yet a further preferred embodiment, the nucleic acid which encodes an Ikaros polypeptide of the invention, hybridizes under stringent conditions to a nucleic acid probe corresponding to at least 12 consecutive nucleotides of a naturally occurring Ikaros polypeptide, more preferably to at least 20 consecutive nucleotides of a naturally occurring Ikaros polypeptide.

In another aspect, the invention features a cell or purified preparation of cells which include an Ikaros transgene, or which otherwise misexpress an Ikaros gene. The cell preparation can consist of human or non human cells, e.g., rodent cells, e.g., mouse or rat cells, rabbit cells, or pig cells. In preferred embodiments, the cell or cells include an Ikaros transgene, e.g., a heterologous form of an Ikaros gene, e.g., a gene derived from humans (in the case of a non-human cell). The Ikaros transgene can be misexpressed, e.g., overexpressed or underexpressed. In other preferred embodiments, the cell or cells include a gene which misexpress an endogenous Ikaros gene, e.g., a gene the expression of which is disrupted, e.g., a knockout. Such cells can serve as a model for studying disorders which are related to mutated or mis-expressed Ikaros alleles or for use in drug screening.

In another aspect, the invention features a transgenic Ikaros animal, e.g., a rodent, e.g., a mouse or a rat, a rabbit, or a pig. In preferred embodiments, the transgenic animal includes (and preferably express) a heterologous form of an Ikaros gene, e.g., a gene derived from humans. In other preferred embodiments, the animal has an endogenous Ikaros gene which is misexpressed, e.g., a knockout. Such a transgenic animal can serve as a model for studying disorders which are related to mutated or mis-expressed Ikaros alleles or for use in drug screening.

The Ikaros polypeptide having any of: a mutation, e.g., a point mutation or a deletion, which, inactivates (entirely or partially) one or both of transcriptional activation or dimerization, which decreases the half life of the protein, or which inactivates (entirely or partially) one or both of the C terminal Zinc finger domains, e.g., a C terminal deletion or a deletion of all or part of exon 7, can be used in any method described herein or in any method described in copending applications U.S. Ser. No. 08/238,212, filed May 2, 1994, U.S. Ser. No. 08/283,300, filed Jul. 29, 1994, and Provisional Application No. 60/017,646, filed May 14, 1996, which are hereby incorporated by reference.

In another aspect, the invention features a method of modulating the rate of division or amplification of a cell, or entry of the cell into the cell cycle. The method includes administering to the cell, an effective amount of an Ikaros polypeptide, or a nucleic acid encoding an Ikaros polypeptide. The method can be practiced ex vivo, in vivo, or in vitro.

In preferred embodiments, the cell is a hematopoietic cell, e.g., a stem cell, e.g., a totipotent or a pluripotent stem cell, or a descendent of a stem cell, e.g., a lymphocyte. In preferred embodiments the cell is a human, a pig, a rabbit, or a rodent, e.g., a mouse or rat, cell.

In preferred embodiments the division or amplification, or entry into the cell cycle, is promoted. Generally, Ikaros mutations which inhibit or antagonize normal non-proliferative Ikaros function (e.g., the function of the Ik-1 isoform) increase cell division. Such mutants include: mutations which inhibit DNA binding, e.g., point mutations in, or deletions for all or part of, one or more of F1, F2, F3, or F4; mutations, e.g., point mutations in, or deletions for all or part of, one or more of exons ½, 3, 4, 5, or 6; mutations which results in the preferential expression of proliferation-promoting Ikaros dimer subunits as opposed to nonproliferation-promoting Ikaros dimer subunits; or mutants having defective DNA binding but functional dimerization domains. Less preferred are mutations which inactivate one or both of transcriptional activation or dimerization, which decrease the half life of the protein, or which inactivate one or both of the C terminal Zinc finger domains, e.g., F5 or F6; or a mutation is a C terminal deletion. Fragments or other mutants of Ikaros (or Aiolos) which inhibit dimerization of Ikaros proteins, e.g., fragments which include the C terminal dimerization region, e.g., fragments which include Zinc fingers F5 and F6, can also be used to promote cell division. Subunits of proliferation-promoting Ikaros dimers can also increase division, amplification, or entry into the cell cycle.

Methods for increasing cell division can be combined with procedures where it is desirable to increase cell division, e.g., the treatment, e.g., by chemotherapy or radiotherapy, of tumors or other cell-proliferative disorders.

In preferred embodiments the division, amplification, or entry into the cell cycle is decreased. Subunits of non-proliferation-promoting Ikaros dimers, e.g., Ik-1, can decrease division, amplification, or entry into the cell cycle.

Cells, e.g., stem cells, treated by the method of the invention can be introduced into mammals, e.g., humans, non-human primates, or other mammals, e.g., rodents. In preferred embodiments the treatment is performed ex vivo and: the cell is autologous, e.g., it is returned to the same individual from which it was derived; the cell is allogeneic, i.e., it is from the same species as the mammal to which it is administered; the cell is xenogeneic, i.e., it is from a different species from the mammal to which it is administered.

In another aspect, the invention features a method of modulating the state of differentiation of a cell. The method includes administering to the cell, an Ikaros polypeptide, or a nucleic acid encoding an Ikaros polypeptide, in an amount sufficient to modulate, e.g., to promote the maintenance of the state of differentiation of the cell, or to promote differentiation. The method can be practiced ex vivo, in vivo, or in vitro.

In preferred embodiments, the cell is a hematopoietic cell, e.g., a stem cell, e.g., a totipotent or a pluripotent stem cell, or a descendent of a stem cell, e.g., a lymphocyte. In preferred embodiments the cell is a human, a pig, a rabbit, or a rodent, e.g., a mouse or rat, cell.

In preferred embodiments, the state of differentiation of the cell is maintained, e.g., differentiation is inhibited and a more primitive and more multipotent state is promoted. This can be achieved by providing Ikaros polypeptides having wild type non-proliferative function, e.g., Ikaros polypeptides having the function of the Ik-1 isoform. Subunits of non-proliferation-promoting Ikaros dimers can promote maintenance of the differentiated state of the cell. In a particularly preferred embodiment wild type Ikaros function is provided to human hematopoietic cells, preferably stem cells, to maintain their differentiated state or to otherwise enhance culturing of the cells.

In preferred embodiments, differentiation of the cell, which is usually accompanied by entry into the cell cycle, is promoted. Generally, Ikaros mutations which inhibit or antagonize normal non-proliferative Ikaros function (e.g., the function of the Ik-1 isoform) promote differentiation. Such mutants include: mutations which inhibit DNA binding, e.g., point mutations in, or deletions for all or part of, one or more of F 1, F2, F3, or F4; mutations e.g., point mutations in, or deletions for all or part of, one or more of exons ½, 3, 4, 5, or 6; mutations which results in the preferential expression of proliferation-promoting Ikaros dimer subunits as opposed to non-proliferation-promoting Ikaros dimer subunits; or mutants having defective DNA binding but functional dimerization domains. Less preferred for promoting differentiation are mutations which inactivate one or both of transcriptional activation or dimerization, which decrease the half life of the protein, or which inactivate one or both of the C terminal Zinc finger domains, e.g., F5 or F6; or a mutation is a C terminal deletion. Fragments or other mutants of Ikaros (or Aiolos) which inhibit dimerization of non-proliferative Ikaros proteins, e.g., fragments which include the C terminal dimerization region, e.g., fragments which include Zinc fingers F5 and F6, can also be used to promote differentiation. Subunits of proliferation-promoting Ikaros dimers can be used to promote differentiation.

Cells, e.g., stem cells, treated by the method of the invention can be introduced into mammals, e.g., humans, non-human primates, or other mammals, e.g., rodents. In preferred embodiments the treatment is performed ex vivo and: the cell is autologous, e.g., it is returned to the same individual from which it was derived; the cell is allogeneic, i.e., it is from the same species as the mammal to which it is administered; the cell is xenogeneic, i.e., it is from a different species from the mammal to which it is administered.

In another aspect, the invention features a cell having an Ikaros mutation and a mutation other than the Ikaros mutation, e.g., a mutation in a gene involved in the regulation of the lymphoid system, e.g., an Aiolos mutation.

In preferred embodiments, the Ikaros mutation is: a point mutation in, or a deletion for all or part of one or more of F1, F2, F3, or F4; a mutation in the DNA binding region, e.g., a point mutation in, or a deletion for all or part of one or more of F1, F2, F3. or F4; a mutation in the control region of the Ikaros gene which results in the preferential expression of PPID subunits as opposed to NPID subunits; a point mutation or a deletion, which, inactivates one or both of transcriptional activation or dimerization, which decreases the half life of the protein, or which inactivates one or both of the C terminal Zinc finger domains, e.g., F5 or F6; or a mutation is a C terminal deletion.

In other preferred embodiments, the cell is a hematopoietic cell, e.g., a stem cell, e.g., a totipotent or a pluripotent stem cell, or a descendent of a stem cell, e.g., a lymphocyte.

A proliferation-deregulated cell, as used herein, refers to an Ikaros-deregulated cell or to the clonal descendent of an Ikaros-deregulated cell.

An Ikaros-deregulated cell, as used herein, is a cell in which the concentration or activity of "non-proliferative Ikaros dimers" (NPID), e.g., Ik-1/Ik-1, Ik-1/Ik-2, Ik-1/Ik-3, Ik-2/Ik-2. Ik-2/Ik-3 or Ik-3/Ik-3, has been manipulated so as to be sufficiently reduced to allow increased proliferation of the cell. Increased proliferation can mean: increased proliferation as compared to an otherwise similar cell without the manipulation, or increased proliferation as compared to a wild-type cell. The concentration or activity of an NPID can be manipulated by any means known to the art. The concentration or activity of an NPID can be reduced by reducing the availability of one or more monomeric species which can form an NPID, e.g., by reducing the availability of one or more of Ik-1, Ik-2, or Ik-3. Such reduction can be effected by mutations which decrease production of Ik-1, Ik-2, or Ik-3, by the expression of antisense molecules which inhibit Ik-1, Ik-2, or Ik-3 expression or by compounds which inhibit dimerization of the subunits of NPID's. The concentration or activity of NPID's can be reduced by providing Ikaros species which lack one or more functional F1, F2, F3, or F4 zinc finger regions, e.g., by producing Ik-4, Ik-5, Ik-6, or Ik-7 isoforms. Such species can form proliferation-promoting Ikaros dimers (PPID). PPID's are dimers in which at least one of the subunits has less than 4 functional N-terminal zinc fingers (the N-terminal zinc fingers are zinc fingers F 1, F2, F3, and F4). Thus, manipulations which reduce the concentration or activity of NPID, e.g., by sequestering available Ik-1, Ik-2, or Ik-3 in PPID's, can be used to provide an Ikaros-deregulated lymphocyte.

Ikaros-deregulated cells include any cell the proliferation of which is affected by the ratio of NPID to PPID, including hematopoietic cells, e.g., a stem cells, e.g., totipotent or a pluripotent stem cells, or descendants of stem cells, e.g., lymphocytes, in which the ratio of NPID to PPID has been manipulated. An Ikaros-deregulated cell includes cells having one or more of the following characteristics: the ratio of Ik-1, Ik-2, and Ik-3 to Ik-4, Ik-5, Ik-6, and Ik-7, is less than or equal to 10, 5, 4, 2, 1, 0.5, 0.25; the ratio of NPID to PPID is less than or equal to 10, 5, 4, 2, 1, 0.5, 0.25; the cell includes at least one Ikaros-encoding nucleic acid sequence which encodes less than 4 N-terminal zinc fingers, e.g., it is deleted for sequence which encodes one or more of F1, F2, F3, or F4; the cell includes at least one Ikaros-encoding nucleic acid sequence which encodes one or more of a nonfunctional F1, F2, F3, or F4; the cell includes a nucleic acid which encodes an Ikaros fragment, e.g., a fragment which includes F5 and F6, which can inhibit the formation of an NPID, e.g., by competitively inhibiting an interaction between the F5/F6 regions and the subunits of the NPID; the cell includes a nucleic acid sequence which encodes an antisense molecule, the antisense molecule being capable of hybridizing to an Ik-1, Ik-2, or Ik-3, encoding RNA but preferably incapable of hybridizing to an Ik-5, Ik-6, or Ik-7 RNA. Ikaros cells are preferably other than fetal cells.

An Ikaros-deregulated animal, as used herein, is an animal in which one or more, and preferably substantially all, of the cells are Ikaros-deregulated. Ikaros animals are preferably other than fetal animals.

An Ikaros-deregulated component or tissue, as used herein, is a tissue or component in which one or more, and preferably substantially all, of the cells are Ikaros-deregulated. An Ikaros component or tissue is preferably other fetal.

A mutation at the Ikaros locus, as used herein, includes any mutation which alters the expression, structure, or activity of the Ikaros gene or its gene product. These include point mutations in and in particular deletions of all or part of the Ikaros coding region or its control region.

An exogenously supplied cell, tissue, or cell product, e.g., a cytokine, as used herein, is a cell, tissue, or a cell product which is derived from an animal other than the one to which is supplied or administered. It can be from the same species or from different species than the animal to which it is supplied.

A clonal population of lymphocytes, as used herein, is a population of two or more lymphocytes which have one or more of the following properties: they share a common stem cell ancestor; they share a common pre-thymocyte ancestor; they share a common thymocyte ancestor; they share the same T cell receptor genomic rearrangement; they share a common CD4+CD8+ ancestor; they share a common CD4+ ancestor; they share a common CD8+ ancestor; they share a common CD4−CD8− ancestor; they recognize the same antigen.

A substantially homogenous population of two or more cells e.g., lymphocytes, as used herein, means a population of cells in which at least 50% of the cells, more preferably at least 70% of the cells, more preferably at least 80% of the cells, most preferably at least 90%, 95% or 99% of the subject cell type, e.g., lymphocytes. With respect to the Ikaros locus however, the cells can be all (+/−), all (−/−), or a mixture of (+/−) and (−/−) cells.

Culturing, as used herein, means contacting a cell or tissue with an environment which will support viability of the cell or tissue and which preferably supports proliferation of the cell or tissue.

A substantially purified preparation of cells, e.g., lymphocytes, as used herein, means a preparation of cells in which at least 50% of the cells, more preferably at least 70% of the cells, more preferably at least 80% of the cells, most preferably at least 90%, 95% or 99% of the cells of the subject cell, e.g., are lymphocytes. With respect to the Ikaros locus however, the cells can be all (+/−), all (−/−), or a mixture of (+/−) and (−/−) cells.

Immunocompromised, as used herein, refers to a mammal in which at least one aspect of the immune system functions below the levels observed in a wild-type mammal. The mammal can be immunocompromised by a chemical treatment, by irradiation, or by a genetic lesion resulting in, e.g., a nude, a beige, a nude-beige, or an Ikaros—phenotype. The mammal can also be immunocompromised by an acquired disorder, e.g., by a virus, e.g., HIV.

The term "Ikaros" as used herein to refer to a gene, a transgene, or a nucleic acid, refers to a nucleic acid sequence which is at least about 50%, preferably at least about 60%, more preferably at least about 70%, yet more preferably at least about 80%, most preferably at least about 90%–100% homologous with a naturally occurring Ikaros gene or portion thereof, e.g., with the nucleic acid sequence of human Ikaros described in Georgopoulos et al.(1992) *Science* 258:808–812, or Molnar and Georgopoulos (1994) *Mol. Cell Biol.* 14:8292–8303.

As used herein, the term "transgene" refers to a nucleic acid sequence (encoding, e.g., one or more Ikaros proteins), which is inserted by artifice into a cell. The transgene can become part of the genome of an animal which develops in whole or in part from that cell. If the transgene is integrated into the genome it results in a change in the nucleic acid sequence of the genome into which it is inserted. A transgene can be partly or entirely species-heterologous, i.e., the transgene, or a portion thereof, can be from a species which is different from the cell into which it is introduced. A transgene can be partly or entirely species-homologous, i.e., the transgene, or a portion thereof, can be from the same species as is the cell into which it is introduced. If a transgene is homologous (in the sequence sense or in the species-homologous sense) to an endogenous gene of the cell into which it is introduced, then the transgene, preferably, has one or more of the following characteristics: it is designed for insertion, or is inserted, into the cell's genome in such a way as to alter the sequence of the genome of the cell into which it is inserted (e.g., it is inserted at a location which differs from that of the endogenous gene or its insertion results in a change in the sequence of the endogenous gene); it includes a mutation, e.g., a mutation which results in misexpression of the transgene; by virtue of its insertion, it can result in misexpression of the gene into which it is inserted, e.g., the insertion can result in a knockout of the gene into which it is inserted. A transgene can include one or more transcriptional regulatory sequences and any other nucleic acid sequences, such as introns, that may be necessary for a desired level or pattern of expression of a selected nucleic acid, all operably linked to the selected nucleic acid. The transgene can include an enhancer sequence. The transgene is typically introduced into the animal, or an ancestor of the animal, at a prenatal, e.g., an embryonic stage.

As used herein, an Ikaros transgene, is a transgene which includes all or part of an Ikaros coding sequence or regulatory sequence. The term also includes DNA sequences which when integrated into the genome disrupt or otherwise mutagenize the Ikaros locus. Ikaros transgenes sequences which when integrated result in a deletion of all or part of the Ikaros gene. Included are transgenes: which upon insertion result in the misexpression of an endogenous Ikaros gene; which upon insertion result in an additional copy of an Ikaros gene in the cell; which upon insertion place a non-Ikaros gene under the control of an Ikaros regulatory region. Also included are transgenes: which include a copy of the Ikaros gene having a mutation, e.g., a deletion or other mutation which results in misexpression of the transgene (as compared with wild type); which include a functional copy of an Ikaros gene (i.e., a sequence having at least 5% of a wild type activity, e.g., the ability to support the development of T, B, or NK cells); which include a functional (i.e., having at least 5% of a wild type activity, e.g., at least 5% of a wild type level of transcription) or nonfunctional (i.e., having less than 5% of a wild type activity, e.g., less than a 5% of a wild type level of transcription) Ikaros regulatory region which can (optionally) be operably linked to a nucleic acid sequence which encodes a wild type or mutant Ikaros gene product or, a gene product other than an Ikaros gene product, e.g., a reporter gene, a toxin gene, or a gene which is to be expressed in a tissue or at a developmental stage at which Ikaros is expressed. Preferably, the transgene includes at least 10, 20, 30, 40, 50, 100, 200, 500, 1,000, or 2,000 base pairs which have at least 50, 60, 70, 80, 90, 95, or 99% homology with a naturally occurring Ikaros sequence. Preferably, the transgene includes a deletion of all or some of exons 3 and 4, or a deletion for some or all of exon 7 of the Ikaros gene.

As used herein, the term "transgenic cell" refers to a cell containing a transgene.

As used herein, a "transgenic animal" is any animal, e.g., a non-human mammal, e.g., a swine, a monkey, a goat, or a rodent, e.g., a rat or mouse, in which one or more, and preferably essentially all, of the cells of the animal include a transgene. The transgene is introduced into the cell, directly or indirectly by introduction into a precursor of the cell, by way of deliberate genetic manipulation, such as by microinjection or by infection with a recombinant virus. The term genetic manipulation is directed to the introduction of a recombinant DNA molecule. This molecule may be integrated within a chromosome, or it may be extrachromosomally replicating DNA.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of the tissue specificity of expression, e.g., increased or decreased expression (as compared with wild type) in a predetermined cell type or tissue type; a pattern of expression that differs from wild type in terms of the size, amino acid sequence, post-translational modification, or a biological activity of an Ikaros gene product; a pattern of expression that differs from wild type in terms of the effect of an environmental stimulus or extracellullar stimulus on expression of the gene, e.g., a pattern of increased or decreased expression (as compared with wild type) in the presence of an increase or decrease in the strength of the stimulus; or a pattern of isoform expression which differs from wild type.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the sequence similarity between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

The terms peptide, protein, and polypeptide are used interchangeably herein.

The central and multifaceted role of Ikaros in development, and the variety of phenotypes exhibited by Ikaros-deregulated animals and Ikaros-deregulated and proliferation-deregulated lymphocyte cells, render these animals and cells useful, e.g., in a variety of assays, screens, and other methods. E.g., animals, cells and methods of the invention can be used to elucidate and characterize the function of the immune system, mechanisms of development, ways in which components of the immune system interact, ways in which the cell cycle is regulated, mechanisms of immune tolerance, and mechanisms of the development of immune or nervous tissue disorders. The cells, animals, and methods of the invention are also useful, e.g., for evaluating or discovering treatments which can be used to treat immune or nervous tissue disorders, for discovering or for evaluating treatments or methods of inducing immunological tolerance, e.g., to transplanted tissues. Ikaros mice which develop lymphomas are useful not only for investigating the molecular basis of these disorders but for screening treatments for the ability to treat such disorders. Ikaros mice which lack one or more components of the immune system are useful in a variety of reconstitution experiments. Animals, cells, and methods of the invention are also useful for producing clonal populations of lymphocytes.

Other features and advantages of the invention will be apparent from the following description and from the claims.

DETAILED DESCRIPTION

The drawings are first briefly described.

BRIEF DESCRIPTION OF THE DRAWINGS

Drawings

FIGS. 6A–D: (A) is a schematic diagram depicting Ikaros F5 and F6 domains involved in protein-protein interactions. (B) Two hybrid assay was used to investigate protein-protein interactions between Ikaros isoforms. (C–D) The ability of Ikaros isoforms to interact with each other was investigated in 293T epithelial cell line.

FIG. 11A is a cytofluorometric analysis depicting T cell development in the postnatal Ikaros C−/− thymus. Cytofluorometric analyses of 5 day and 3 week old animals is shown. Five days after birth, Ikaros C−/− thymuses contain 100–300 fold fewer thymocytes than age matched wild type thymuses. An increase in the proportion of CD4 single positive thymocytes is detected even at this early stage in thymocyte development (top panel). The increase in the proportion of CD4 single positive thymocytes persists in the adult C−/−thymus in which the total number of thymocytes has reached nearly normal levels (middle panel). Single positive CD4 and CD8 thymocytes are exported to the spleen (bottom panel). Thymocyte and splenic populations were stained with FITC and PE conjugated isotype control antibodies, or anti-CD4$^{PE}$ and anti-CD8.$^{FITC}$ Positively stained populations are boxed and percentages are indicated.

FIGS. 12A–C is a depiction selective defects in the development of $_γδ$ T cells in Ikaros C−/− mice. Thymocyte (A) and splenic populations (B) depleted of CD4+ and CD8+ cells, and lineage cells respectively, were analyzed for their $_γδ$ T cell content. $_γδ$ T cells were detected in the thymus of mutant mice but at significantly reduced levels. They were not present in the spleen in any appreciable number. Intestinal intraepithelial lymphocytes (C) were analyzed for their αβ and $_γδ$ T cell composition. The great majority of Ikaros C−/− IELs were αβ T cells. No appreciable numbers of $_γδ$ T cells were present.

Figure 1:
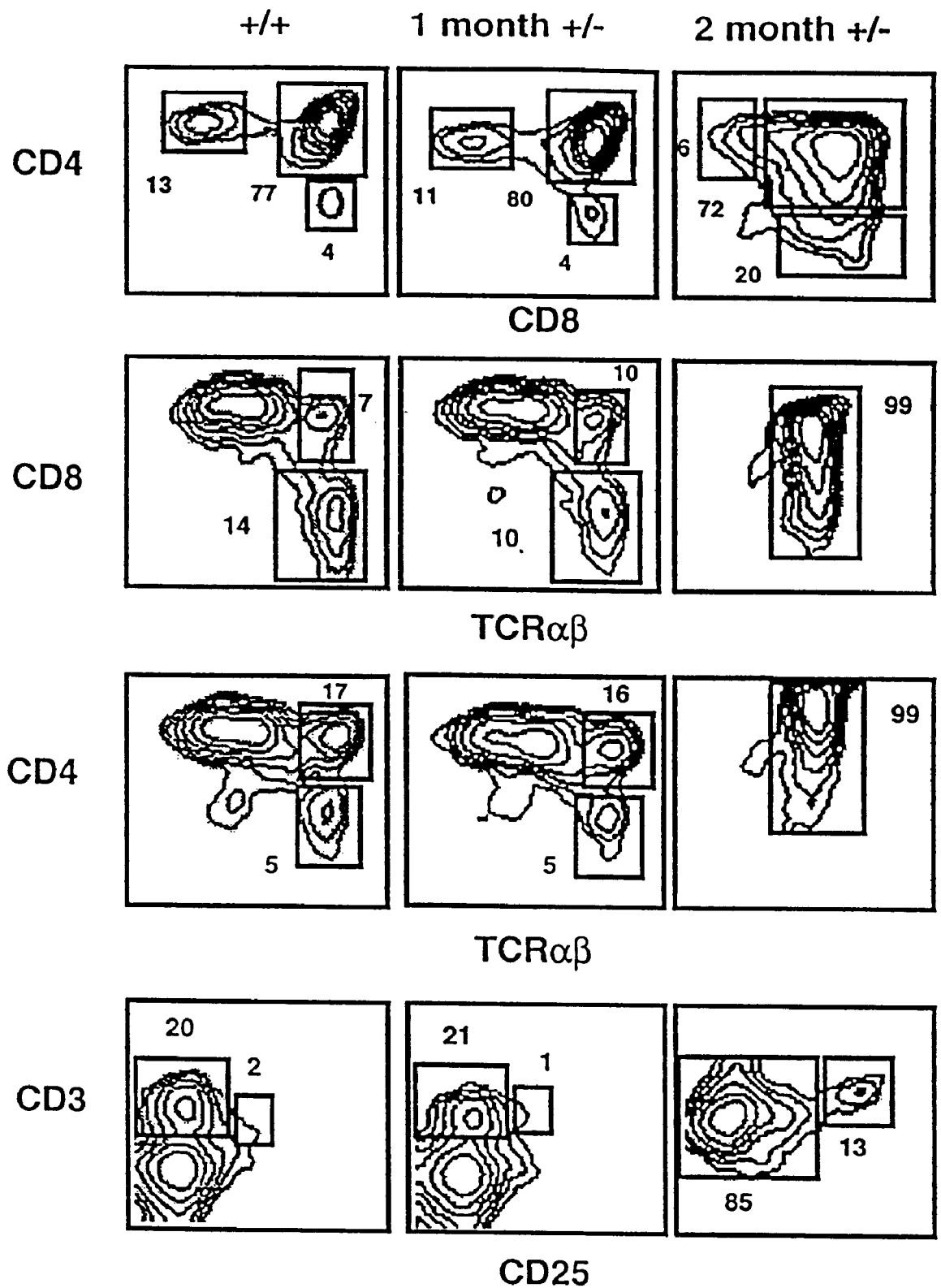
FIG. 1 is a depiction of thymocyte profiles of Ikaros heterozygous mice at 1 and 2 months of age. Thymocytes from Ikaros heterozygous (+/−) and wild-type control (+/+) mice were stained with the following combinations of monoclonal antibodies: anti-CD4$^{PE}$/anti-CD8$^{FITC}$, anti-CD8$^{PE}$/anti-TCRab$^{FITC}$, anti-CD4$^{PE}$/anti-TCRab$^{FITC}$, and anti-CD3$^{PE}$/anti-CD25$^{FITC}$. Percentages of cells which fall into each boxed positive population are indicated.

Ikaros: A Master Regulator of Hemopoietic Differentiation

In the appropriate microenvironment a hemopoietic stem cell will commit and differentiate into one of many cell lineages. Signal transduction molecules and transcription factors operating at distinct check points in this developmental pathway specify the cell fate of early progenitor cells. Such molecules act as master regulators in development and can also serve as markers for the relatively poorly defined stages of early hemopoiesis.

The Ikaros gene encodes, by means of differential splicing, at least six lymphoid restricted zinc finger proteins that are differentially expressed in the developing hemolymphopoietic system of mice and humans (Georgopoulos et al.(1992) Science 258:808–812; Molnar and Georgopoulos (1994) Mol. Cell Biol. 14:8292–8303). The Ikaros isoforms differ in their N-terminal zinc finger composition and in their overall DNA binding and transcriptional activation properties. Four of the Ikaros proteins, which contain from two to four zinc finger modules at their N-terminal region, bind DNA differentially and display distinct transcriptional activation and nuclear localization properties (Molnar and Georgopoulos (1994) Mol. Cell Biol. 14:8292–8303). The two Ikaros proteins with less than two N-terminal zinc fingers cannot bind DNA with high affinity and do not activate transcription (Molnar and Georgopoulos (1994) Mol. Cell Biol. 14:8292–8303). All of the Ikaros isoforms share two C-terminal zinc fingers that mediate their self association. The twenty homo- and heteromeric complexes that can form between the Ikaros isoforms should differ in their DNA binding and transcriptional activation properties. This is consistent with a gene which regulates multiple layers of gene expression in developing lymphocytes.

In the early embryo, the Ikaros gene is expressed in the hemopoietic liver but from mid to late gestation becomes restricted to the thymus. The only other embryonic site with Ikaros mRNA is a small area in the corpus striatum. In the adult, the Ikaros mRNA is detected only in the thymus and in the spleen (Georgopoulos et al. (1992) Science 258:808–812). The Ikaros gene functions as a transcriptional enhancer when ectopically expressed in non lymphoid cells.

The Ikaros gene plays an important role in early lymphocyte and T cell differentiation. The Ikaros gene is abundantly expressed at early embryonic hemopoietic sites is later on restricted in the developing thymus. The thymus together with the spleen are the prime sites of expression in the adult. This highly enriched expression of the Ikaros gene was also found in early and mature primary T cells and cell lines. This restricted pattern of expression of the Ikaros gene at sites where embryonic and adult T cell progenitors originate together with the ability of the encoded protein to activate transcription from the regulatory domain of an early T cell differentiation antigen supported a determining role in T cell specification.

The differential expression of the Ikaros isoforms during T cell ontogeny, their overlapping but also unique binding specificities and their diverse transcriptional potential are involved in the orderly activation of stage specific T cell differentiation markers. Multiple layers of gene expression in developing lymphocytes are under the control of these Ikaros proteins. Synergistic interactions and/or competition between members of the Ikaros family and other transcription factors in these cells on qualitatively similar and distinct target sites dictates the complex and ever changing gene expression in the differentiating and activated lymphocyte. This functional dissection of the Ikaros gene strongly suggest it functions as a master gene in lymphocytes, and an important genetic switch for early hemopoiesis and both B and T cell development.

It has been recently shown that the Ikaros gene, which is abundantly expressed during early fetal hemopoiesis and prior to the appearance of identifiable lymphoid progenitors, is essential for development of the lymphopoietic system in the mouse (Georgopoulos et al. (1992) Science 258:808–812 and Georgopoulos et al. (1994) Cell 78:143–156). Mice homozygous for a mutation in the Ikaros DNA binding domain lack not only mature T and B lymphocytes and natural killer (NK) cells, but also their earliest identifiable progenitors (Georgopoulos et al. (1994) Cell 78:143–156). The complete absence of defined lymphoid progenitors in these Ikaros mutant mice confirm a crucial role for Ikaros at very early stages of development of the murine lymphopoietic system.

The Ikaros gene maps to the proximal arm of human chromosome 7 between p11.2 and p13 next to Erbb In the mouse the Ikaros gene maps to the proximal arm of chromosome 11 tightly linked to Erbb. Other genes linked to the Ikaros locus in the mouse are the Leukemia inhibitory factor (Lif) and the oncogene Rel a member of the NFK-B family. All three of the genes linked to the Ikaros gene in the mouse appear to play an important role in the development of the hemopoietic system. The tight linkage between the Erbb and the Ikaros genes on syntenic loci in the mouse and human may be related to their genetic structure and regulation. Nevertheless, no known mutations were mapped to the Ikaros locus in the mouse. However, this does not preclude the importance of the Ikaros gene for the lymphopoietic system. Naturally occurring mutations that affect development of the immune system may not be readily obtained in mice since such mutant animals may only thrive under special care conditions.

The Ikaros gene is not only required for the first step(s) in lymphoid lineage specification, but is also a necessary factor during later stages of T cell maturation. Mice heterozygous for an Ikaros mutation, which exhibit normal lymphocyte cell surface antigen phenotypes during the first month of their lives, undergo dramatic changes in their T cell populations shortly afterwards. A general lymphoproliferation is detected in the thymus and periphery. This proliferation is followed by the development of T cell leukemia/lymphomas. Clonal expansion of T lymphocytes is first detected in the thymus, implicating maturing thymocytes as the target population for neoplastic transformation. These malignant thymocyte clones, which replace cell populations in all lymphoid tissues and infiltrate all major organs, have lost the single Ikaros wild type allele. The onset and progression of the lymphoproliferative disease in the Ikaros mutant mice may be secondary to T cell receptor ligation events that take place in the thymus and/or the periphery. In support of this hypothesis, heterozygous thymocyte populations from one month old animals, which appear phenotypically normal by flow cytometry, undergo augmented T cell receptor mediated proliferative responses in vitro and peripheral T cells are autoproliferative.

Taken together, these observations clearly demonstrate that the Ikaros gene is not only a regulator of lymphoid lineage specification but also controls T cell proliferative responses and homeostasis. Progressive loss of Ikaros in the T lineage may be coincidental with progressive loss of growth control and malignant transformation of maturing thymocytes.

Figure 4:
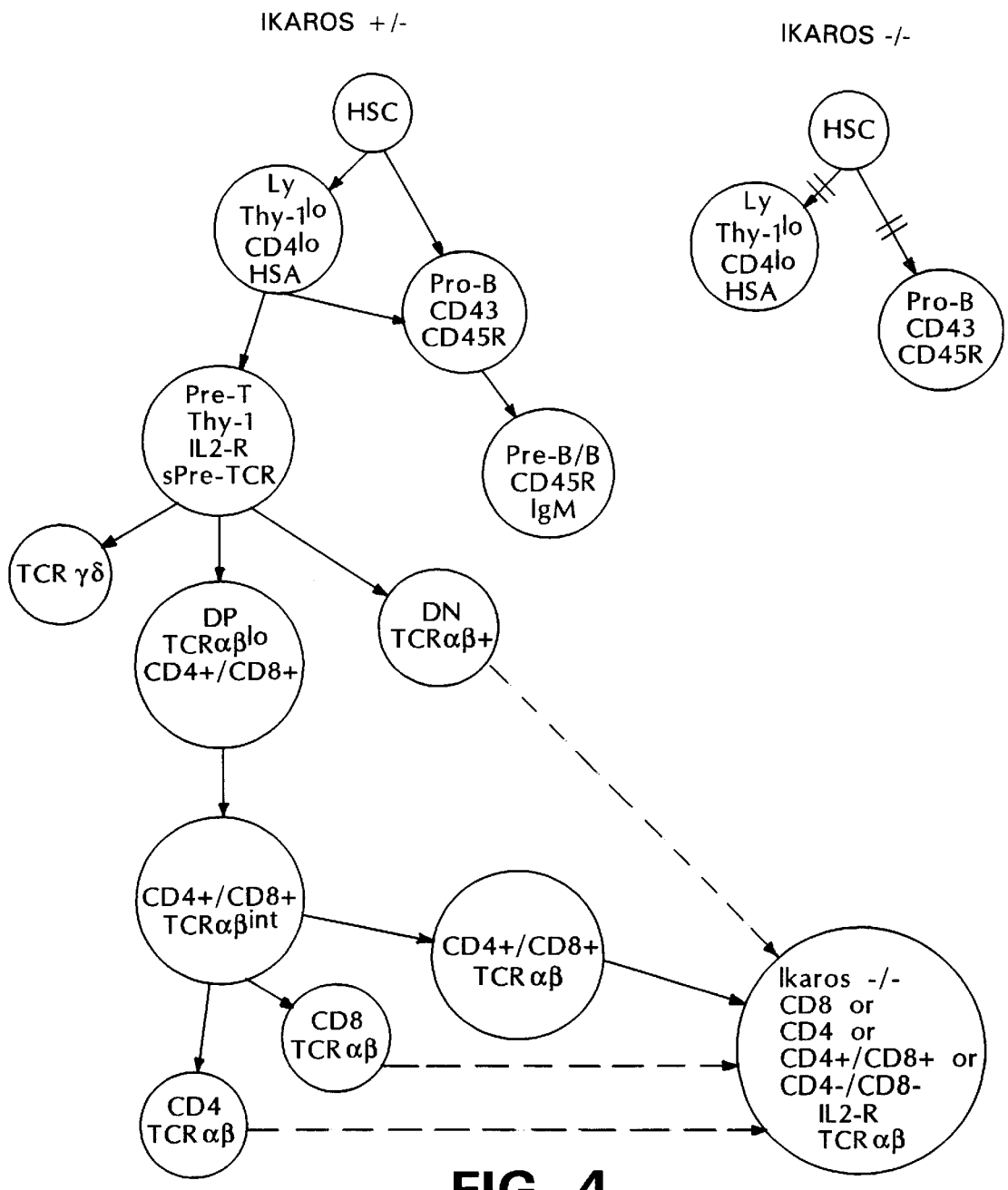
FIG. 4 is a schematic diagram depicting the effect of the Ikaros loss of function on hemolymphopoiesis. A distinct role in lymphoid lineage specification and in T cell homeostasis is revealed.

The experiments described herein show that the Ikaros gene is therefore required for both early and late events in lymphocyte differentiation (FIG. 4). Loss of Ikaros activity at different stages of this developmental process has dramatically different effects. Lack of Ikaros activity in an early hemopoietic progenitor prevents its commitment to the lymphoid lineage (FIG. 4). In sharp contrast, loss of Ikaros activity at the late stages of T cell maturation strongly correlates with T cell transformation (FIG. 4). In addition, thymocytes and mature T cells heterozygous for this Ikaros mutation are not functionally normal. Thymocytes display augmented TCR mediated proliferative responses and peripheral T cells are autoproliferative. Excessive lymphoproliferation in these lymphocyte populations may increase the number of cells available to undergo leukemic transformation by loss of the second Ikaros wild type allele. However, the results show that loss of Ikaros heterozygosity and malignant transformation are events that take place in the thymus, not in the periphery, suggesting that the Ikaros mutation has qualitatively different effects on the growth of immature thymocytes versus mature peripheral T cells.

Distinct thresholds of Ikaros activity may be required at different stages of lymphocyte development. A higher threshold of Ikaros activity, compared to that required in mature lymphocytes, may be essential for the regulated proliferation of developing thymocytes. This hypothesis is consistent with the higher levels of Ikaros mRNAs detected in maturing thymocytes relative to peripheral T and B cells in both mouse and human. It has been recently shown that the C-terminal zinc fingers in the Ikaros proteins mediate their self association and modulate their DNA binding and transcriptional activation potential. Proteins generated from the Ikaros mutant allele may, therefore, act in a dominant negative fashion by sequestering wild type isoforms in heterodimers with altered DNA binding properties. Complex formation between wild type and mutant Ikaros proteins interferes with the ability of the former to activate transcription. Due to the formation of wild type-mutant Ikaros complexes in heterozygous lymphocytes, the concentration of Ikaros wild type complexes is expected to decrease to one fourth that present in wild type cells. Such a profound decrease in Ikaros wild type complexes does not interfere with lymphocyte development but may dramatically affect lymphocyte homeostasis. Significantly, the appearance of malignant T cell clones among the Ikaros heterozygous thymocytes strongly correlates with loss of Ikaros heterozygosity and could be interpreted either as a result of complete loss of Ikaros DNA binding activity or a gain of function attributed to the mutant Ikaros proteins.

The wild type Ikaros allele encodes splicing variants that structurally resemble the mutant proteins in that they lack the N-terminal DNA binding domain (Ik-5 and Ik-6). These variants are expressed at very low levels in wild type lymphocytes. Short Ikaros isoforms may interact with factors which regulate control of proliferative responses in developing thymocytes and mature T cells. Deregulated expression of these normally expressed proteins may result in a phenotype similar to that observed in the heterozygotes, T cell hyperproliferation and malignant transformation.

From these studies on Ikaros heterozygous mice, it can be concluded that the Ikaros gene is an essential regulator for both lymphoid lineage specification and subsequent proliferation and differentiation in the T lineage. Lack of Ikaros activity at the late stages of thymocyte maturation leads to uncontrolled lymphoproliferation and to the rapid development of malignant T cell leukemia/lymphoma.

Lymphocyte Populations in Ikaros Heterozygous Mice

A targeted deletion in the Ikaros DNA binding domain leads to an early arrest in lymphocyte development in mice homozygous for the mutation. Mice heterozygous for this Ikaros mutation display initially normal lymphocyte profiles. Therefore, lack of one wild type and the presence of one mutant Ikaros allele does not prevent early development in the T and B cell lineages.

Mice heterozygous for the Ikaros DNA binding mutation display normal cell surface phenotype in thymus and spleen populations for the first month of their lives (FIG. 1). The numbers of single ($CD4^+CD8^-$ and $CD8^+CD4^-$) and double ($CD4^+/CD8^+$) positive thymocytes as well as mature splenic T cells ($CD4^+/TCRab^+$ and $CD8^+/TCRab^+$) and B cells ($CD45R^+/IgM^+$) are similar to those of their wild type siblings. Furthermore, the levels of expression of T and B cell differentiation antigens (CD4, CD8, CD3, CD25, TCRab, CD45R and IgM) are normal. Bone marrow populations also appear normal in one month old heterozygotes.

However, between the second and third month of age, changes are detected within the thymic compartment. Cell intermediates between the single and double positive stage (CD4$^+$/CD8$^{lo}$ and CD4$^{lo}$/CD8$^+$) accumulate, and thymocyte populations lose their discrete single and double positive profiles (FIG. 1). The great majority of these double positive heterozygous thymocytes express intermediate levels of the TCR complex. In the wild type thymus, 40% of the double positive population expresses low levels of the TCR complex, which becomes upregulated during the process of selection (Chan et al.(1993) *Cell* 73:225–236). The phenotypically similar triple positive thymocytes which accumulate in the heterozygous thymuses may be derived from the same stage of development as transitional stage intermediates in the wild type thymus. A two- to five-fold increase in the number of splenocytes was also observed in the two to three month old heterozygotes. In all cases, this was due to a polyclonal expansion of T lymphocytes in the spleen. In some animals, a slight increase (less than 2- fold) in the number of B lymphocytes was also observed (data not shown).

The above described experiments were performed essentially as follows. Ikaros heterozygote mutant mice were analyzed in parallel with age matched wild-type controls. Animals were studied on mixed background (129SV× C57BL/6 and on 129SV×BALB/c). Lymphocytes from the thymus, spleen, lymph nodes and bone marrow were prepared as described previously (Georgopoulos et al. (1994) *Cell* 78:143–156). Cells were washed twice in complete media (RPMI 1640 supplemented with 10% fetal calf serum, 2 mM L-glutamine, 5×10$^{-5}$ M b-mercaptoethanol and 50 mg/ml gentamicin), counted and resuspended at approximately 0.5–1×10$^6$ cells/30 ml. Cells were aliquoted into 96 well plates (30 ml/well) and blocked with an equal volume of a 1:20 dilution of normal rat serum in PBS for 30 minutes on ice followed by incubation with phycoerythrin- (PE-) and fluorescein isothiocyanate- (FITC-) conjugated monoclonal antibodies for 30 minutes. Cells were then washed 3 times, fixed (1% paraformaldehyde, 0.5% BSA, and 0.05% sodium azide in PBS) and stored at 4° C. One- and two-color flow cytometric analyses were performed on a FACScan (Becton-Dickinson, San Jose, Calif.). Isotype matched control antibodies were used as negative controls. Five to ten thousand cells were analyzed for each sample. The following antibodies (in parentheses) to lineage specific differentiation antigens were used (antibodies were obtained from PharMingen unless otherwise indicated): erythroid (TER-119), Mac-1(M1/70.15, Caltag), Gr-1(RB6-8C5), CD45R (RA3-6B2), IgM (R6-60.2), CD8 (53-6.7 and 53-5.8), CD3-e (145-2C11), CD4 (RM4-4), CD25 (7D4), TCRab (H57-597), Vb2 (B20.6), Vb3 (KJ-25), Vb5.1,5.2 (MR9-4), Vb6 (RR4-7), Vb8.1,8.2 (MR5-2), Vb9 (MR10-2), Vb10 (B21.5), Vb11 (RR3-15), Vb12 (MR11-1), Vb13 (MR12-3), Vb14 (14-2) and Vb17a (KJ-23).

Proliferative Responses of Thymocyte and Peripheral T Cells in Ikaros Heterozvgous Mice Phenotypically normal thymocyte populations in Ikaros heterozygous mice exhibit strong T cell receptor mediated proliferative responses. In sharp contrast, thymocytes from wild type mice respond weakly when triggered in this way. Since levels of expression of the TCR and co-receptor complexes appear to be similar between healthy Ikaros heterozygous and wild type thymocytes, signaling downstream of the TCR complex must be deregulated in these cells. Temporal engagement of the TCR complex is necessary to drive thymocytes through distinct stages in differentiation (reviewed by Anderson and Perlmutter, 1995). Engagement of the pre-TCR complex on CD4$^-$/CD8$^-$ double negative thymocytes mediates their clonal expansion and differentiation to the CD4$^+$/CD8$^+$ double positive stage. In contrast, differential crosslinking of the TCR complex on the surface of a double positive thymocyte mediates either cell death by apoptosis (negative selection) or maturation to the single positive stage without expansion (positive selection). Which fate awaits a triggered thymocyte, survival or death, may depend on signals transduced through different effector molecules. Signaling pathways similar to those that operate during activation of a mature T cell may mediate this process. Deregulated expression or activity of signaling molecules may underlie the augmented proliferative responses of Ikaros heterozygous thymocytes.

Changes in thymocyte populations are detected prior to any change in expression of lymphocyte cell surface antigens in the periphery. Intermediate double positive cells expressing the TCR complex (CD4$^+$/CD8$^{lo}$/TCR$^{int}$ and CD8$^+$/CD4$^{lo}$/TCR$^{int}$) become the predominant populations. Intermediate thymocyte populations, present in small numbers in the wild type thymus, are considered to be cells in transition to the single positive stage and in the process of selection. During normal maturation of double positive thymocytes, upregulation of the TCR complex with concomitant downregulation of one of its co-receptors takes place. Cells with inappropriate TCR expression are destined to die by apoptosis. Deregulation of the process that controls transition from the double to the single positive stage, may lead to the accumulation of double positive thymocyte intermediates in Ikaros heterozygous mice. Additional genetic events (i.e. loss of the second Ikaros allele) in this cell population may lead to their transformation.

Peripheral T cells in one month old Ikaros heterozygous mice also display aberrant proliferative properties. Splenic T cells autoproliferate when cultured in vitro, and, when stimulated through the TCR complex, display higher levels of $^3$H-thymidine incorporation than wild type control cells. This may result from an accumulation of autoimmune T cells in the periphery due to a breakdown in the thymic selection process. Aberrant proliferation of nontransformed heterozygous peripheral T cells, together with a potential impairment in the death pathways that mediate elimination of activated T cells, may account for the moderate increase in size of the spleen frequently detected in the two to three month old heterozygotes. This polyclonal T cell proliferation precedes the clonal expansion of malignant T lymphocytes responsible for the massive size increase of the spleen in the older heterozygous mice.

The proliferative responses of Ikaros heterozygous thymocytes and peripheral T cells discussed above were determined prior to the first changes in thymocyte profiles. Thymocytes and splenocytes from one month old Ikaros heterozygotes and wild type controls were plated at different concentrations in wells coated with an antibody raised to the constant region of the b chain of the TCR complex.

After 48 hrs of TCR stimulation, heterozygous thymocytes displayed a dramatic increase in $^3$H-thymidine incorporation, a measure of proliferative response, relative to background (hIgG) (Table 1A). An average 200 fold increase in $^3$H-thymidine incorporation was detected. In sharp contrast, under the same conditions, wild type thymocytes displayed low proliferative responses (an average 7.7 fold increase in $^3$H-thymidine incorporation over background) (Table 1A).

Heterozygous splenocytes proliferated in the absence of TCR stimulation (hIgG). $^3$H-thymidine incorporation was an average 2.6 fold greater than observed with wild type control splenocytes (Table 1B). Upon TCR stimulation, heterozygous splenocytes also incorporated higher levels of $^3$H-thymidine than wild type controls (Table 1B). Given, however, the higher background proliferation of heterozygous splenocytes, their average stimulation index was similar to wild type. An average 27 and 35 fold increase in $^3$H-thymidine incorporation relative to background was detected with wild type and heterozygote splenocytes, respectively (Table 1B). These differences in proliferative responses of heterozygous and wild type splenic T cells cannot be accounted for by differences in the absolute numbers of T cells in these organs which, on average, were similar.

To determine whether the abnormal proliferative response to TCR stimulation observed in the 1 month thymus was a property of the maturing double positive population, we tested fetal day 17.5 thymocytes. At this stage in fetal development, thymocytes exist as a homogeneous double positive population with no detectable single positive cells. These double positive fetal thymocytes are in the process of completing TCR rearrangements and a subfraction of these cells, approximately 10% as determined by flow cytometry (data not shown), express low levels of TCR ab. Heterozygous fetal thymocytes also displayed higher levels of $^3$H-thymidine incorporation relative to thymocytes from their wild type siblings (Table 1C). However, the magnitude of the proliferative response of heterozygous fetal thymocytes was less dramatic than that observed with the 1 month old heterozygous thymocytes, perhaps due to the lower percentage of TCR positive cells in the day 17.5 fetal thymus.

shown with each value representing the mean of triplicate cultures. Number of cells per culture ranged between 2–4× $10^5$. For (C), results from a single experiment are shown with each value representing the mean of duplicate cultures with $10^5$ cells/culture. Fold stimulation over background= $^3$H-thymidine incorporated in response to plate-bound anti-TCRab/$^3$H-thymidine incorporated in response to hamster IgG isotype control.

The above described experiments were performed essentially as follows. Flat-bottomed 96-well microtiter plates were coated with 20 mg/ml anti-TCR ab monoclonal antibody (H57-597, Pharmingen) or hamster IgG isotype control antibody (Pharmingen) overnight at 4° C. Organs were removed aseptically from Ikaros heterozygotes and wild-type age matched control animals and single cell suspensions made as described above. Cells were plated at two different cell concentrations (0.5–4×$10^5$ cells/well) in triplicate in RPMI 1640 supplemented with 10% fetal calf serum, 2 mM L-glutamine, 5×$10^{-5}$ M b-mercaptoethanol and 50 mg/ml gentamicin. For embryo studies, $10^5$ cells/well were plated in duplicate. After 48 hours, cells were fed and then pulsed for 6–12 hours with 2 mCi/well $^3$H-methyl thymidine. Cells were then transferred to a filter using an automatic cell harvester (Harvester 96, Tom Tec) and counted on the 1205 Betaplate Scintillation Counter (Wallace).

Leukemia/lymphoma Invariably Develops in Ikaros Heterozygous Mice

Between three and six months of age, 100% of Ikaros heterozygous mice examined developed fatal leukemia/lymphoma. Malignant lymphoblastic T cell clones replace the normal cells in lymphoid tissues. However, outgrowth of clonal T cell populations is first detected in the thymus, in

TABLE 1

| Experiment No. | +/+ animals | | fold stimulation | +/− animals | | fold stimulation |
|---|---|---|---|---|---|---|
| | hIgG | anti-TCR | hIgG/αTCR | hIgG | anti-TCR | hIgG/αTCR |
| A. THYMOCYTES | | | | | | |
| 1 | 1236 | 7400 | 6.2 | 1311 | 40,000 | 30.5 |
| 2 | 1200 | 4000 | 3.3 | 2000 | 790,000 | 395 |
| 3 | 2300 | 2200 | 0.95 | 3000 | 280,000 | 93 |
| 4 | 2000 | 4100 | 2.1 | 1200 | 170,000 | 142 |
| 5 | 950 | 25,000 | 26 | 1100 | 380,000 | 345 |
| B. SPLENOCYTES | | | | | | |
| 1 | 3500 | 23,500 | 6.7 | 20,000 | 90,000 | 4.5 |
| 2 | 7500 | 314,500 | 42 | 17,400 | 623,000 | 36 |
| 3 | 8300 | 325,500 | 39 | 7000 | 752,000 | 107 |
| 4 | 3100 | 134,000 | 43 | 13,350 | 156,500 | 12 |
| 5 | 14,000 | 64,000 | 4.5 | 38,000 | 614,000 | 16 |
| C. EMBRYONIC THYMOCYTES | | | | | | |
| 1 | 3200 | 9800 | 3.1 | 4300 | 58,400 | 13.6 |
| 2 | 3600 | 22,000 | 6.1 | 3100 | 101,000 | 32.6 |
| 3 | 8400 | 35,000 | 4.2 | 3000 | 100,500 | 33.5 |
| 4 | 12,800 | 61,000 | 4.8 | 6200 | 77,000 | 12.4 |

Proliferative activity of thymocytes (A) and splenocytes (B) from 1 month old Ikaros heterozgote (+/−) and wild type (+/+) mice as well as day 17.5 embryonic thymocytes (C) as represented by counts per minute (cpm) $^3$H-thymidine incorporated in response to plate-bound anti-TCRab or hamster IgG isotype control antibody (considered background). For (A) and (B), results of five independent experiments are support of the hypothesis that the targets for transformation are thymocytes undergoing inappropriate proliferative responses during their transition from the double to the single positive stage. Although all of the aberrant T cell clones express the CD3/TCRab complex, distinct TCR specificities emerge in different animals suggesting that the transformation event is stochastic. The CD25 (IL-2 receptor a chain) activation marker is also expressed on these lymphoblastic T cells, but the percentage varies between animals and is highest in later stages of the disease as defined by a complete take-over of lymphoid organs by clonal lymphoblastic T cells. Expression of the CD25 activation marker on the surface of these cells suggests that perhaps an autocrine pathway has been activated in these cells which supports their autonomous growth reported in some cases of human leukemia. The autonomous growth and tumorigenic properties of these malignant T cells were confirmed by adoptive transfer. Lymphoid tumors containing cells with the same cell surface phenotype and genetic make-up as the input cells were formed shortly after transfer into nude mice.

Genetic analysis of the T cell lymphomas/leukemias in the Ikaros heterozygous mice revealed loss of the wild type Ikaros allele in these cells. Karyotypic analysis displayed a normal complement of chromosomes. Therefore, the loss of the wild type Ikaros allele is due to illegitimate mitotic segregation of two mutant chromatids, to a gene conversion event, or to a deletion of the Ikaros gene. In any of these cases, loss of the wild type Ikaros allele may be directly linked to the malignant transformation of heterozygous thymocytes. Alternatively, loss of Ikaros heterozygocity may confer a growth advantage to these cells which may undergo additional genetic events before they transform. Loss of heterozygosity in cells with mutations in the p53 and retinoblastoma tumour suppressor genes is also coincidental with their progression to a tumorigenic state.

Soon after three months of age, 100% of the Ikaros heterozygous mice examined developed visible lymphadenopathy. Cervical, axial and mesenteric lymph nodes are grossly enlarged to 20–50 times the normal size. In addition, these mice develop splenomegaly. There is an average ten-fold increase in the number of splenocytes and the spleen appears as the predominant organ in the abdominal cavity. The thymus is also enlarged and shows loss of its distinctive bilobed morphology. Histological examination of these lymphoid organs revealed obliteration of the normal architecture caused by accumulation of a uniform population of large lymphoblastic lymphocytes). Complete effacement of the cortical-medullary structures is observed in the thymus. Increase in the white pulp and decrease in the red pulp areas of the spleen were consistently observed. B lymphoid follicles as well as and cortical and medullary regions were absent in the lymph nodes. Large numbers of circulating lymphocytes were also seen in the peripheral blood of these animals. These cells were lymphoblastic in appearance, having large nuclei with fine chromatin structure, prominent nucleoli and scanty cytoplasm.

Non-lymphoid organs in the affected Ikaros heterozygous mice were also extensively infiltrated by lymphoblastic cells. Liver and kidneys in Ikaros heterozygous mice with a lymphoproliferative syndrome were pale and enlarged in size. Histological examination of liver, kidney and lung sections revealed complete effacement of their normal tissue architecture by accumulating numbers of lymphoblastic cells. Extensive invasion by these lymphocytes was evident.

The lymphoproliferative syndrome and leukemia/lymphoma occur at the same frequency in heterozygous animals derived from two independent embryonic stem (ES) cell lines carrying the same Ikaros mutation (Georgopoulos et al. (1994) *Cell* 78:143–156). Significantly, chimeric animals with moderate to high levels of Ikaros ES cell contribution also develops his disease but with an approximate two month lag period compared to the heterozygous population. Development of leukemia/lymphoma in two lines of Ikaros heterozygous mice as well as in Ikaros chimeras prove the hypothesis that the underlying mechanism is mediated by the Ikaros mutation.

The experiments were performed essentially as follows. Tissues harvested from euthanized wild type and Ikaros mutant mice were fixed in 4% buffered formalin, processed and embedded in paraffin. Sections were cut at 5 mm thickness, mounted and stained with hematoxylin and eosin. Light microscopy was performed at 20× to 600× magnification on an Olympus BMax-50 microscope.

A homogeneous Population of Mature and Activated T Cells Predominates in all Lymphoid Organs The phenotype of lymphocyte populations in affected Ikaros heterozygous mice was determined by flow cytometry. Cells obtained from thymus, lymph nodes, spleen and bone marrow of these animals were analyzed with antibodies to a number of early and late lymphocyte differentiation markers.

Figure 2A:
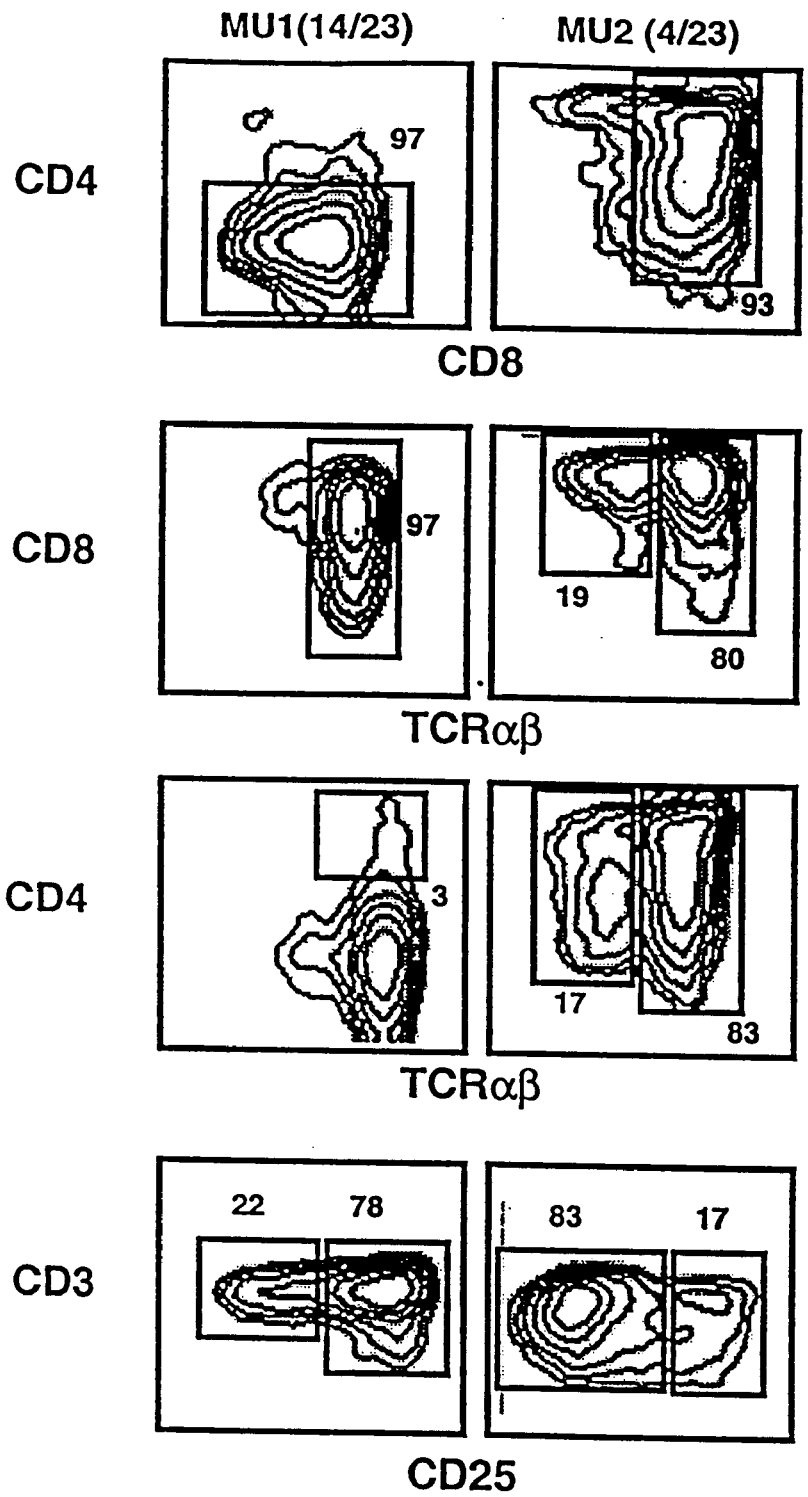
FIGS. 2A–C is a depiction of flow cytometric analysis of lymphoid organs in Ikaros heterozygotes with lymphoproliferative disorder. Profiles of thymocyte (A) and splenocyte (B) populations of two Ikaros heterozygotes displaying distinct co-receptor phenotypes (MU1, CD8$^+$CD4$^-$ and MU2, CD8$^+$CD4$^+$). Profiles of cells in bone marrow and lymph node (C) from MU1 are also shown. Cells were stained with the following combinations of monoclonal antibodies: anti-CD4$^{PE}$/anti-CD8$^{FITC}$, anti-CD8$^{PE}$/anti-TCRab$^{FITC}$, anti-CD4$^{PE}$/anti-TCRab$^{FITC}$, and anti-CD3$^{PE}$/anti-CD25$^{FITC}$. Percentages of cells which fall into each boxed positive population are indicated.
Figure 2B:
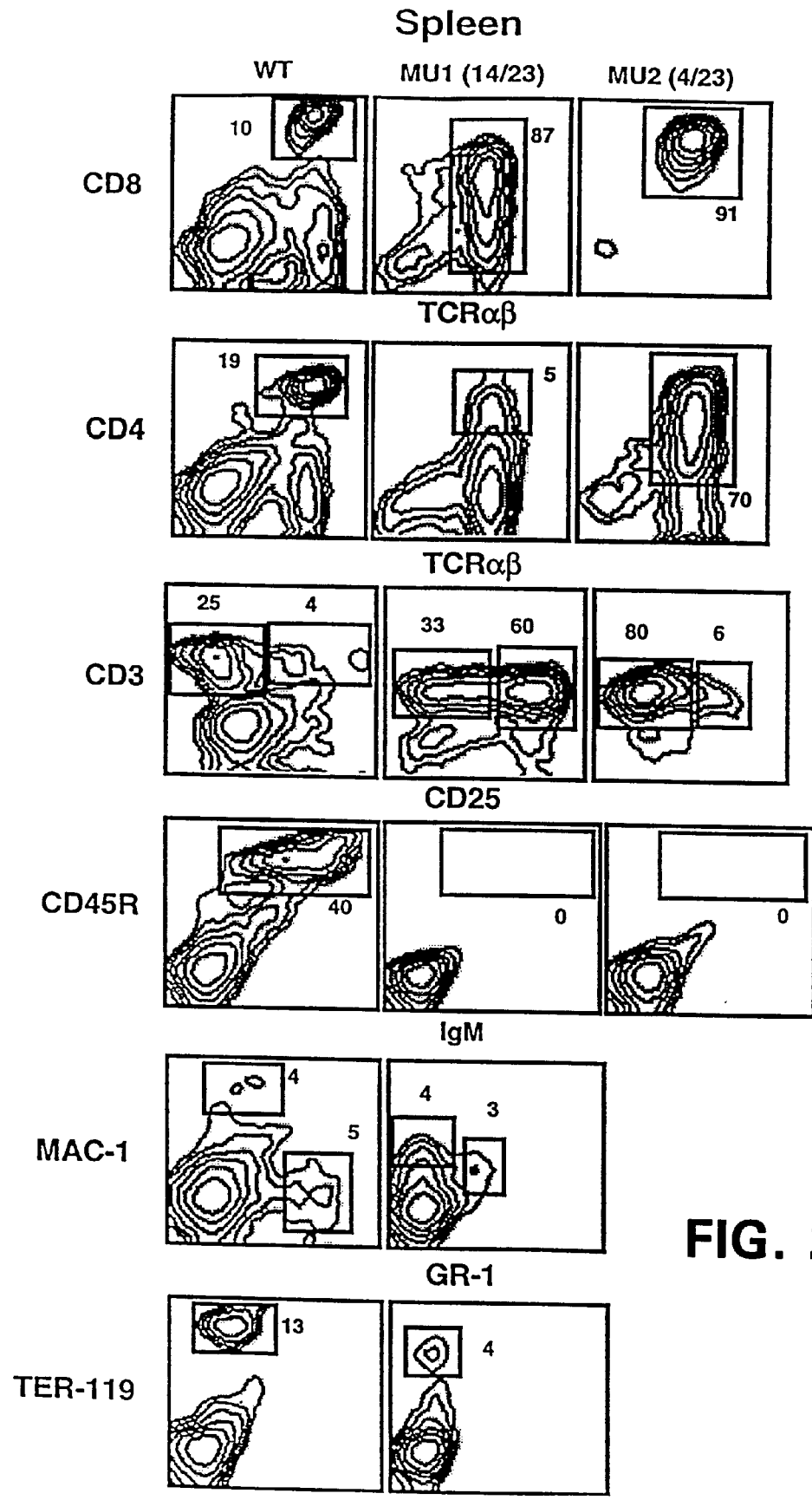
Figure 2C:
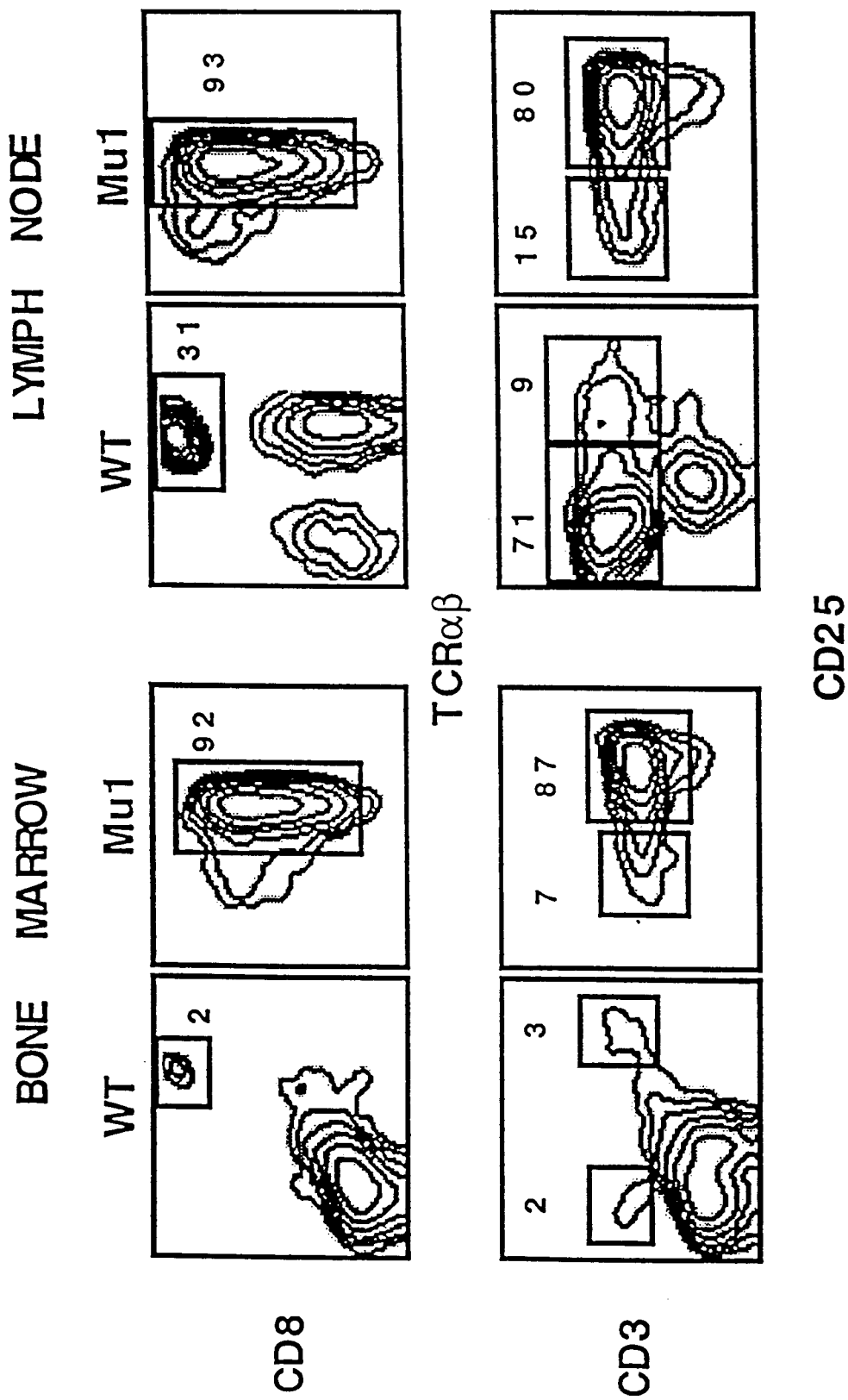

The accumulating lymphocytes in all lymphoid organs, including the bone marrow, were T cells in all animals analyzed. These T cells were large (as determined by forward scatter profiles) and expressed the CD3/TCRab complex (FIG. 2). Co-receptor composition of the accumulating T cell population was uniform within a given animal but differed between mice (FIG. 2, MU1 and MU2). $CD8^+/TCR^+$ populations arose with the highest frequency (14/23 animals), but $CD4^+/TCR^+$ (2/23 animals), $CD4^+/CD8^+/TCR^+$ (4/23 animals) and $CD4^-/CD8^-/TCR^+$ (3/23 animals) populations were also detected.

From 5%–100% of the aberrant T cell population expressed the CD25 (IL-2 receptor a chain) activation marker (FIG. 2). A higher percentage of $CD25^+$ cells within the population strongly correlated with later stages in the disease. The aberrant T cell populations could be propagated indefinitely in vitro in the presence of IL-2. In several cases, these cells grew in the absence of added growth factors.

B cell populations were not detectable in the spleen, lymph nodes or bone marrow of affected animals. A relative decrease in size of the erythroid and myeloid compartments of the spleen and bone marrow was also seen (FIG. 2B). A takeover of the lymphoid regions of these organs by the rapidly accumulating lymphoblastic T cells, at the expense of the B cell compartment, may account for these results and also correlates with the uniform histological appearance of lymphoid tissues in these mice.

The Aberrant T Cell Populations are Clonal in Nature and Arise in the Thymus

Since all of the aberrant T cell populations analyzed expressed the TCRab complex, their clonality was determined by examining their T cell receptor composition. This analysis was undertaken in two ways. The structure of the T cell receptor b chain gene was investigated by defining the Db to Jb segment rearrangements in these T cell populations (see, e.g., Anderson et al. (1992) *EMBO J* 11:4866–4877). In addition, Vb expression on the cell surface was studied by flow cytometry.

Seven Db2-Jb2 rearrangements, and one band corresponding to the germline configuration of the b chain gene, were detected in thymocytes and splenocytes from wild type and one month old Ikaros heterozygous mice. These results reflect the normally polyclonal nature of thymocyte and mature T cell populations in these organs. The differences in the Db2-Jb2 composition detected between thymus and spleen reflect differences in the residing cell populations. The increased intensity of the band corresponding to the germline configuration at the b chain locus in the spleen corresponds to the presence of non-T cell populations which are normally present in this organ. In contrast, T cell populations in older Ikaros heterozygous mice displayed one or two predominant Db2-Jb2 rearrangements which were the same in both the thymus and the spleen.

The clonality of these aberrant T cells was also investigated by determining cell surface TCR Vb expression using a panel of monoclonal antibodies specific for TCR Vb regions. In two representative cases, shown in FIG. 3, the majority of T cells were of a single Vb specificity. In one animal, 90% of the T cell population in the thymus and the spleen expressed Vb5.1, 5.2 whereas in a second animal, where only spleen cells were analyzed, 80% of the cells expressed Vb11. In a third animal, aberrant T cell populations in thymus and spleen expressed Vb3 (data not shown). Taken together, these results strongly implicate a clonal origin for these aggressively growing T cell populations.

To determine the organ in which these malignant T cell clones first arise, lymphocyte populations in two to three month old Ikaros heterozygotes, without visible manifestations of lymphoproliferation prior to dissection, were analyzed. Expansion of clonal T cell populations was again followed by studying the repertoire of Db2-Jb2 rearrangements in the thymus and spleen. Outgrowth of clonal T cell populations, manifested as a decrease in the repertoire of Db2-Jb2 rearrangements, was apparent in the thymus but not in the spleen. These results suggest a thymic origin for the malignancies.

The experiments were performed essentially as follows. DNAs were prepared from thymocytes and splenocytes as previously described (Laird et al. (1991) *Nuc. Acids Res.* 19:4293). PCR was carried out as described by Rodewald, et. al., 1994, with the following modifications. Samples were denatured (94° C., 45 sec), annealed (63° C., 45 sec) and extended (72° C., 1 min) for 35 cycles. Aliquots from each sample were electrophoresed on a 1.2% agarose Tris-Borate-EDTA gel and blotted onto a Hybond-N+ (Amersham) membrane in 0.4 M NaOH. Sequences of synthetic oligonucleotides (5' to 3') used as primers (Db2.1 and Jb2.7) and as an internal probe (DbINT) for Southern analysis are as follows:

Db2.1: GTA GGC ACC TGT GGG GAA GAA ACT (SEQ ID NO: 1)

Jb2.7: TGA GAG CTG TCT CCT ACT ATC GAT T (SEQ ID NO:2)

DbINT: ATT GTG GGG ACT GGG GGG GC (SEQ ID NO:3)

Expected PCR product for germline configuration is 1858 bp and for rearrangements of Db2.1 to either Jb2.1, Jb2.2, Jb2.3, Jb2.4, Jb2.5, Jb2.6 or Jb2.7 are between 1279 and 224 bp. All amplified PCR products hybridized with an internal oligonucleotide probe to confirm their specificity. DNAs analyzed were from the thymus and spleen of, wild type, 1 month heterozygote, three 2–3 month old heterozygotes, and four more than 3 month old heterozygotes with visible lymphoproliferative disorder. Molecular weight marker used was a 1 kb DNA Ladder (GibcoBRL).

Clonal T Cell Populations From Ikaros Heterozygous Mice Readily Form Lymphoid Tumours in Nude Mice T cells isolated from the thymus of an Ikaros heterozygote with leukemia/lymphoma were injected subcutaneously into mice of the nude/beige background. The first signs of local tumor outgrowth were seen the first week post- injection. By the third week, tumors grew to 2–3 cm in diameter. At this point, animals were sacrificed and tumors, as well as in some cases, spleen, bone marrow and lymph node populations were analyzed by flow cytometry. Cells isolated from the tumors were of the same cell surface phenotype (CD4$^-$CD8$^-$TCRab$^+$CD25$^+$) as the injected T cells, and displayed the same single Db2-Jb2 rearrangement. In addition, this same T cell population predominated in the spleen, lymph nodes and bone marrow of these nude mice. The ability of a clonal T cell population from an Ikaros heterozygote to readily form tumors upon subcutaneous injection, and to invade and replace the normal cell populations in the host's lymphoid organs, demonstrates its malignant nature.

The experiments were performed essentially as follows. Thymocytes were prepared aseptically, as described previously, from a more than 3 month old heterozygote with lymphoproliferative syndrome, and a wild type control mouse. Cells were injected subcutaneously into nude mice of the N:NIH-bg-nu-xid BR background (Charles River). Mice were divided into three groups of five animals each. One group received $2 \times 10^6$ heterozygote thymocytes, the second $6 \times 10^6$ and the third $6 \times 10^6$ wild type thymocytes. Cell surface phenotype was determined by staining with the following combinations of monoclonal antibodies: anti-CD4$^{PE}$/anti-CD8$^{FITC}$, anti-CD8$^{PE}$/anti-TCRab$^{FITC}$, anti-CD4$^{PE}$/anti-TCRab$^{FITC}$, and anti-CD3$^{PE}$/anti-CD25$^{FITC}$ as described previously.

Loss of Ikaros Heterozygosity in the Malignant T Cell Clones

The expression of Ikaros isoforms generated by the wild type and/or mutant alleles was analyzed in the lymphoid populations of the healthy and diseased heterozygous mice. RT-PCR was used to study expression of Ikaros wild type and mutant messages in the thymus and the spleen of one to three month old animals as previously described (Molnar and Georgopoulos (1994) *Mol. Cell Biol.* 14:8292–8303).

Ikaros transcripts generated from both the mutant and wild type alleles were detected in the thymus and spleen of one month old heterozygous mice. However, only transcripts derived from the Ikaros mutant allele were detected in lymphoid organs from heterozygous mice with leukemias/lymphomas and cells from a nude mouse tumor. To exclude the possibility that this result was due to preferential amplification of the shorter mutant cDNAs, we used a different set of primers which amplify only wild type cDNAs. No amplification products were detected with these primers, suggesting that wild type Ikaros messages were not expressed in these malignant T cells. Lack of wild type Ikaros transcripts was first detected in the thymuses of two to three month old heterozygotes, while the spleen and bone marrow of these mice expressed both the wild type and mutant forms. This apparent lack of thymic expression from the Ikaros wild type allele was coincidental with the accumulation of clonal T cell populations in this organ. Studies on Ikaros protein expression in these cells confirmed these results.

The experiments were performed essentially as follows. Reverse transcription PCR (RT-PCR) analysis of total RNA prepared from thymus and spleen from wild type and mutant mice was performed as previously described (Molnar and Georgopoulos (1994) *Mol. Cell Biol.* 14:8292–8303) with the following modifications. Samples were denatured (94° C., 15 seconds), annealed (60° C., 20 seconds) and extended (72° C., 30 seconds) for 35 cycles. The relative concentration of cDNAs prepared from each tissue was determined using a set of primers which would amplify GAPDH cDNA for a number of cycles within the linear range of product amplification. Adjusted amounts of cDNAs were amplified with 4 sets of primers derived from exons inside and outside the deleted region for 35 cycles. These sets of primers; Ex2F/Ex7R, Ex2F/Ex6R, Ex3F/Ex7R, Ex4F/Ex7R allow the determination of exon usage by the Ikaros transcripts. Sequences of the synthetic oligonucleotides (5' to 3') used as primers are as follows:

Ex2F: CAC TAC CTC TGG AGC ACA GCA GAA (SEQ ID NO:4)

Ex3F:AGT AAT GTT AAA GTA GAG ACT CAG (SEQ ID NO:5)

Ex4F: GGT GAA CGG CCT TTC CAG TGC (SEQ ID NO:6)

Ex6R: TCT GAG GCA TAG AGC TCT TAC (SEQ ID NO:7)

Ex7R: CAT AGG GCA TGT CTG ACA GGC ACT (SEQ ID NO:8)

RT-PCR analysis of Ikaros transcripts expressed in the lymphoid organs of Ikaros heterozygotes was also performed. Expected sizes of products are as follows: Ik-1, 750 bp; Ik-2, 490 bp; Ik-4, 365 bp; mutant Ik-1 and Ik-2; 325 bp; and mutant Ik-4, 200 bp (as described in Georgopoulos et al. (1994) Cell 78:143–156). cDNAs analysed were from thymus, spleen and bone marrow of; 1 month wild type, 1 month heterozygote, 2 month heterozygote, 3 month heterozygote, a nude mouse T cell tumor, Ikaros homozygote, and no DNA control. Cells from the thymus, spleen and bone marrow of four animals older than 3 months with visible physical manifestations of lymphoproliferative disorder were pooled.

To determine whether the Ikaros wild type allele was still intact, the structure of the Ikaros loci were studied by Southern analysis. A single 13.5 kB BamHI fragment, derived from the mutant Ikaros locus, was detected when DNAs from the thymuses of mice with leukemias/lymphomas were analyzed. This mutant genomic fragment was also predominant in DNAs prepared from the spleen of these animals. The low levels of the 18.5 kB BamHI fragment, derived from the wild type locus, detected in the spleen of these mice can be accounted for by the erythroid and myeloid cells which present a minor population in this organ. Loss of the wild type Ikaros allele was also evident in cells from a nude mouse tumor. However, in a three month old heterozygote with polyclonal thymocyte and splenocyte populations (as determined by TCR Db-Jb rearrangements), wild type and mutant Ikaros alleles were detected at similar levels in both of these lymphoid organs.

The experiments were performed essentially as follow. DNA was prepared from thymocytes and splenocytes as described above. Digestions were performed with BamHI overnight at 37° C. Samples were electrophoresed on a 0.5% agarose Tris-Borate-EDTA gel overnight at 50V and transferred to a Hybond-N+ (Amersham) membrane. Filters were probed with an 870 bp fragment consisting of intronic sequences between exons 2 and 3 of the Ikaros gene (Georgopoulos et al. (1994) Cell 78:143–156).

Analysis of Ikaros Domains

The Ikaros gene encodes a family of Zinc finger proteins with distinct DNA binding properties. A deletion in the Ikaros DNA binding domain causes an early arrest in lymphocyte development in mice homozygous for this mutation. In addition, Ikaros heterozygotes rapidly develop fatal T cell leukemias and lymphomas. Distinct Ikaros isoforms produced by the mutant and wild type alleles share at their C-terminus zinc finger motifs that mediate their stable interaction (in the absence of DNA) and dictate their subcellular localization. Homo- and hetero-dimer formation between Ikaros isoforms with an intact DNA binding domain strongly stimulates their binding affinity and transcription activation potential. In sharp contrast, interactions between Ikaros proteins without and with a DNA binding domain interferes with the ability of the latter to participate in transcription in a dominant negative fashion. Regulated expression and interactions between functionally distinct Ikaros isoforms may determine proliferation versus differentiation in the developing hemolymphopoietic system.

The Ikaros gene with restricted expression in the fetal and adult hemolymphopoietic system is essential for the development of all mouse lymphoid lineages. It encodes at least seven functionally distinct zinc finger containing proteins by means of alternate splicing (Molnar and Georgopoulos, Mol. Cell. Biol. 14:8292–8303, 1994, herein incorporated by reference). Four of these isoforms (Ik-1, Ik-2, Ik-3 and Ik-4), have two to four zinc finger motifs at their N-terminal domain and bind to sequences that share the core motif GGGA. However, their overall sequence specificity and affinity for binding DNA are distinct. In contrast to the four differentially utilized N-terminal zinc fingers, two C-terminal finger motifs not involved in high affinity DNA binding are shared by all Ikaros isoforms. Three of the Ikaros isoforms (Ik-5, Ik-6 and Ik-7) which lack essential N-terminal but not the C-terminal zinc finger motifs do not bind DNA. A targeted deletion of the two exons encoding three of the four N-terminal zinc fingers in the mouse germline resulted in an early and complete arrest in lymphocyte development. Ikaros homozygous mutant mice lack not only mature T and B lymphocytes and NK cells but also the earliest defined lymphoid progenitors. In sharp contrast, mice heterozygotes for this Ikaros mutation rapidly develop leukemia and lymphoma of a T cell phenotype. Thymocytes in one month old Ikaros heterozygotes have normal cell surface phenotype but undergo augmented in vitro lymphoproliferative responses after engagement of the T antigen receptor. Dramatic changes in thymocyte profiles between the second and third month post parturition are consistent with their in vivo stimulation via their T antigen receptor. Subsequent accumulation of malignant T cell clones in the thymus is concomitant with the loss of Ikaros heterozygocity. Therefore, the progressive loss of Ikaros activity in maturing thymocytes underlies a stepwise transition from a resting state to a proliferative and further to a transformed state. Ikaros proteins generated by the mutant allele in heterozygous thymocytes are also produced at low frequency as alternatively spliced products by the wild type allele. These Ikaros isoforms (i.e. Ik-6 and Ik-7) may dominantly interfere with the function of the proteins predominantly generated by the wild type gene (i.e. Ik-1 and Ik-2) and set the first step towards lymphocyte transformation.

Activation Domain

Figure 5A:
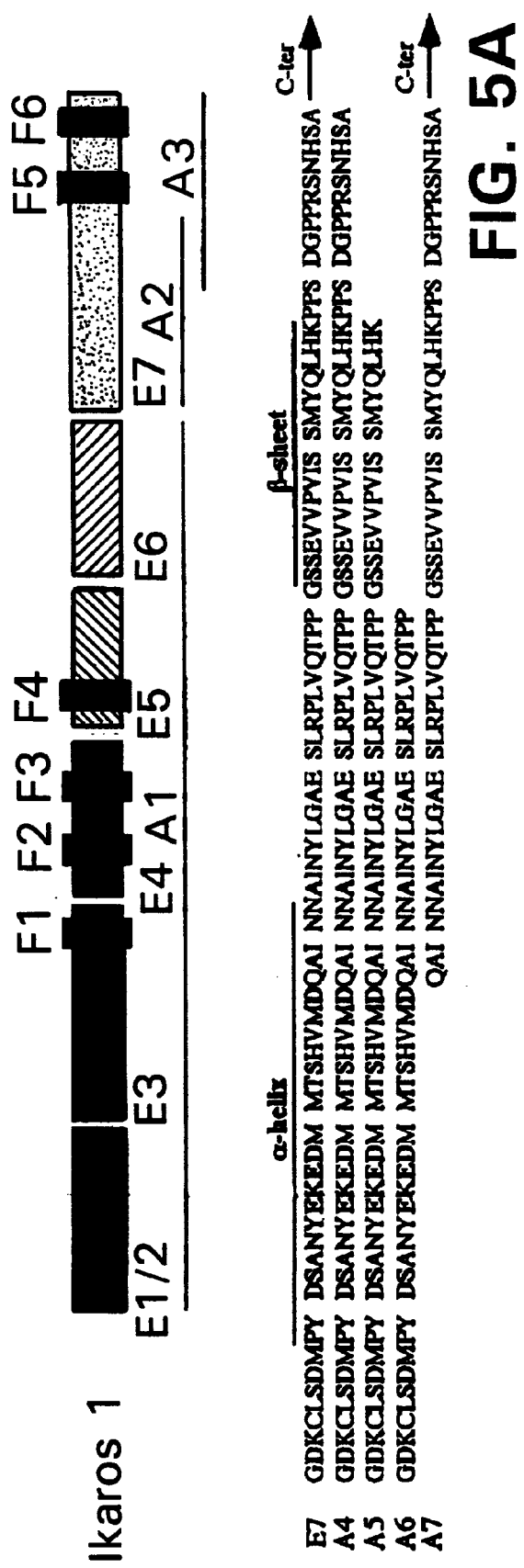
FIGS. 5A & B: (A) is a schematic diagram depicting the structure of the Ikaros gene and the activation domain shared by all Ikaros isoforms. (B) β-gal and growth assays used to map the Ikaros activation domain.
Figure 5B:
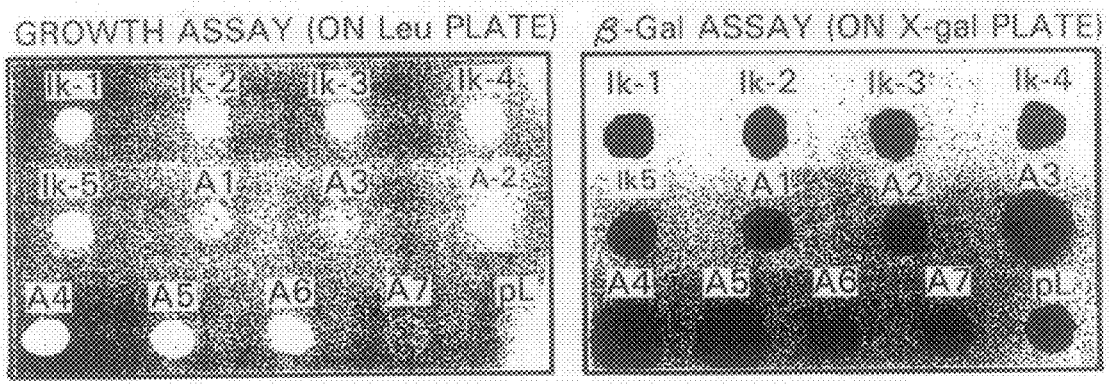

The interactions between various Ikaros isoforms and their activities were studied. Prior to the determination of a potential interaction region(s), a strong activation domain present in all of the Ikaros proteins was mapped within the first 81 amino acids of exon -7 (FIG. 5A). This domain is comprised of an acidic and a hydrophobic stretch of amino acids with propensities for an α-helix and a β-sheet structure respectively (FIG. 5A). Deletion of proline residues from the 3' of this domain did not interfere with its activity, whereas the deletion past the hydrophobic amino acids significantly reduced its potential (FIG. 5B). Removal of the 5' acidic amino acids abrogated its function altogether (FIG. 5B). All Ikaros proteins share this bipartite activation domain comprised of an essential acidic region and a required hydrophobic ammoniated region for maximum activity. However, the Ikaros proteins (Ik-1, Ik-2, Ik-3, Ik-4 and Ik-5) were weaker activators relative to their isolated bipartite activation domain but displayed similar activation potential to its acidic amino acid sub region. Ikaros protein conformation controlled by intra- and inter-molecular interactions may dictate the accessibility of this activation domain and its sub regions and consequently determine the overall transcriptional potential of these proteins.

Protein-Protein Interactions

Figure 6A:
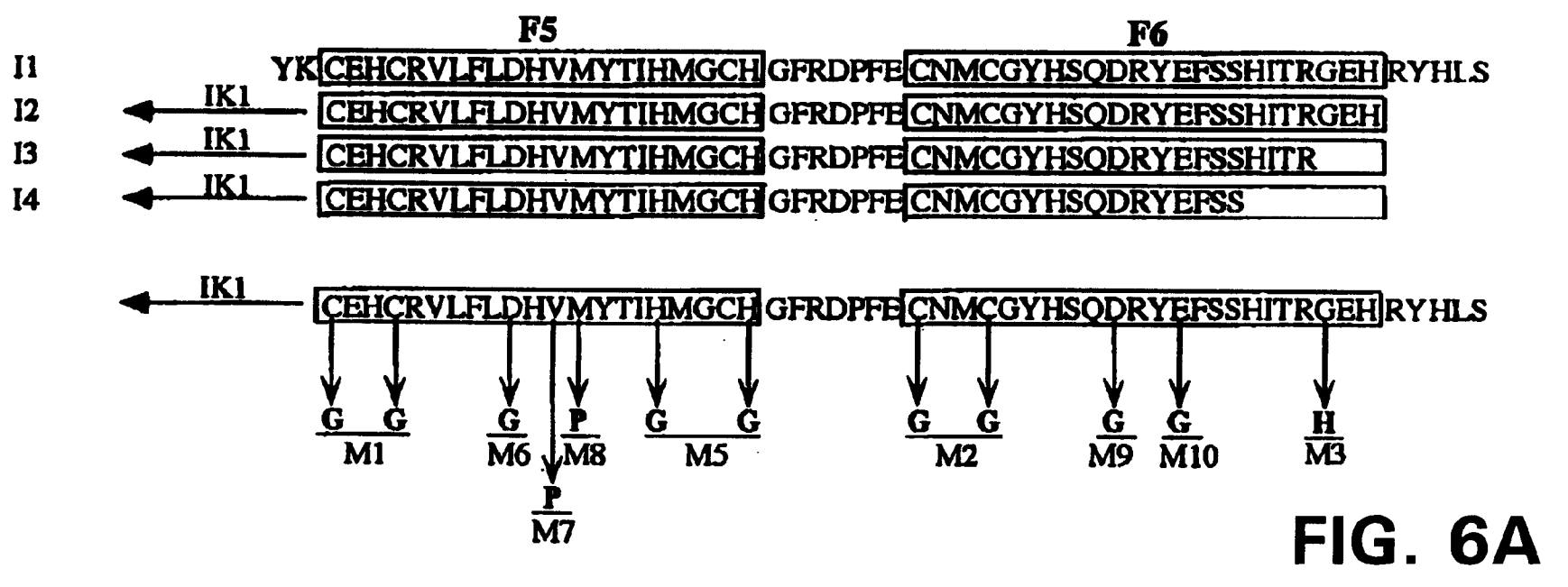
Figure 6B:
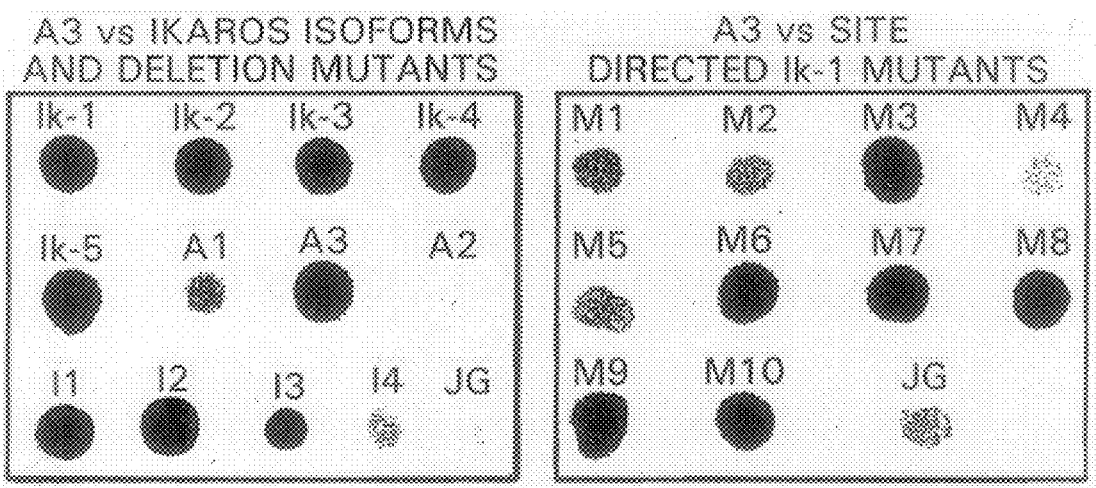

Protein-protein interactions between Ikaros isoforms were investigated in the yeast two hybrid system. Strong interactions were obtained with the most C-terminal 150 amino acids of exon −7 (FIG. 5A and FIG. 6B). 5' and 3' deletional analysis of this region defined the 58 most C-terminal amino acids as the interaction domain (FIG. 6A). This domain contained two Kruppel like zinc finger motifs (F5 and F6) present in all of the Ikaros isoforms. Substituting cysteine or histidine with glycine residues in F5 or F6 abrogated Ikaros protein-protein interactions (FIG. 6A and 6B, M1, M5 and M2 respectively). Deletion past the second histidine in F6 reduced but did not abrogate these protein interactions (FIG. 6A and 6B). However, deletion past the first histidine of this finger motif abolished the interaction potential of this region (FIG. 6A and 6B).

To determine whether a Kruppel zinc finger structure was essential for the Ikaros protein-protein interactions, non conservative substitutions were introduced in amino acids that would participate in the α-helix of this finger motif (FIG. 6B, M6,M7, M8, M11 and M13). None of these non conservative ammoniated substitutions had an effect on Ikaros protein-protein interactions. Therefore, the cysteine and histidine residues in the 53 amino acids C-terminal interaction domain may participate in the formation of a novel zinc finger structure essential for the Ikaros protein-protein interactions. Alternatively, F5 and partly F6 may assume the β-sheet/α-helix secondary structure characteristic of a Kruppel type zinc finger. However, the α-helical region of this finger motif primarily involved in making DNA contacts may be dispensed without affecting its ability to participate in protein-protein interactions.

Figure 6C:
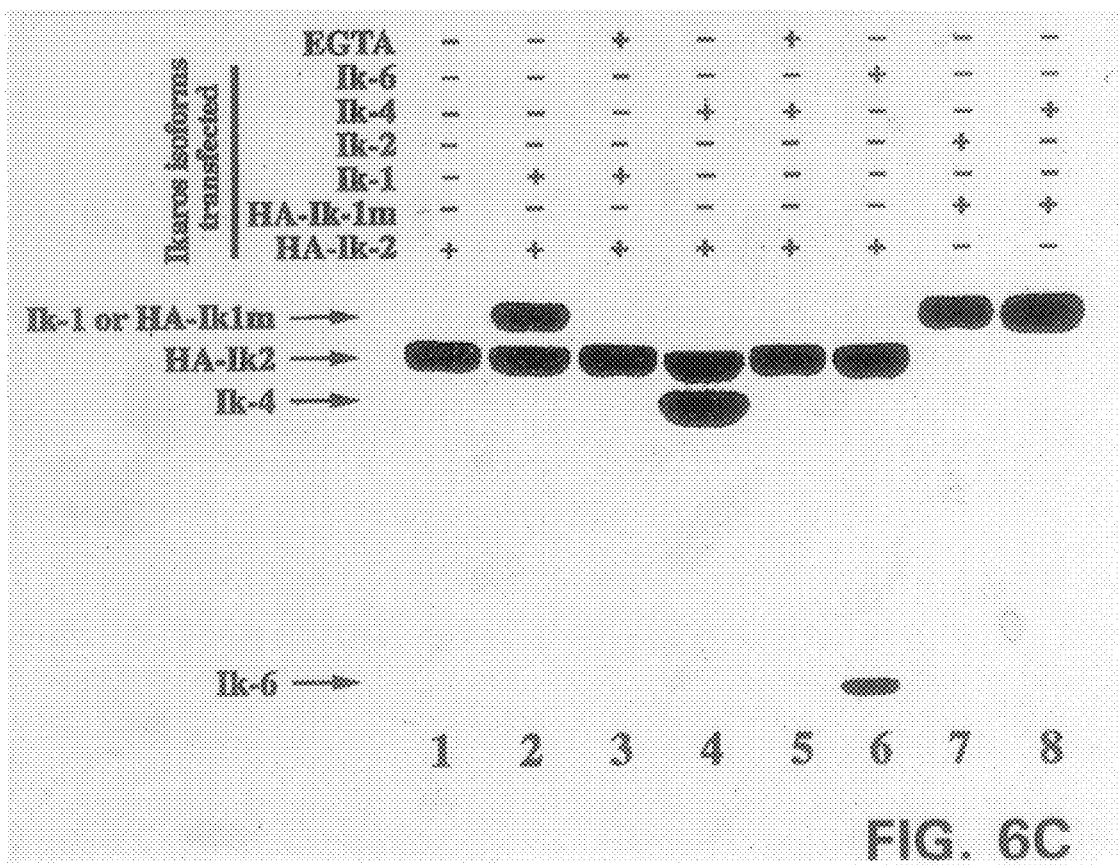

The ability of Ikaros isoforms to interact with each other was investigated in mammalian cells. The Ik-2 isoform tagged with the influenza epitope (HA) was co-transfected with other Ikaros isoforms (Ik-1, Ik-4, Ik-6, Ik-7) in the 293T epithelial cell line. The HA-Ik-2 isoform was immunoprecipitated from lysates of the transfected cells using a mouse anti-HA monoclonal antibody. The immunoprecipitates were analyzed by Western hybridization with Ikaros antibodies. Stoichiometric amounts of Ikaros isoforms (Ik-1. Ik4 and Ik-6) were coimmunoprecipitated with the HA-Ik-2 variant (FIG. 6C, lanes 2, 4 and 6). The seemingly lower amounts of Ik-6 immunoprecipitated were due to its short N-terminal region that contains fewer epitopes for the Ikaros polyclonal antibodies used in the assay (FIG. 6C, lane 6). Similar results to the HA-Ik-2 immunoprecipitations were also obtained with the HA-Ik-1 isoform. However, an HA-Ik-1 isoform with substitutions of glycine for cysteine residues in its two C-terminal zinc finger motifs was unable to interact and co-immunoprecipitate with the Ikaros isoforms (FIG. 6C, lanes 7 and 8).

Figure 6D:
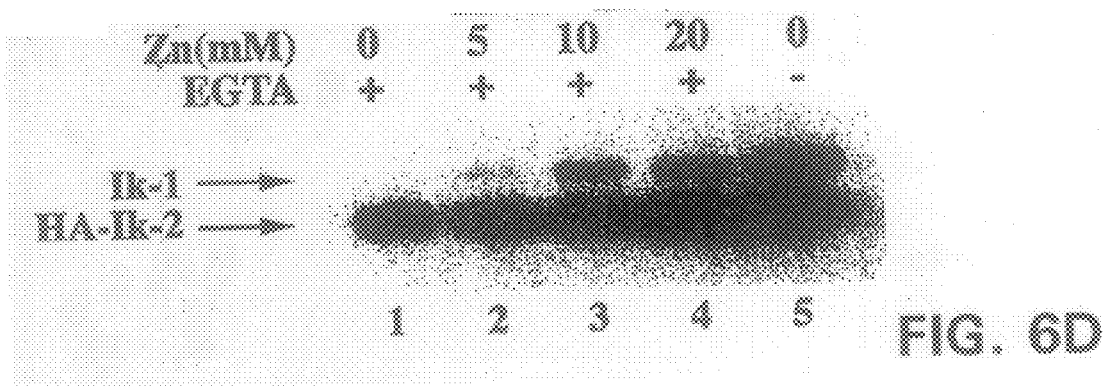
Figure 7A:
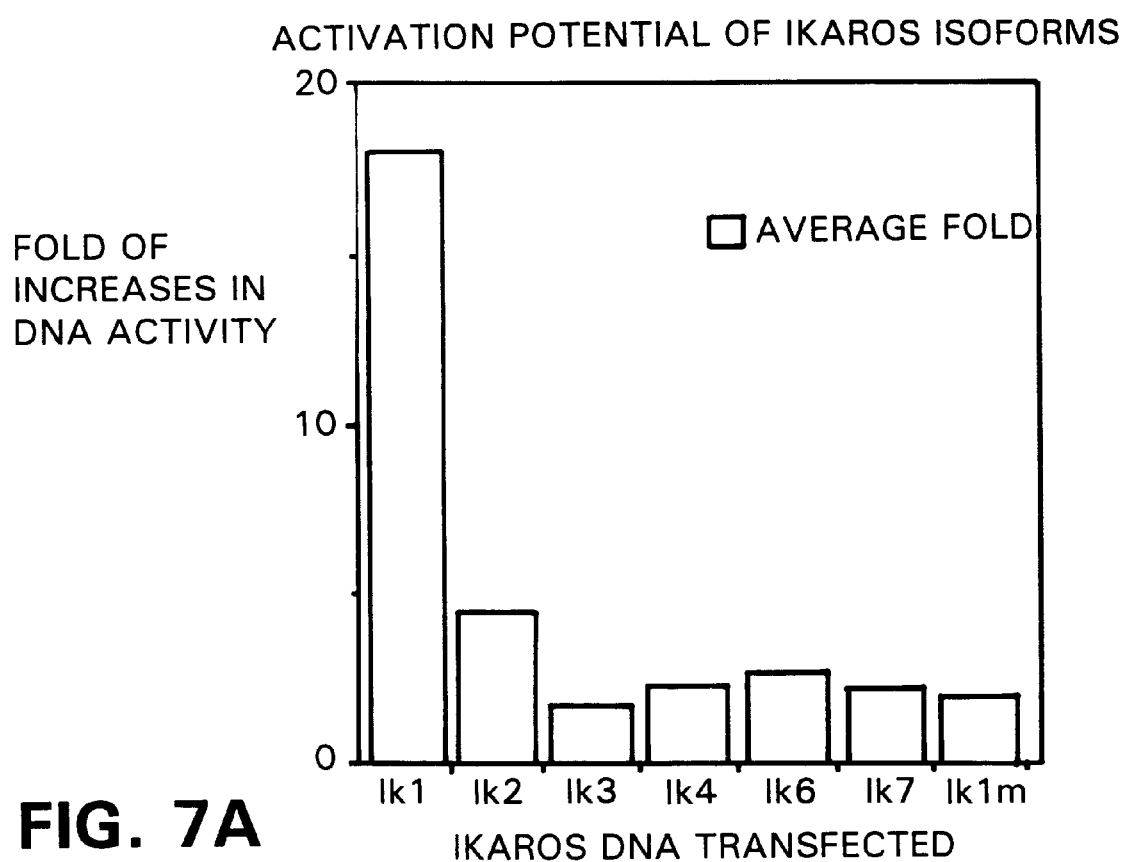
FIG. 7 is a graph depicting that protein-protein interactions between distinct Ikaros isoforms regulates their activity in transcription.
Figure 7B:
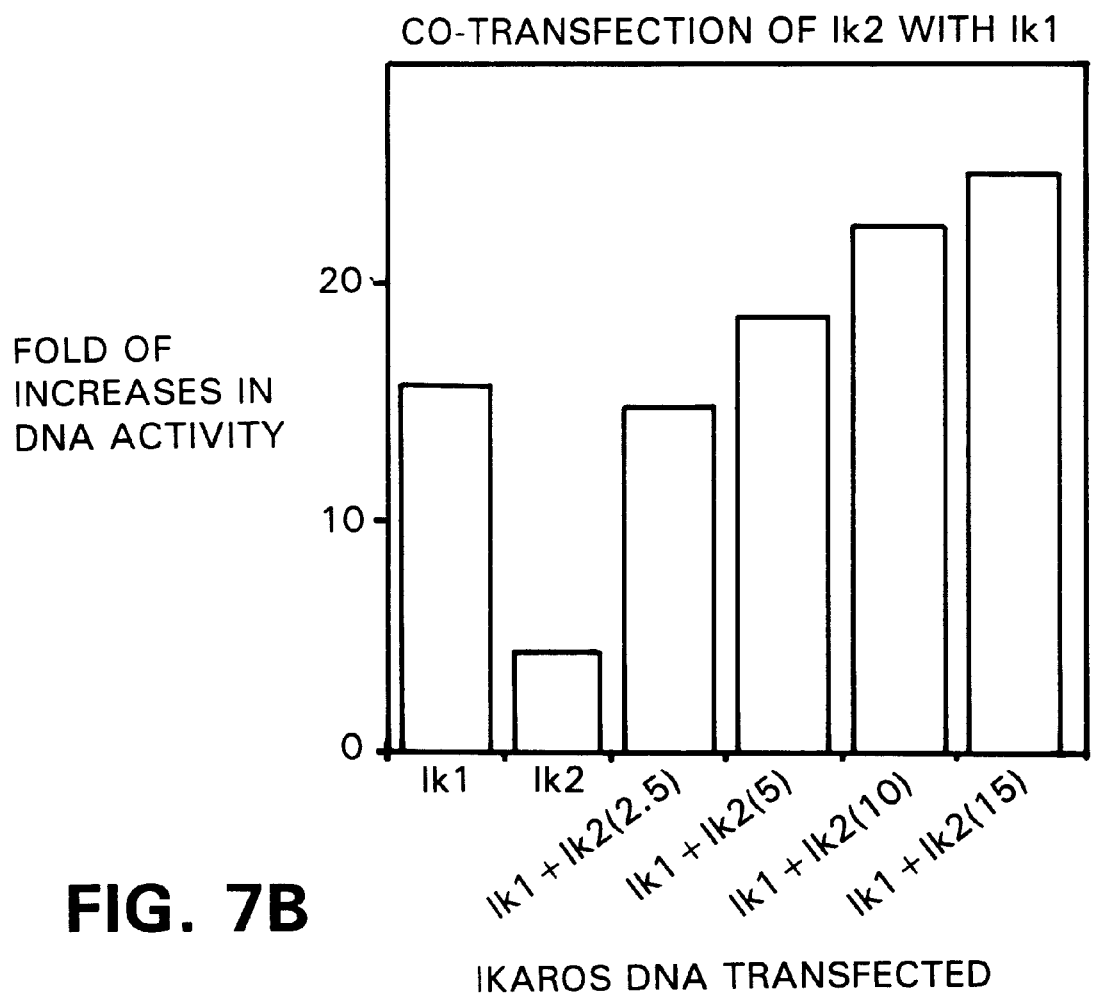
Figure 7C:
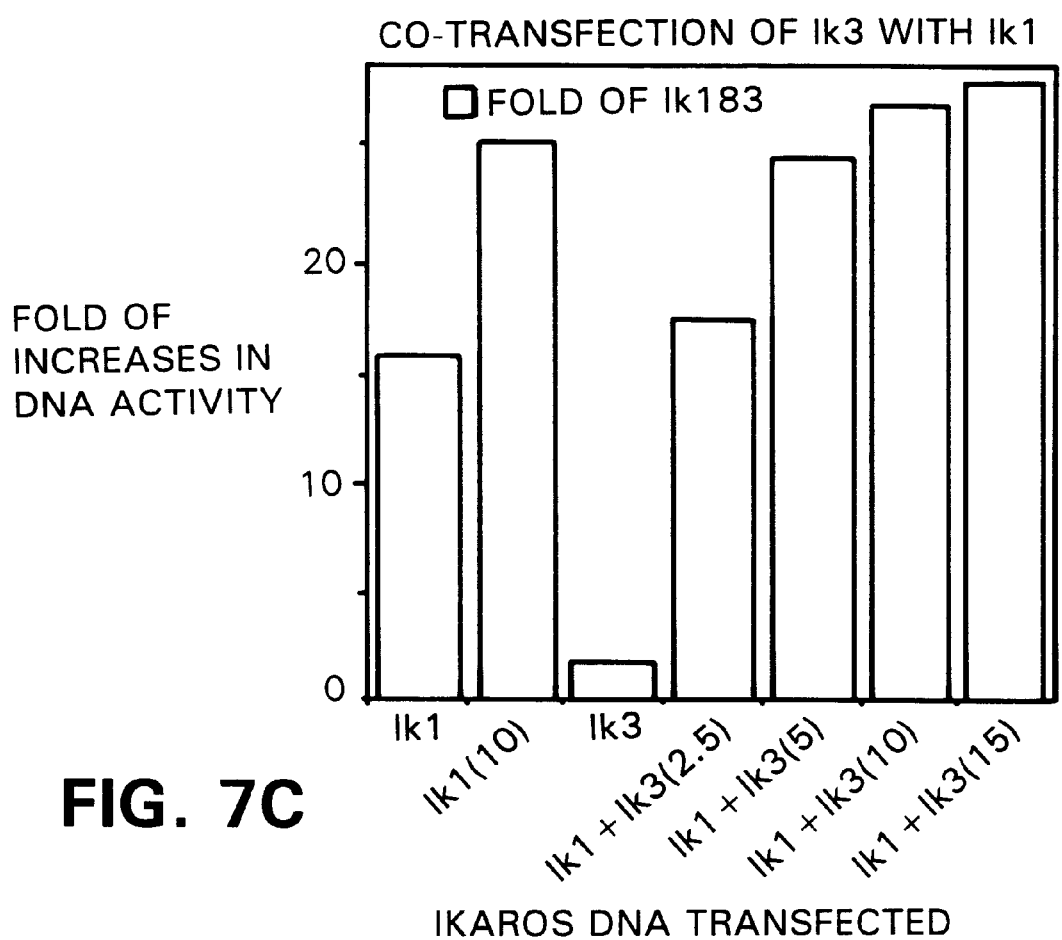
Figure 7D:
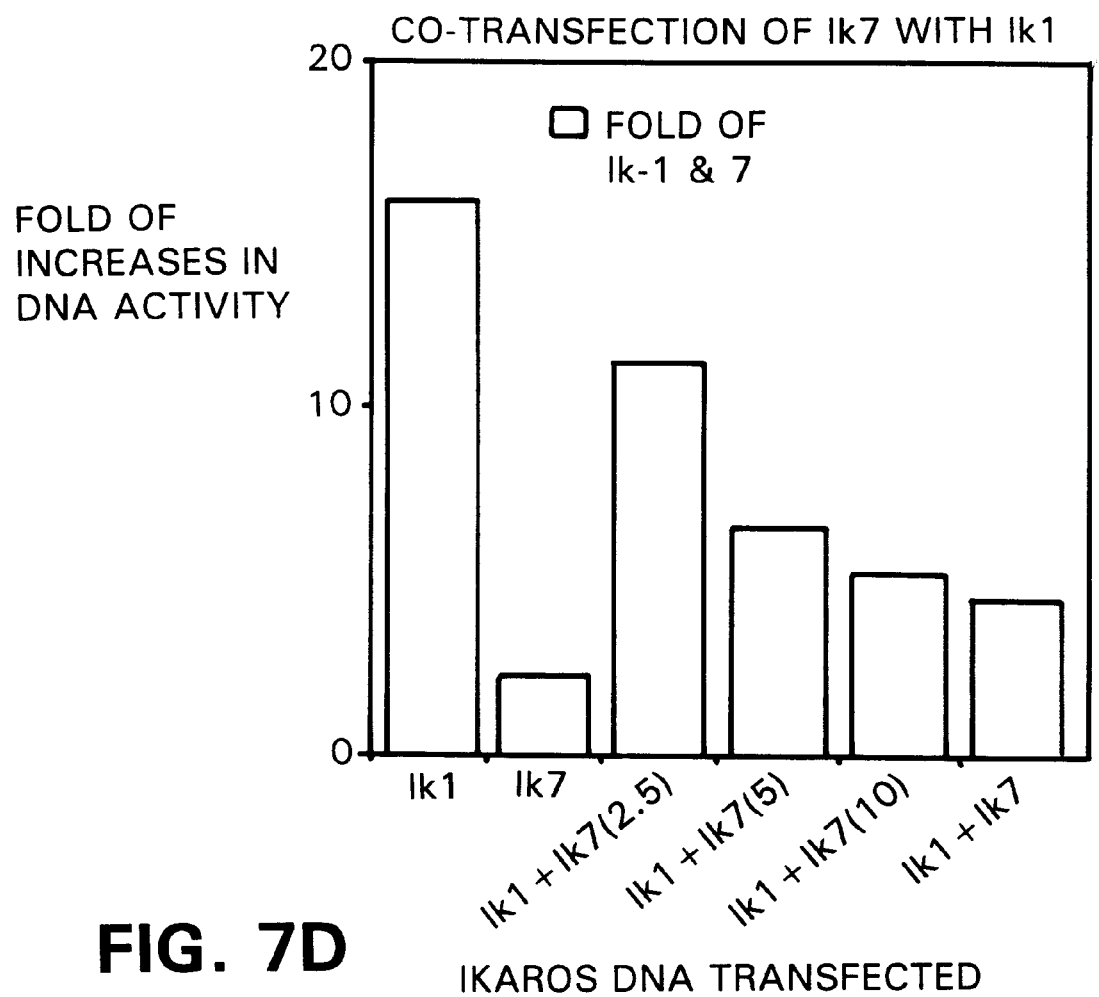
Figure 7E:
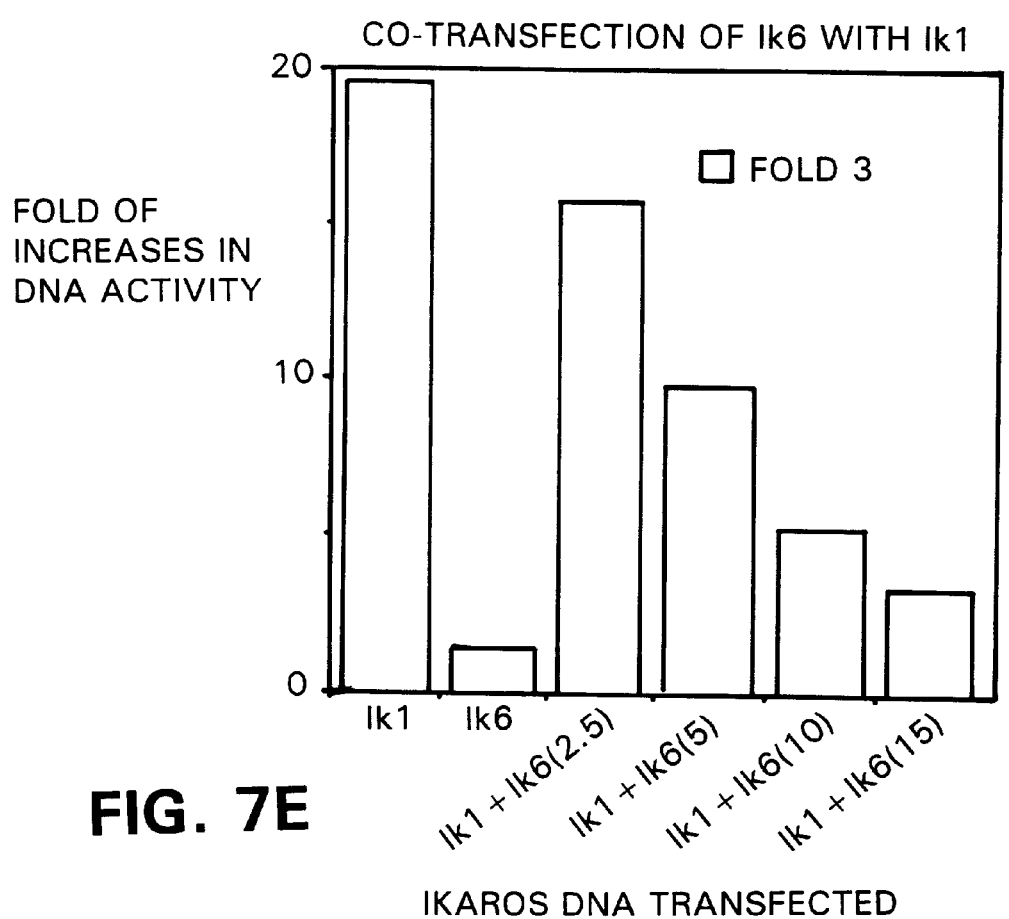
Figure 7F:
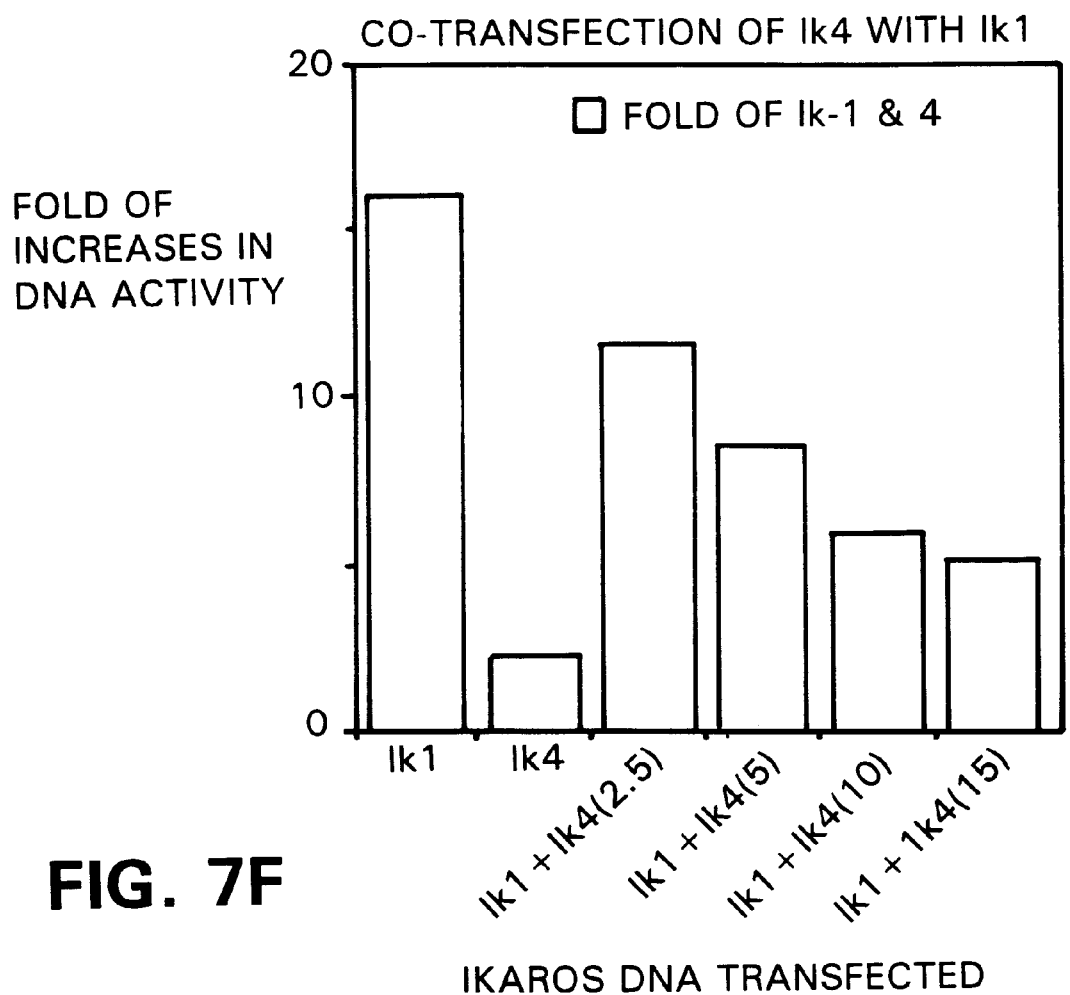

To determine whether zinc finger motifs were involved in Ikaros protein-protein interactions, the Zn chelating agent EGTA was added to the transfected cell lysates prior to immunoprecipitation. Addition of EGTA totally abrogated the interaction between Ikaros proteins (FIG. 6C, lanes 3 and 5). The ability of Ikaros proteins to interact was restored after adding increasing amounts of zinc ions to the EGTA treated lysates (FIG. 6D, lanes 3–5). These data together with mutational analysis of the Ikaros interaction domain in the yeast two hybrid system strongly support the involvement of a zinc finger interface in mediating stable Ikaros protein-protein interactions.

Cellular Localization

Distinct Ikaros isoforms display preferential localization to the nucleus or to the cytoplasm. In view of their stable interaction in the absence of DNA, it was examined whether the cytoplasmic forms of Ikaros could retain the nuclear forms outside the nucleus and therefore interfere with their function. The cytoplasmic isoforms Ik-6 or Ik-7 were co-transfected into NIH-3T3 cells together with the nuclear forms Ik-1 or interaction deficient isoform Ik-1m. Subcellular localization of these proteins was monitored with antibodies against Ikaros. Ik-6 and Ik-7 proteins were found in the cytoplasm in the absence of Ik-1 and Ik-1m. When Ik-1 was co-transfected, all Ikaros proteins were detected within the nucleus. However, when Ik-1m was co-transfected, Ik-6 and Ik-7 were still found in the cytoplasm while Ik-1m is in the nucleus. Similar results were also obtained for other cytoplasmic isoforms Ik-3 and Ik4. Therefore, nuclear and cytoplasmic Ikaros proteins form complexes through interaction and predominantly localize in the nucleus.

Protein-Protein Interactions and DNA Binding

Ikaros protein-protein interactions and their effect on DNA binding was investigated. Wild type and interaction deficient Ik-1 proteins (Ik-1 and Ik-1m) were used in a gel retardation assay against a single high affinity recognition sequence. Wild type Ik-1 bind DNA mostly as a dimer but lower amounts of monomeric and tetrameric complexes were also detected. In contrast to the wild type Ik-1, the interaction deficient Ik-1 mutant bound to DNA as a monomer. In addition, when equal amounts of the wild type and mutant Ik-1 were used in this assay, less amount of mutant proteins were found bound to DNA. Raising the Ikaros protein concentration increased the Ik-1 dimeric and the mutant Ik-1 monomeric protein-DNA complexes respectively. Formation of higher order protein-DNA complexes were not detected with the interaction deficient Ik-1 isoform.

Given that many physiological Ikaros binding sites (e.g., NFkb, EBF etc) are reiterated and that Ikaros proteins select with high frequency for dimeric recognition sequences, the affinity of Ik-1 for single versus double recognition sites was investigated. The same predominant dimeric and monomeric Ikaros protein-DNA complex were detected on both single and double recognition sequences with Ik-1 and mutant Ik-1 respectively. Steric hindrance mediated by the bound Ikaros proteins may prevent loading of a second protein complex on a proximal binding site.

Interaction between Ikaros isoforms with and without a DNA binding domain (Ik-1 and Ik-6) and its consequent effect on sequence specific binding were determined. The ability of Ik-1 to bind DNA was significantly reduced in the presence of the Ik-6 isoform. As described previously, homo-dimerization of an Ikaros isoform containing four N-terminal zinc fingers (Ik-1 with F1, F2, F3, F4) increased its affinity for sequence specific DNA binding, possibly by introducing two DNA binding domains in this protein complex. However, interaction between Ikaros isoforms with and without a DNA binding domain generates a protein complex with only one DNA binding module and a lower affinity for DNA.

Figure 3:
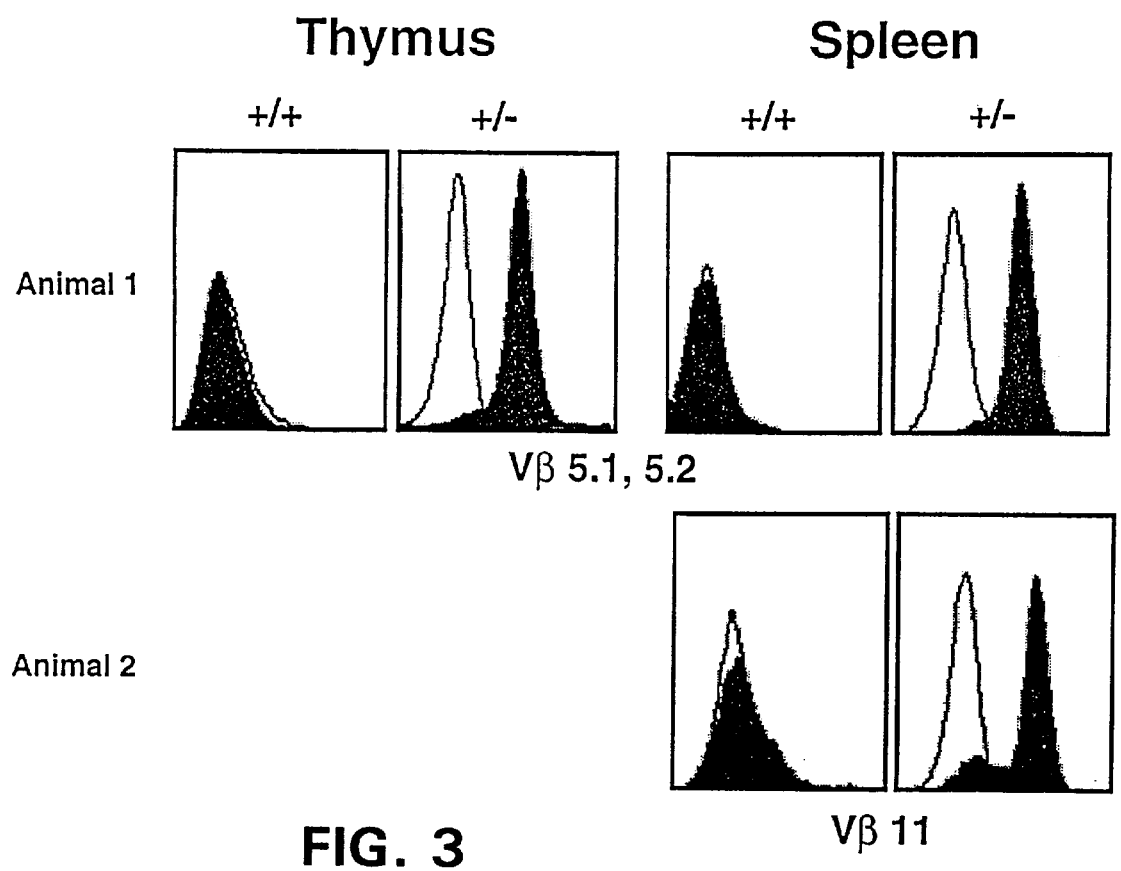
FIG. 3 is a graph depicting flow cytometric analysis of Vβ usage in the thymocyte and splenocyte populations of one Ikaros heterozygote (top panel) and the splenocyte population of a second (bottom panel). White histograms represent staining with isotype control antibodies.

Ikaros homo- and hetero-dimer formation and their transcriptional potential was determined. As previously shown, Ik-1 can function as a strong transcriptional activator when expressed ectopically in NIH-3T3 fibroblasts (FIG. 7, 20 fold stimulation). In contrast, the interaction deficient Ik-1 protein is a weak activator (FIG. 7, 2–3 fold stimulation). This significant difference in activity between the wild type and mutant Ik-1 may reflect differences in their DNA binding affinity. In addition, the presence of two activation domains in an Ik-1 homodimer may contribute to its higher transcriptional activity. Given that Ikaros isoforms can engage in both homo- and hetero-dimer formation, constant amounts of Ik-1 were co-transfected with increasing amounts of Ik-2, Ik-3, Ik4,Ik-5, Ik-6 or Ik-7. Effects observed past equal molar ratios continue to reflect Ikaros heterodimer formation. Co-expression of Ik-1 with Ik-4, Ik-6 or Ik-7 strongly interfered with the ability of the former isoform to activate transcription (FIG. 7). Formation of Ik-1 heterodimers (Ik-1/Ik-6, Ik-1/Ik-7 and Ik-1/Ik-4) with reduced DNA binding affinities may account for their weaker activation properties relative to Ik-1 homodimer (FIG. 7). However, these Ik-1 heterodimers were transcriptionally more active relative to the Ik-1 monomer (Ik-1m), probably due to the presence of a second activation domain in this protein complex. No negative effect on the activation potential of Ik-1 was detected with increasing amounts of the weaker activator Ik-2. The higher levels of reporter gene expression detected in Ik-2 excess may reflect the combined activity of Ik-1/Ik-2 hetero and Ik-2 homodimers both of which localize into the nucleus (FIG. 7). Since Ik-3 homodimers cannot enter the nucleus, the effects detected in Ik-3 excess are expected to be due to Ik-1/Ik-3 heterodimers. Ik-1/Ik-3 heterodimers were transcriptionally as active as Ik-1 homodimers (FIG. 7).

Figure 8A:
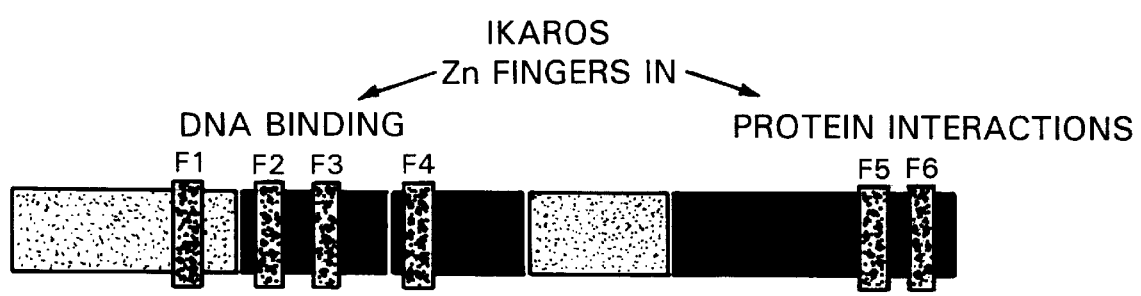
FIG. 8 is a schematic model of how formation of homo/heterodimeric complexes between distinct Ikaros isoforms can control proliferation versus differentiation a homolymphopoietic system.
Figure 8B:
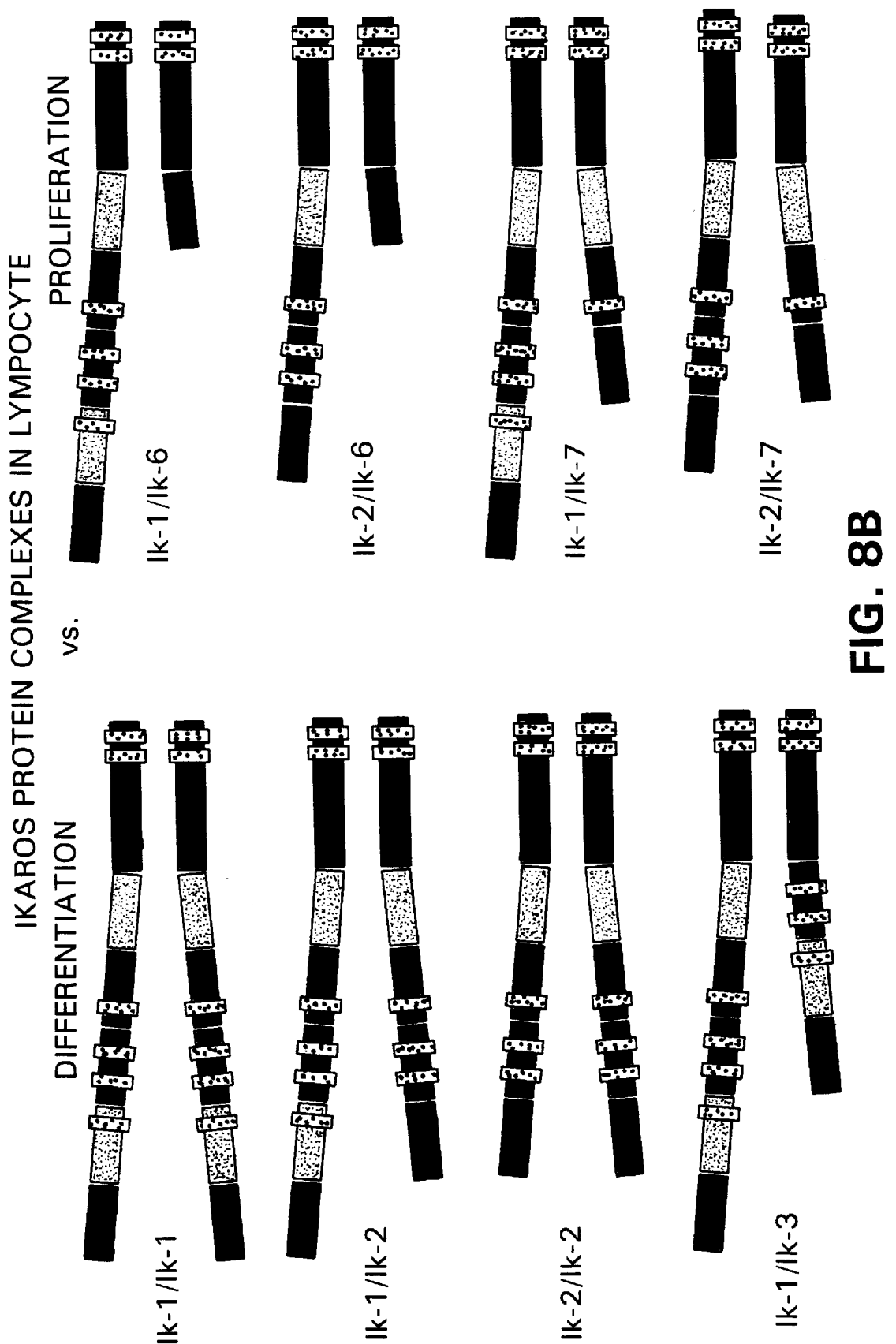

Protein-protein interactions between Ikaros isoforms with distinct DNA binding domains (i.e. Ik-1, Ik-2 and Ik-3) increase their affinity for DNA but may also expand the range of regulatory elements controlled by these factors. In addition, such interactions (e.g., Ik-1/Ik-3) can dictate the nuclear localization and transcriptional potential of the resulting heterodimer. However, the activity of these transcriptionally competent Ikaros isoforms is negatively regulated by distinct members of the same family which lack an intact DNA binding domain (e.g., Ik-4, Ik-5, Ik-6, Ik-7). Heterodimers formed between these functionally distinct Ikaros isoforms have a low affinity for DNA and a reduced activation potential. Deregulated expression of the autoregulatory Ikaros isoforms in lymphocytes can lead to an aberrant lymphocyte proliferation and a rapid transformation (FIG. 8). Such effects are readily manifested in lymphocytes bearing one Ikaros wild type and one mutant alleles which exclusively generate these isoforms. The same effect is observed when these negative regulating Ikaros isoforms are over expressed in the lymphoid lineage of transgenic mice.

Thus, the Ikaros gene generates, by means of alternate splicing, the tumor suppressor forms Ik-1, Ik-2 and Ik-3 which promote lymphocyte differentiation and prevent proliferation. It also generates the negative regulating proteins Ik-4, Ik-5, Ik-6, Ik-7, that support lymphocyte proliferation and transformation by interfering with the function of the former isoforms. While deregulated expression of these dominant negative Ikaros isoforms, produced at low frequency by the intact gene, leads to aberrant and malignant lymphoproliferation, their regulated expression during lymphocyte development may control proliferation and differentiation of early hemopoietic and lymphoid progenitors. For example, the Ik-4 isoform expressed at relatively high levels only in the E14 fetal thymus may be required for the proliferative expansion of early lymphoid progenitors. Further studies on the expression of Ikaros isoforms in purified populations of hemolymphoid progenitors as well as on potential genetic targets in these cells may begin to unravel the complex molecular process that regulates development and homeostasis in the hemolymphopoietic system.

Ikaros Null Mutation

To investigate the role of Ikaros protein interactions in the development of the hemolymphoid system, a different deletion at the C-terminus of the Ikaros gene was targeted. This deletion removes the last translated exon that includes domains involved in activation, dimerization and other protein interactions. The functionally null proteins made by the mutant locus are unstable and not detected at the cellular level. Both fetally derived B-1a and adult derived conventional B cells are absent from Ikaros C-terminal mutant (C−/−) mice. However, fetal and adult derived T cell lineages are differentially affected. Throughout gestation and for the first days after birth, the thymus is devoid of thymocytes and any of their identifiable precursors. Definitive thymocytes are detected in the postnatal thymus between days 3 and 5 after birth. These thymocytes expand to reach nearly normal numbers in the adult. T cell progenitors in the Ikaros C−/− neonatal thymus differentiate predominantly into conventional $\alpha\beta$ T cells and give rise to severely reduced numbers of adult derived $_\gamma\delta$ T cells. Consistent with the absence of fetal thymocyte development, no dendritic epidermal $V_\gamma 3$ T cells can be detected in the Ikaros C−/− mice. NK cells are also absent from these mice. Numbers of intestinal intraepithelial $_\gamma\delta$ T cells and of thymic dendritic antigen presenting cells (APCs) are severely reduced. Furthermore, differentiation along the $\alpha\beta$ T lineage is not normal. Thymic T cell profiles are skewed towards $CD4^+8^-$ cells and cells in transition to this phenotype. Thymocytes display augmented T cell receptor (TCR) mediated proliferative responses and a few weeks after their appearance oligoclonal expansions are detected. In aging homozygotes, monoclonal populations take over the thymus and are exported to the periphery. In spite of the consistent defects in the B and T lymphoid compartments manifested in Ikaros C−/− mice, normal to increased numbers of erythroid and myeloid cells are detected in the bone marrow and in the spleen. The phenotype of this Ikaros null mutation establishes the role of the Ikaros gene family in the lymphoid differentiation of fetal and postnatal HSCs.

Figure 9:
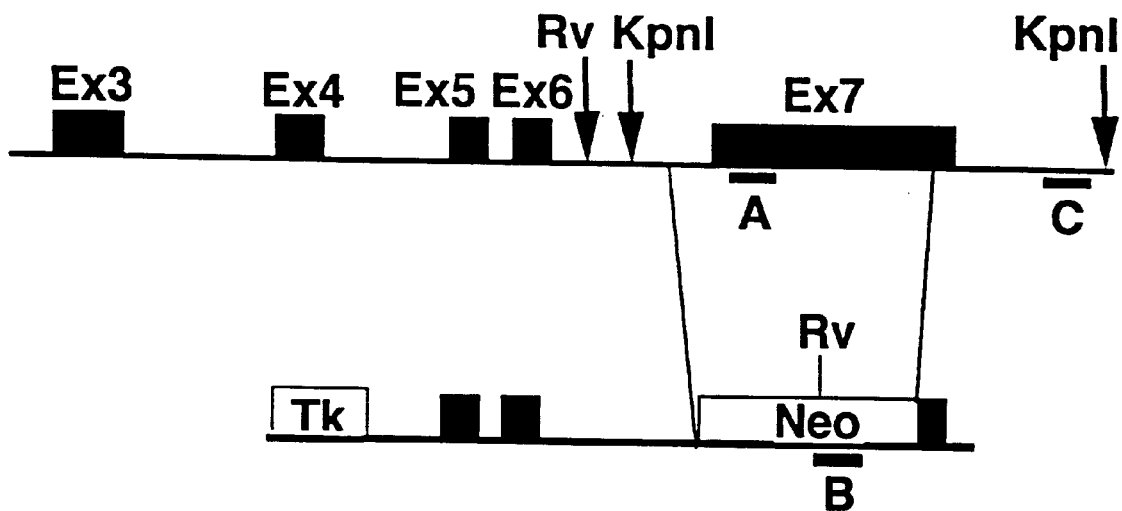
FIG. 9 is a schematic diagram depicting functional inactivation of the Ikaros gene by targeting its last translated exon. Recombination strategy for targeting a deletion of a 1.35 kB genomic fragment encompassing the 5' coding region of exon 7.

Deletion of the Last Translated Exon of the Ikaros Gene Leads to its Functional Inactivation To avoid the dominant negative effects of the Ikaros proteins generated by the N-terminal DNA binding domain deletion, a vector was designed to replace a 1.35 kB genomic fragment which contains the major part of the coding region of exon 7 including its 5' splice donor site with the neomycin resistance expression cassette by homologous recombination (FIG. 9). This deletion disables utilization of exon 7 from the Ikaros transcript. Exon 7 encodes the C-terminal zinc finger dimerization domain required for interactions among Ikaros proteins and between Ikaros and Aiolos proteins. The deleted domain also contains a bipartite activation domain essential for the ability of the Ikaros proteins to activate transcription. In vitro and in vivo studies with mutant Ikaros proteins in which the dimerization domain has been disrupted or which lack the last translated exon have shown that they are transcriptionally inactive and do not display dominant negative effects on transcription.

The targeting vector was homologously recombined in the mouse germ line at an 1:8 frequency. Two independent embryonic stem cell lines with legitimate homologous recombination events were used to generate mice with germ line transmission for the C-terminal deletion. Homozygous C-terminal mutant mice were born with the expected Mendelian frequency and were indistinguishable from their wild type littermates. They live up to four months and males can breed. Their longevity is in contrast to the Ikaros DNA binding deletion mutants most of which die during the first three weeks after birth (Georgopoulos et al. (1994) Cell 79, 143–156).

Northern hybridization of RNA prepared from Ikaros C−/− thymocytes using an N-terminal Ikaros cDNA probe revealed decreased levels of a short 700 to 900 bp message that lacks both the coding and long untranslated region of exon 7. Immunohistochemical analysis of Ikaros C−/− thymocytes using antibodies raised to the N-terminal domain of the Ikaros proteins failed to reveal the characteristic punctate nuclear Ikaros staining or any staining above background. Nevertheless, Ikaros C−/− thymocytes stained readily with an antibody to the Ikaros homologue Aiolos. A mutant Ikaros protein was detected in western blots of C−/− thymocytes lysates but at 100 fold lower concentrations than the wild type Ikaros proteins present in wild type thymocyte lysates.

The experiments described above were performed essentially as follows. The recombination vector described in FIG. 9 was constructed with Ikaros genomic fragments and neomycin and thymidine kinase expression cassettes and was targeted into J1 embryonic stem cells as previously described (Georgopoulos et al. (1994) Cell 79, 143–156; Li et al. (1992) Cell 69, 915–926). DNA was prepared, digested with Kpn I and EcoRV and analyzed by Southern blotting using a DNA probe from outside the homologous recombination area (probe A). Single integration events were scored using a probe derived from the neomycin gene (probe B). Two distinct ES cell lines heterozygous for this mutation were used in separate blastocyst injections to rule out phenotypes that result from cell line mutations. To explore potential phenotype variability on distinct genetic backgrounds the mutant ES cells were injected in blastocysts from C57BL/6 and Balb/c mice. The genotype of F1–F3 mice was determined by Southern and by PCR analysis of tail DNA using either probe A or appropriate primers designed from the neomycin (Neo1) and the Ikaros gene (Int-7F and Ex7R).

Int-7F: GGG CCT TTG GGG ACA TCG AAG GTC (SEQ ID NO:9)

Ex7R: CAT AGG GCA TGT CTG ACA GGC ACT TGT (SEQ ID NO: 10)

Neo1: CCA GCC TCT GAG CCC AGA AAG CGA (SEQ ID NO: 11)

Expression of Ikaros and Aiolos proteins in wild type and mutant thymocytes was performed as previously described (Sun et al., 1996, EMBO J.). N-terminal Ikaros and Aiolos antibodies were used at 1:300 dilution. Stained cells were visualized with a Leica confocal epifluorescence microscope with a 100× objective lenses.

Tissues harvested from euthanized wild type and Ikaros C−/− mice were fixed in 4% buffered formalin for 1–2 days. They were then processed and embedded in paraffin. Sections were cut at 5 micron thickness, mounted and stained with hematoxylin and eosin. Light microscopy was performed at 2–40×magnification on an Olympus BMax-50 microscope.

Ikaros C−/− mice were analyzed in parallel with age matched wild type siblings. At least 20 groups of animals were studied on each mixed background (SV129×C57BL/6 and on SV129×Balb/c). Single cell suspensions of thymus, spleen or bone marrow cells were prepared and analyzed for their lymphoid, myeloid and erythroid populations on a FACScan as previously described (Georgopoulos et al. (1994) Cell 79, 143–156; Winandy et al. Cell 83, 289-99, 1995). Monoclonal antibodies conjugated with phycoerythrin, fluorescein or cychrome were used in two or three color cytofluorometric analyses.

Both Fetal and Adult Derived B Cells are Absent in Ikaros C−/− Mice

Figure 10A:
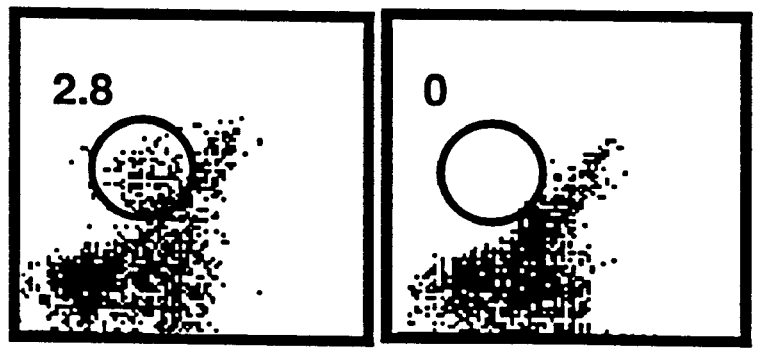
FIGS. 10A–D is a cytofluorometric analysis. Both fetal and adult B cell development are blocked in Ikaros C −/− mice. Cells obtained from the E-16 fetal liver (A); and peritoneum (B), bone marrow (C) and spleen (D) of four week old Ikaros C−/− mice and wild type litter mates were analyzed with the following combinations of mAbs: (A) anti-CD45R$^{PE}$/anti-CD43,$^{FITC}$ (B) anti-CD5$^{PE}$/anti-CD45R,$^{FITC}$ (C) anti-CD45R$^{PE}$/anti-CD43,$^{FITC}$ (D) anti-CD45R$^{PE}$/anti-IgM.$^{FITC}$ Positively stained populations are boxed and percentages shown. Fetal liver pre-B cell precursors (CD45R$^+$) and their progeny, peritoneal B-1a B cells (CD5$^+$/CD45R$^+$), were absent in Ikaros C−/− mice. Bone marrow pro-B cells and splenic B cells were also missing from all C−/− mice tested.
Figure 10B:
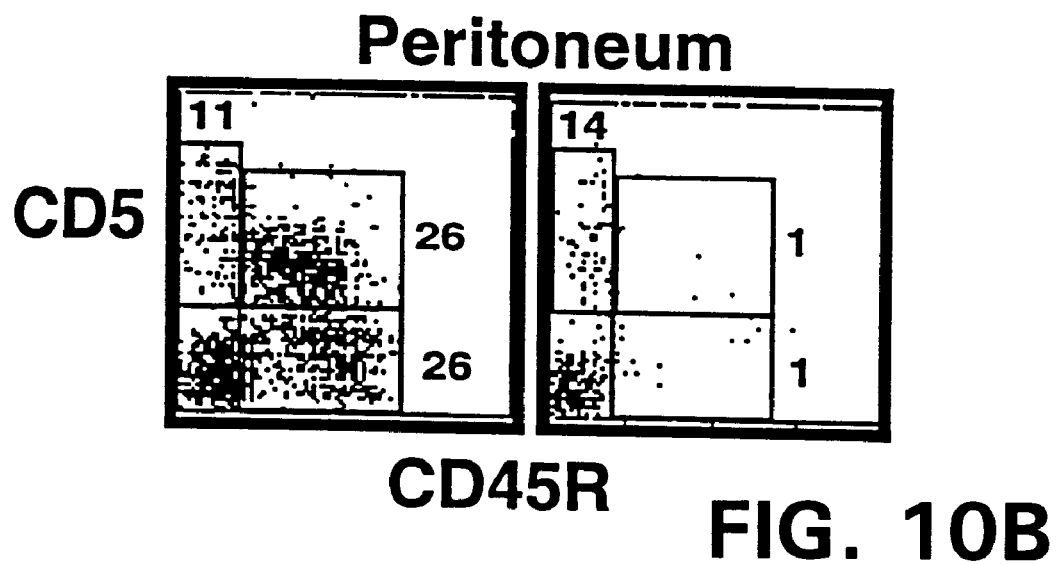
Figure 10C:
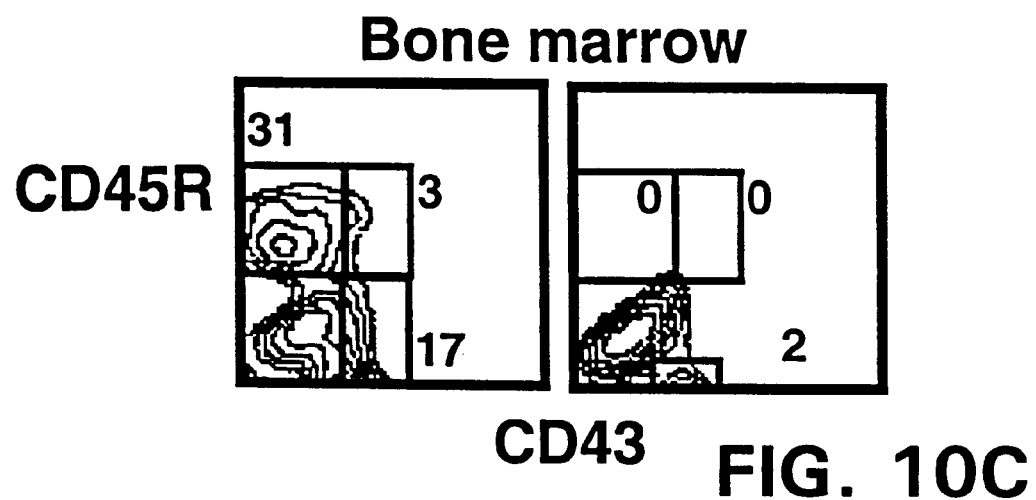
Figure 10D:
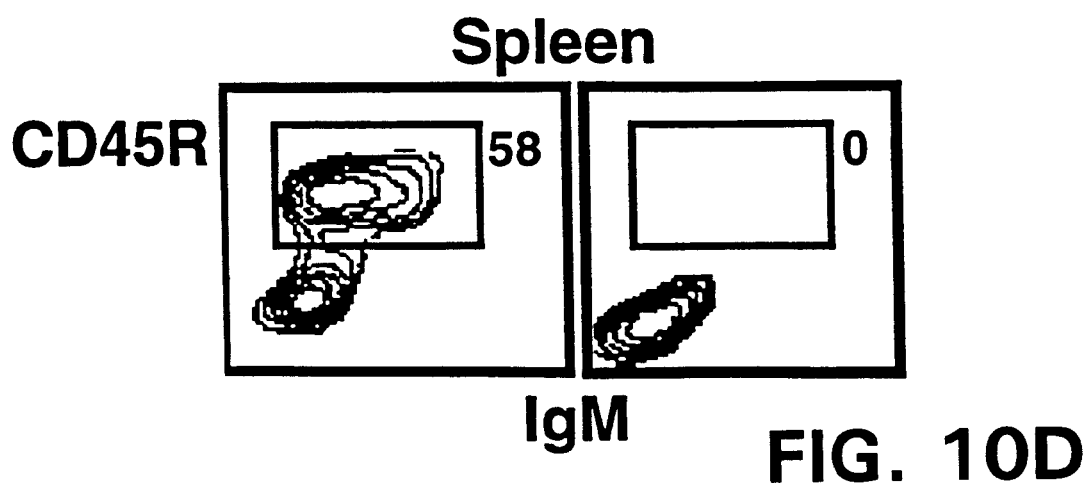

B cells and their precursors were absent during both the fetal and postnatal stages of development in Ikaros C−/− mice. Fetal liver B cell precursors (CD45R$^+$) were absent (FIG. 10A). These cells normally give rise to B1-a B cells (Hardy et al. (1994) Immunological Reviews 137, 92-118; Hardy et al. (1991) J. Exp. Med. 173, 1213–1225; Kantor, et al. (1992) Ann N Y Acad Sci 651, 168-9). Consistently, B1-a B cells (CD5$^+$/CD45R$^+$) were not detected in the peritoneum of adult homozygotes (FIG. 10B). Pro-B cells (CD45R$^+$/CD43$^+$) and pre-B cells (CD45R$^+$) were absent from the bone marrow and mature B cells (CD45R$^+$/IgM$^+$) were absent from the spleens of adult Ikaros C−/− mice (FIG. 10B–10D) (Hardy et al. (1991) J. Exp. Med. 173, 1213–1225; Li et al. J. Exp. Med. 178, 951–960, 1993).

Fetal but not Postnatal Waves of Thymocyte Differentiation are Impaired in Ikaros C−/− Mice Fetal but not postnatal waves of thymocyte differentiation are absent in Ikaros C−/− mice. The structure of wild type and Ikaros C−/− thymuses is revealed by hematohylin and eosin staining at 2–4×magnification. Thymocyte precursors are detected in the wild type but not in the mutant thymus at E-16. A difference in size between the two thymuses is already apparent at this early stage of thymocyte development. The thymus in Ikaros C−/− mice was devoid of identifiable lymphoid precursors throughout fetal life and for the first few days after birth. No cortical or medullary structures were discernible in the thymus of newborn homozygous mutants. In all respects, the newborn Ikaros C−/− thymus was very similar in appearance to the day 13–14 fetal organ at the beginning of its development as a thymopoietic site. In sharp contrast, the thymus in wild type newborns had formed elaborate cortical and medullary structures which are indicative of an actively differentiating thymocyte compartment.

Between three to six days after birth, thymocytes were detected in the Ikaros C−/− thymus but at 100–300 fold lower numbers than in the age matched wild type organs (0.2–1×10$^6$ vs 0.5–1×10$^8$). The thymus in Ikaros C−/− mice began to develop cortical and medullary structures within a week after birth. A dramatic increase in the number of Ikaros C−/− thymocytes was detected between the second and sixth weeks post partum. The number of thymocytes ranged from normal to 2–5 fold lower than wild type in the 4–6 weeks old homozygotes.

Figure 11A:
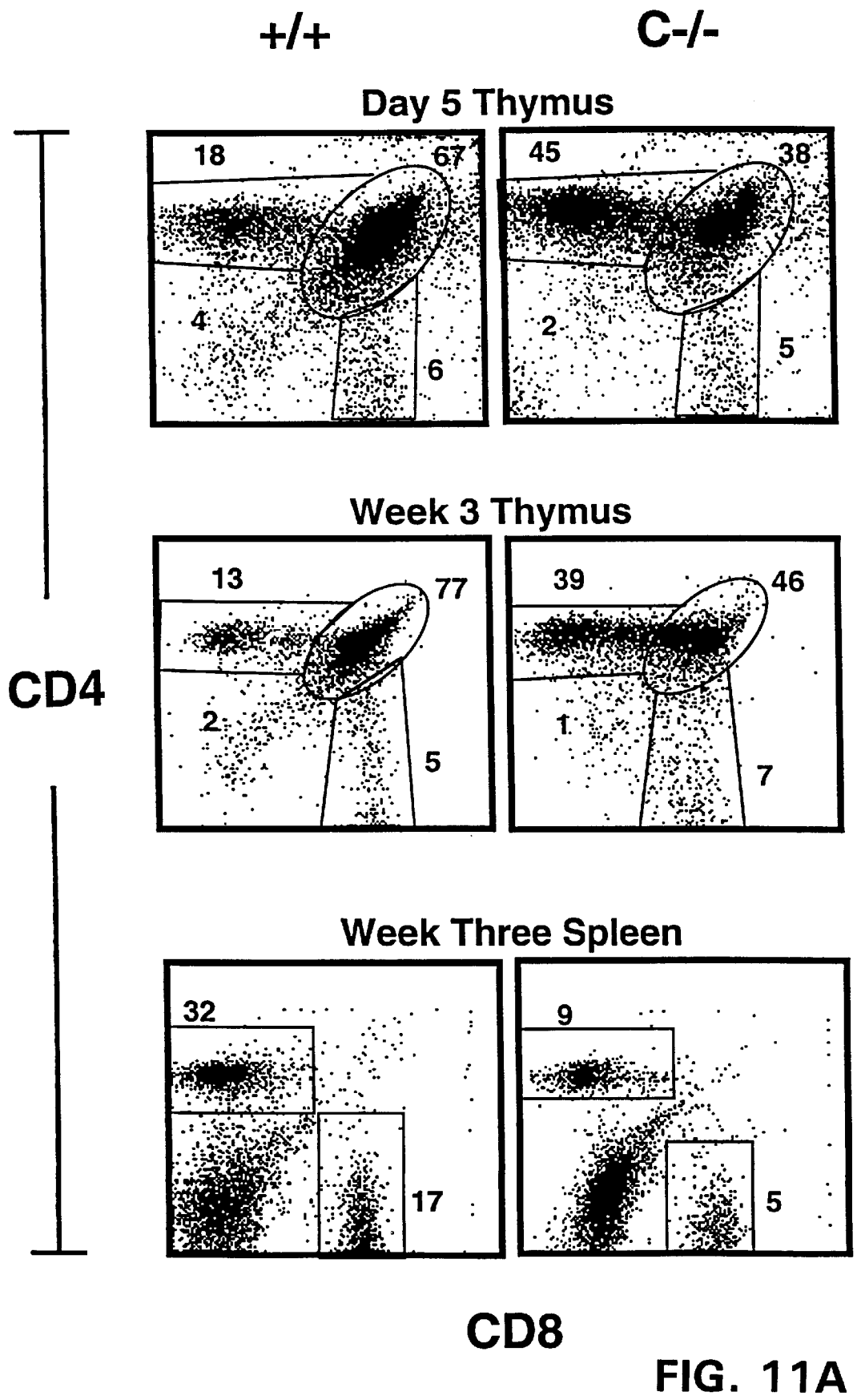
FIGS. 11A & B.

In spite of their increase in numbers, Ikaros C−/− thymocytes do not follow a normal differentiation pathway. A larger proportion of CD4$^+$8$^-$ single positive cells was present in the Ikaros C−/− thymus than in the wild type (FIG. 11A). CD4 single positive T cells accounted for up to 50% of the thymic population in these young animals which had 50–100 fold fewer total thymocytes than their wild type siblings (FIG. 11A). This increase in the CD4$^+$8$^-$/TCR$^+$ population was detected from the early points of thymocyte development to the adult and was accompanied by a concomitant decrease in the proportion of double positive thymocytes (FIG. 11A). The proportion of CD8 single positive cells was similar to that found in wild type (FIG. 11A).

C57BL/6 background, the absolute number of splenic T cells remained significantly reduced compared to wild type. The ratio of splenic CD4 to CD8 T cells varied from being similar to wild type to being increased by 2–3 fold (FIG. 11A).

The ability of Ikaros C−/− and wild type thymocytes and splenic T cells to proliferate when stimulated through their TCR was compared next. Ikaros C−/− thymocytes proliferated more than wild type thymocytes upon stimulation of their TCR complex (Table 2). Both CD4$^+$ and CD8$^+$ Ikaros C−/− thymocytes displayed a high degree of proliferation.

TABLE 2

| Population | Phenotyp | Cells per Well(× 10$^5$) | $^3$Thymidine Incorporation (SD)$^a$ | |
|---|---|---|---|---|
| | | | +/+ | −/− |
| Thymocytes | Whole$^b$ | 1.25 | 9,044 (446) | 73,736 (2,766) |
| | | 0.63 | 4,299 (179) | 34,743 (1,713) |
| | | 0.3 | 360 (670) | 10,474 (2684) |
| | CD4$^+$8$^-$ | 1.25 | 10,665 (13,481) | 127,470 (25,404) |
| | | 0.63 | 8635 (4833) | 65,617 (6,139) |
| | | 0.3 | 9461 (5541) | 28,872 (7,105) |
| | CD4$^-$8$^+$ | 1.25 | 36,760 (1148) | 175,189 (26,250) |
| Spleen Cells | Whole$^d$ | 2.5 | 51,561 (5,480) | 52,874 (5,863) |
| | | 1.25 | 12,716 (822) | 18,011 (1,859) |
| | | 0.63 | 3,765 (579) | 8480 (555) |

$^a$Duplicate samples of thymocytes or spleen cells were stimulated with plate bound anti-TCR mAb (H57) and irradiated syngeneic APCs for 48 hours, pulsed for 4 hours with $^3$H Thymidine, harvested and counted. Background $^3$H Thymidine incorporation (cells identically cultured with plate bound hamster Ig and irradiated APCs) ranged from 100 to 775.
$^b$The +/+ thymus contained 8.8% and 3.5% CD4$^+$8$^-$ and CD4$^-$8$^+$ cells respectively; and the −/− thymus contained 31% and 3.4% CD4$^+$8$^-$ and CD4$^-$8$^+$ cells respectively.
$^c$CD4$^+$8$^-$ and CD4$^-$8$^+$ cells were separated to 95% purity by sorting on a Coulter Elite.
$^d$The +/+ and −/− spleens contained 22% and 10% T cells respectively. T cell populations analyzed were from three week old animals.

Figure 11B:
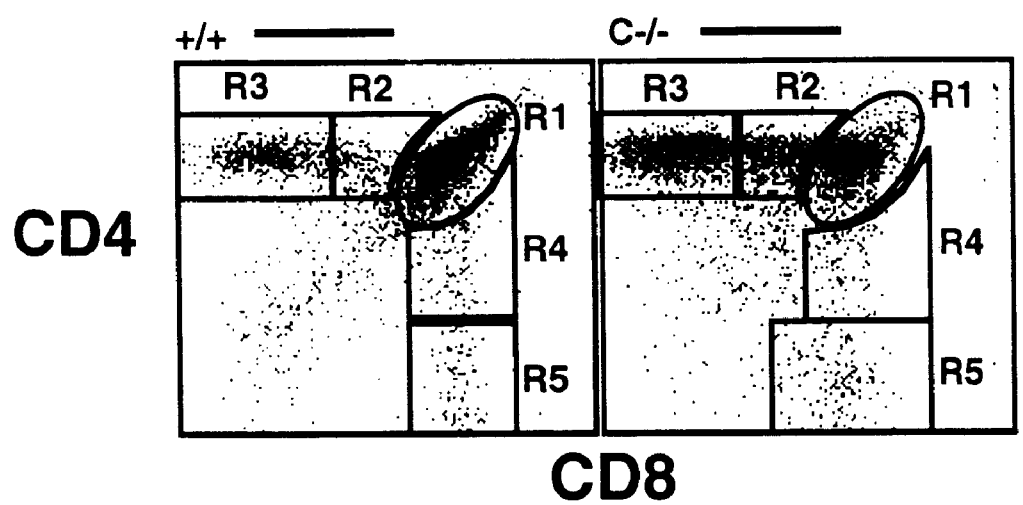
FIG. 11B is a cytofluorometric analysis depicting T cell development in the postnatal Ikaros C−/− thymus. CD4$^+$/CD8$^+$ (R1), CD4$^+$/CD8$^{int}$ (R2), CD4$^+$/CD8$^-$ (R3), CD4$^{int}$/CD8$^+$ (R4)and CD4−8$^+$ (R5) populations were analyzed for expression of the TCR complex and of the activation marker CD69. Levels of TCR expression were similar between wild type and Ikaros mutant mice. In contrast to the great majority of wild type presumptive transitional stage thymocytes (R2 and R4) which expressed CD69, the corresponding Ikaros C−/− thymocyte populations did not. A similar lack of CD69 expression was observed among the single positive CD4 mutant thymocytes (R3). In contrast the level of CD69 on CD8 single positive cells was similar to wild type (R5).
Figure 11C:
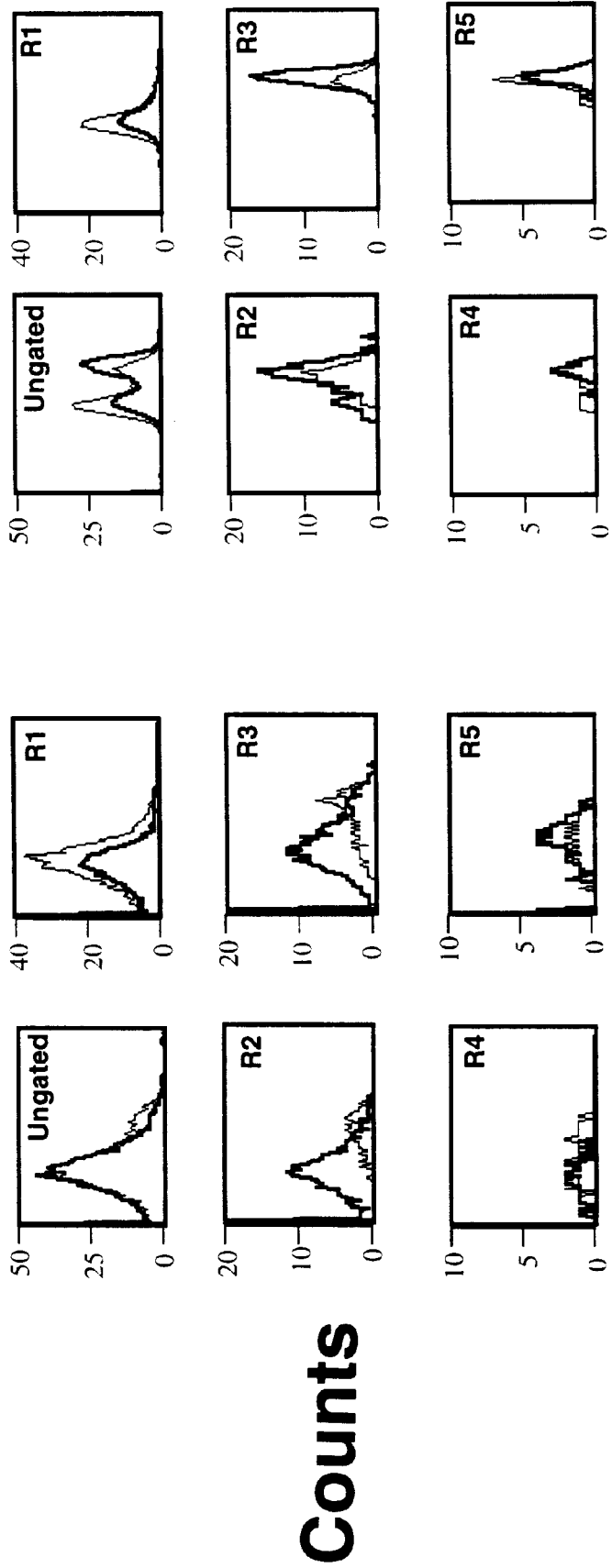

The increase in the CD4 population includes a combined expansion of both CD4 single positive and CD4$^+$/CD8$^{int-lo}$ intermediates (FIG. 11A). These CD4$^+$/CD8$^{int-lo}$ and CD4 single positive thymocytes expressed intermediate to high levels of TCR respectively suggesting that these cells follow the normal maturation pathway (FIG. 11B, TCR histograms). Ikaros C−/− thymocytes were also tested for expression of surface markers which become upregulated during positive selection (reviewed by von Boehmer et al., 1993). Expression of the CD69 antigen was tested in double positive, intermediates and single positive thymocytes. Positively selected thymocytes and activated peripheral T cells express the CD69 antigen transiently (Bendelac et al. (1992) J Exp Med 175, 731–742; Swat et al. Eur J Immunol 23, 739–746, 1993). In contrast to their wild type counterparts, the majority of CD4$^+$/CD8$^-$ and CD4$^+$/CD8$^{int}$ thymocytes in the Ikaros C−/− mice did not express the CD69 activation marker (FIG. 11B, CD69 histograms). CD8 thymocytes in these mutant mice expressed levels of the CD69 antigen similar to wild type CD8$^+$ thymocytes. Nevertheless, CD4$^+$8$^-$ thymocytes were capable of expressing CD69 after their in vitro stimulation through their TCR. These data suggest that Ikaros C−/− thymocyte precursors can transit to the CD4 single positive stage without receiving the appropriate positive selection signals. In the absence of a functional Ikaros gene the increased CD4 single positive thymocyte population may include inappropriately selected T cell clones.

The absolute number of T cells detected in the postnatal spleen of Ikaros C−/− mice was initially low but increased with age. In some cases, especially with animals of the Clonal Populations are Detected in the Early Ikaros C−/− Thymus and Predominate in the Adult Organ Given that Ikaros C−/− thymocytes hyperproliferated upon TCR stimulation, we tested for the presence of clonally expanded thymocyte populations in Ikaros C−/− thymuses. Dβ to Jβ segment rearrangments of the T cell receptor β chain gene were examined in wild type and mutant populations. Seven Dβ2-Jβ2 rearrangements and one band corresponding to the germnline configuration of the β chain gene were detected in the thymuses and spleens of wild type mice. These results are consistent with the normal polyclonal nature of thymocytes and mature T cells in these organs. In contrast, certain Dβ2-Jβ2 rearrangements showed an increase in intensity in Ikaros mutant thymuses as early as five days after birth, indicating expansion of certain thymocyte clones. A single Dβ2-Jβ2 rearrangement predominated in the thymuses of the majority of C−/− animals older than four weeks reflecting the presence of an expanding thymocyte clone. Aberrant clonal T cell populations were detected at later time points in the spleens of older mutants.

The stage in thymocyte development in which Ikaros C−/− thymocyte clones began to expand was investigated by staining thymocytes with antibodies to CD4, CD8 and a panel of Vβ specific monoclonal antibodies. Thymocyte clones with distinct TCR V$_β$ usage were seen in the majority of C−/− thymuses. Expanded populations of thymocytes expressing a given TCR V$_β$ were detected in both the double positive (CD4$^+$8$^+$) and single positive (CD4$^+$8$^-$ or CD4$^-$8$^+$)

windows indicating that their aberrant clonal expansion occurs as early as the immature double positive stage but these cells transit and further proliferate as single positive CD4+ and CD8+ thymocytes.

The experiments described above were performed essentially as follows. DNAs were prepared from thymocytes and splenocytes as previously described (Winandy et al. Cell 83, 289-99, 1995). Sequences of synthetic oligonucleotides (5' to 3') used as primers (Dβ2.1 and Jβ2.7) and as an internal probe (DβINT) for Southern analysis are as follows:

Dβ2.1: GTA GGC ACC TGT GGG GAA GAA ACT (SEQ ID NO: 12)

Jβ2.7: TGA GAG CTG TCT CCT ACT ATC GAT T (SEQ ID NO: 13)

DβINT: TAT TG GGG ACT GGG CG (SEQ ID NO: 14)

Selective Defects in $_\gamma\delta$ T Cells in Ikaros C−/− Mice

The number and distribution of $_\gamma\delta$ T cell subsets was of particular interest because of the lack of fetal thymocyte development in Ikaros C−/− mice. Dendritic epidermal T cells (DETC) expressing $_\gamma\delta$ TCR which were readily identified in wild type epidermis were not detected in Ikaros C−/− mice. No DETC were found in the epidermis of 8 mutant mice analyzed even when probed for Thy-1 antigen expression. In contrast, vaginal epithelial $_\gamma\delta$ T cells were present in a normal distribution and density in 8 out of 8 mice examined. Whereas thymic $_\gamma\delta$ T cells were present albeit in decreased numbers, no significant population of $_\gamma\delta$ T cells was detected in the spleen of the adult Ikaros C−/− mice (FIG. 12A and 12B). Intestinal intraepithelial lymphocytes (IELs) bearing $_\gamma\delta$ TCRs and expressing the CD8 $\alpha\alpha$ co-receptor were absent or significantly reduced in 6 mice analyzed (FIG. 12C). The number of CD8-$_\gamma\delta$ IELs was also drastically reduced (FIG. 12C). In sharp contrast, the number of αβ IELs was similar in wild type and C−/− mice (FIG. 12C). Epidermal and vaginal Langerhans cells identified by their class II expression were present in normal number and distribution in Ikaros C−/− mice.

The experiments described above we performed essentially as follows. Ammonium thiocyanate-separated epidermal or vaginal sheets were incubated with a 1:20 dilution of goat serum and then stained with mAb GL3 (specific for $_\gamma\delta$ TCR), followed by biotin conjugated goat-anti-hamster Ig, avidin-biotin complexes (Vectastain Peroxidase Standard ABC Kit) and developed with 3-amino-9-ethylcarbazole (Bigby et al. (1987) J Invest Dermatol 89, 495-9). Positively stained dendritic cells were identified by light microscopy. Separate sheets were stained with PE conjugated Thy-1 mAb (53-2.1), or unconjugated mAb M5/114 (specific for class II antigen) followed by FITC conjugated goat anti-rat antibody as described and evaluated by immunofluorescence microscopy. Positively stained dendritic cells were identified by epifluorescence microscopy. Hamster Ig, a PE-conjugated rat IgG$_{2a}$ and unconjugated rat IgG$_{2b}$ control antibodies were used for GL3, Thy-1 and M5/114 respectively.

To enrich thymuses or spleens for $_\gamma\delta$ T cells and NK cells, single cell suspensions were depleted by coating them with a mixture of mAbs (CD4 and CD8 for thymuses; and CD4, CD8, B220, Mac-1, Gr-1, and Terr119 for spleens) and depleting the coated cells with anti-rat Ig coated magnetic beads (Ardavin et al. (1993) Nature 362, 761–763). Enriched thymus were stained for two color fluorescence analysis as described above.

Figure 13A:
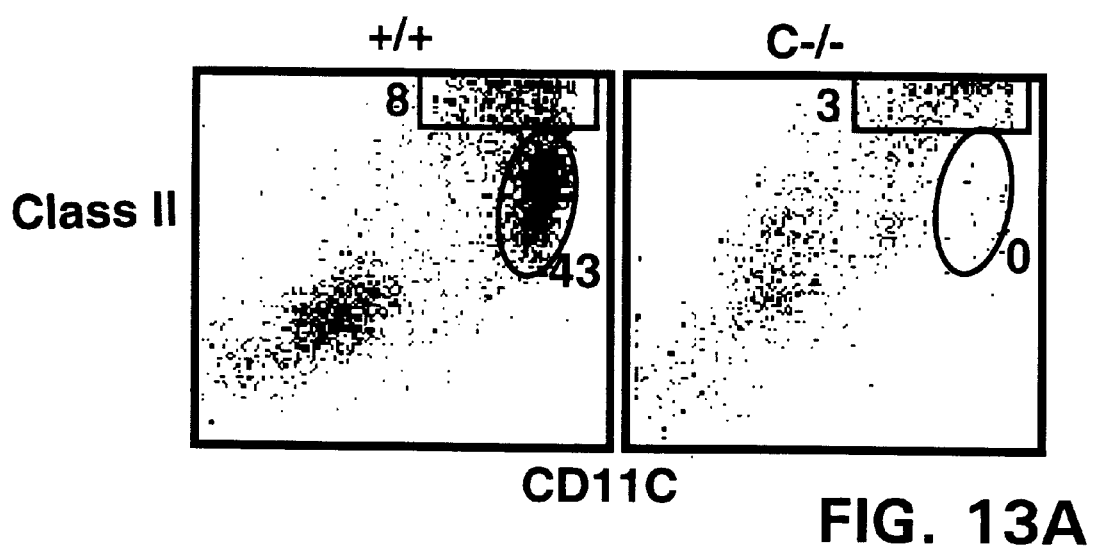
FIGS. 13A–C is a depiction that Ikaros C−/− mice lack NK cells and have a defect in the development of thymic dendritic APCs. Lineage depleted splenocytes from Ikaros C−/− and wild type mice were stained with an antibody to NK1.1 which is expressed on mature NK cells of the C57BL/6 background (A). 3–5% of Lin$^-$ splenocytes in the wild type were NK1.1.$^+$ No NK1.1$^+$ cells were detected in the Ikaros C−/− spleen. The broken line histogram indicates the isotype control whereas simple and bold line histograms show NK1.1 staining of the respective wild type and Ikaros C−/− splenocytes. NK cell function in Ikaros C−/− and wild type controls was tested by culturing splenocytes for 4 days in the presence of 500 units/ml of IL-2 (B). In wild type mice, these conditions are known to generate activated NK cells which can readily lyse Yac-1 targets. Spleen cells from wild type mice lysed chromium labeled Yac-1 over a wide range of effector to target cell ratios. In contrast, spleen cells from Ikaros C−/− mice were unable to lyse NK targets even at the highest effector to target cell ratio. Lineage depleted thymocytes from Ikaros C−/− and wild type mice were stained with antibodies to Class II and CD11c antigens expressed on mature dendritic APCs (C). CD11c$^+$/Class II$^{int-high}$ APCs were absent from the Ikaros C−/− spleen. Interestingly CD11c$^+$/Class II$^{high}$ cells were present. These cells may represent a distinct class or state of maturation of antigen presenting cells.

NK Cells and Thymic Dendritic APC are Absent or Significantly Reduced in C −/− Mice A common lymphoid progenitor (CD4$^{lo}$/c-kit+/CD44+) present in the adult thymus may give rise to thymic dendritic APCs, NK cells and to the conventional αβ and $_\gamma\delta$ T cells (Ardavin et al. (1993) Nature 362, 761–763). Thymic dendritic APCs as well as NK cells are derived from the earliest steps in the differentiation of this multipotent lymphoid progenitor. An alternative hypothesis is that these lineages arise from distinct thymic precursors which share a similar surface phenotype (Shortman, K., & Wu, L. (1996) Annu Rev Immunol 14, 29–47). The presence of thymic dendritic APCs that express Class II and CD11c antigens was examined in wild type as well as in Ikaros C−/− thymuses. After lineage depletion, thymic APCs (CD11c+/ClassII$^{int/high}$) were highly enriched (51%) in the wild type thymus (FIG. 6A). In contrast, no cells with the CD11c+/ClassII$^{int}$ and very few cells (3%) with the CD11c+/ClassII$^{high}$ surface phenotypes were detected in the lineage depleted mutant thymus (FIG. 13A).

Figure 13B:
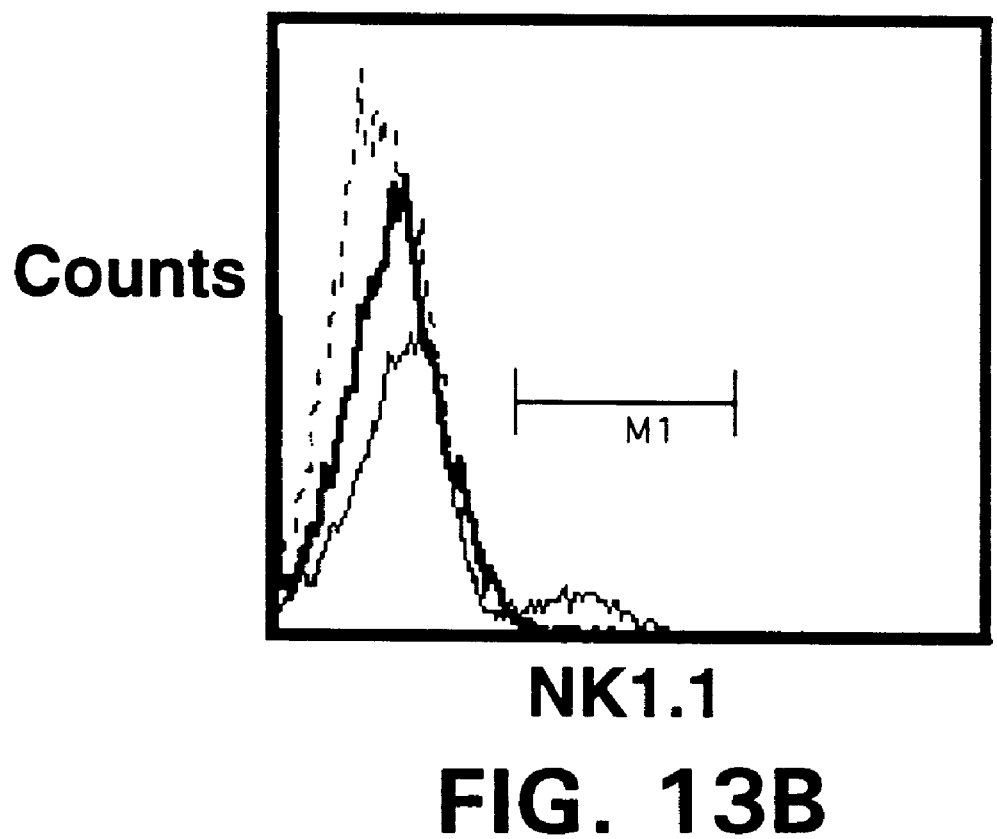
Figure 13C:
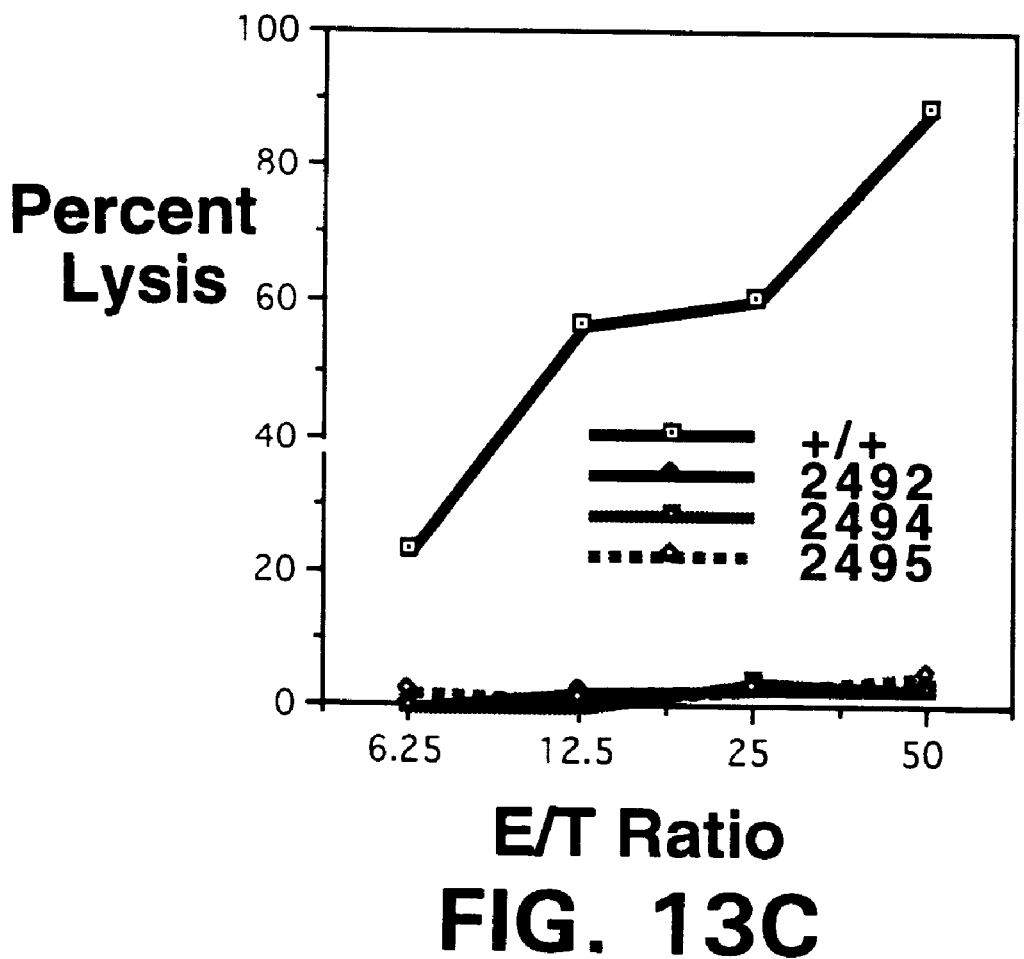

The presence of NK cells in wild type and Ikaros C−/− mice was evaluated using an antibody to the NK1.1 marker on lineage depleted splenocytes. A small population of NK1.1 cells was present among wild type splenocytes (2–5% determined on the SV129×C57BL/6 background). Cells that expressed NK1.1 were not present among Ikaros C−/− splenocytes (FIG. 13B). A functional assay was also used to conclusively address the existence of NK cells. Spleen cells from wild type control mice effectively lysed chromium labeled NK cell targets (Yac-1) over a wide range of effector to target ratios (FIG. 13C). However, spleen cells from the Ikaros C−/− mice were unable to lyse NK targets even at the highest effector to target cell ratio (FIG. 13C).

Development of thymic dendritic APCs and NK cells which derive from the earliest branch point in the T cell differentiation pathway is impaired in the absence of Ikaros activity. Ikaros C−/− mice also lack peripheral lymphatic centers. Inguinal, cervical, axial and mesenteric lymph nodes, Peyer's patches and lymphoid follicles in the gastrointestinal tract were absent. Lymph nodes which appear during late fetal life rely on dendritic APCs for their proper development. Absence of an intact dendritic APC compartment in the Ikaros C−/− mice may account for the block in the development of their peripheral lymphatic centers.

The experiments described above we performed essentially as follows. To enrich thymuses for dendritic cells, pooled minced thymuses were digested with collagenase, and treated with EDTA. Light density cells were collected by density-centrifugation and non-dendritic cell lineage cells were depleted by coating them with a mixture of mAb and depleting the coated cells with anti-rat Ig coated magnetic beads (Ardavin et al. (1993) Nature 362, 761–763). Enriched thymus cell suspensions were stained for two color fluorescence analysis as described above.

Spleen cells were stimulated for 4 days in vitro with 500 units/ml of recombinant IL-2. The ability of stimulated cells to lyse Yac-1 targets was measured in a standard 4 hour chromium release assay (Garni et al. (1990) J. Immunol. 144, 796–803).

Figure 14A:
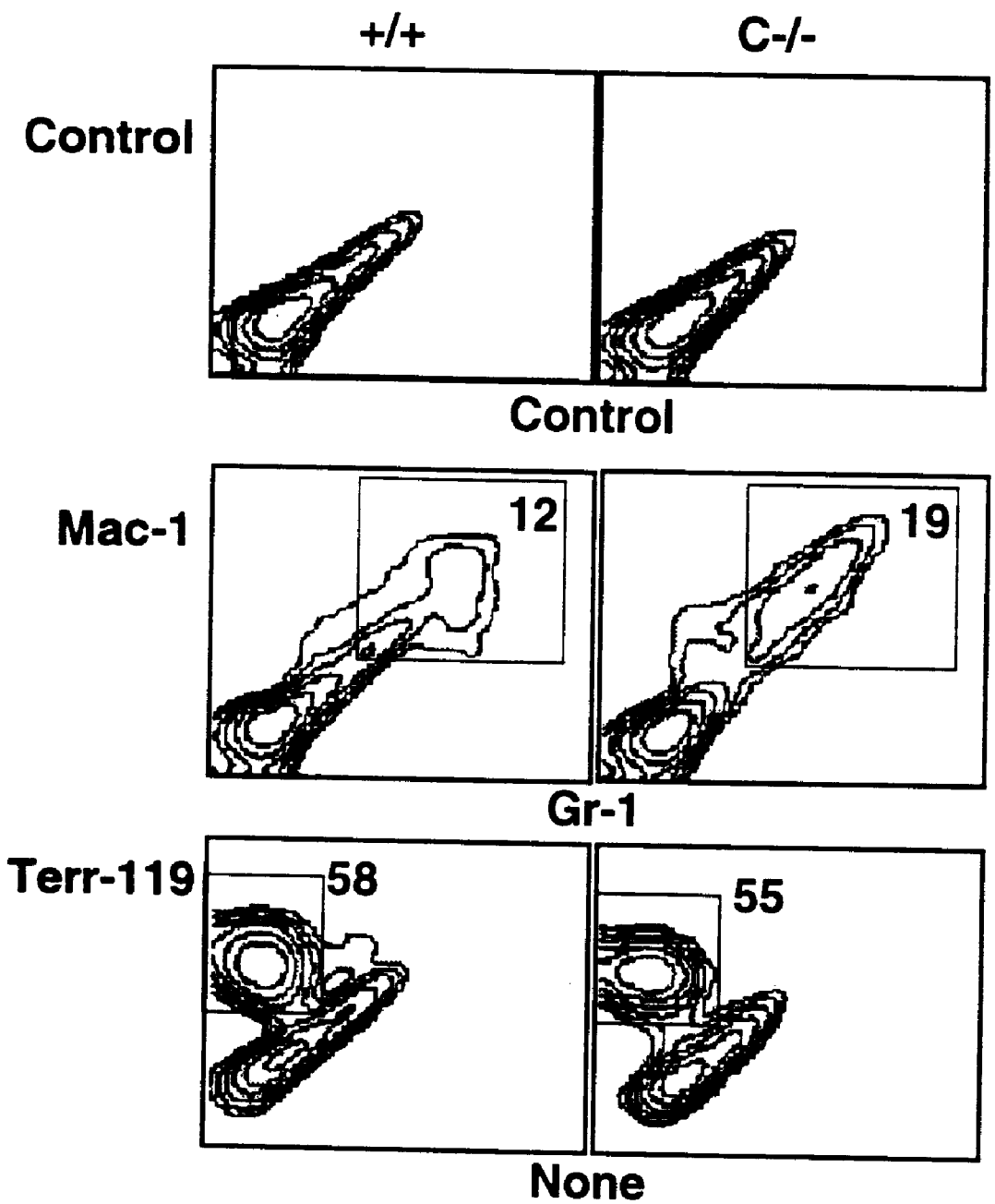
FIGS. 14A–C depicts fetal and postnatal waves of myeloid and erythroid differentiation in Ikaros C−/− mice. Cells obtained from the E-16 fetal liver (A), and from the bone marrow (B) and spleen (C) of three week old wild type and Ikaros C−/− mice were stained with anti-Mac-1$^{PE}$/anti-Gr-1$^{FITC}$, anti-TER-119$^{PE}$ and anti-TER-119$^{PE}$/anti-CD61$^{FITC}$ respectively. Positively stained populations are boxed and percentages shown. Similar percentages of granulocytes (Mac-1+/Gr-1+) cells were detected in the fetal liver of wild type and Ikaros C−/− mice. The granulocyte population was significantly decreased in the bone marrow of Ikaros mutant mice. The percentage of Mac-1$^+$/Gr-1$^-$ cells (that includes committed myeloid precursors, mature monocytes and macrophage) was significantly increased in both the spleen and bone marrow of Ikaros mutant mice. The percentages of committed erythroid precursors (TER-119$^+$) were similar in fetal and adult hemopoietic sites of Ikaros C−/− and wild type mice.
Figure 14B:
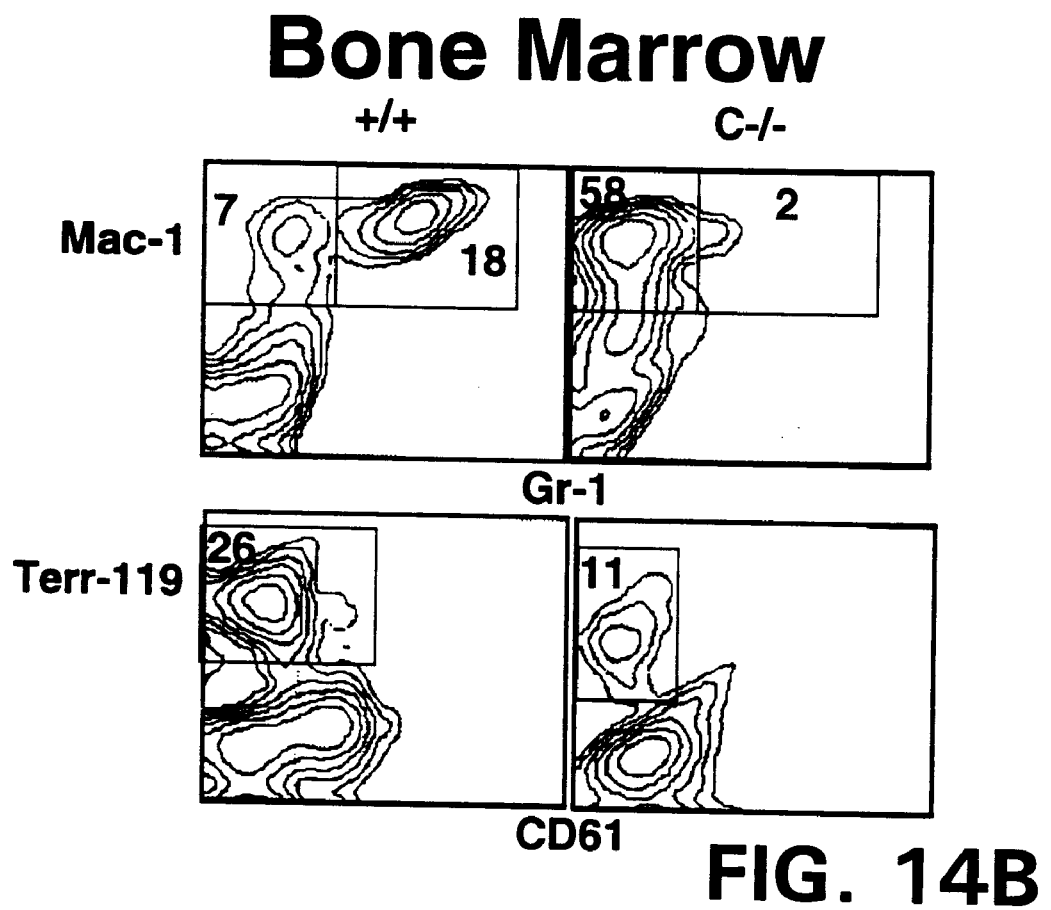

Erythropoiesis and Myeloid Differentiation are Relatively Unaffected Durine Both Fetal and Adult Development Fetal liver HSCs give rise predominantly to cells of the erythroid and myeloid lineage. Both of these cell types were present in normal numbers in the mid-late gestation liver of the Ikaros C−/− fetus (FIG. 14A). The spleen is a late fetal hemopoietic site that postnatally becomes populated with T and B lymphocytes but retains some of its hemopoietic potential throughout adult life. The major hemopoietic site in the adult is the bone marrow where erythroid and myeloid precursors are generated. In both young and adult Ikaros C−/− mice, erythroid and myeloid precursors comprise the majority of the bone marrow and spleen populations. These myeloid and erythroid cells range in absolute numbers from normal to significantly elevated (FIG. 14B). Red blood cell counts and hematocrits were within physiological range. Among myeloid cells, co-expression of Mac-1 with high levels of the Gr-1 marker identifies terminally differentiated, mature neutrophils (FIG. 14B). Whereas fetal liver granulocyte populations were similar to wild type in Ikaros C−/− mice, a lower than normal number of granulocytes was detected in the bone marrow of young mutant homozygotes (FIGS. 14A and 14B). This impairment in bone marrow derived Mac-1$^+$/Gr-1$^+$ cells may be the effect of the Ikaros mutation in postnatal myeloid progenitors. Alternatively, it may be due to inappropriate cell interactions in the absence of B and mature T lymphocytes in the bone marrow of these young mutant animals.

Elucidating the molecular mechanisms that control cell fate decisions at the level of a hemopoietic stem cell is central to our understanding of how the blood and immune systems develop. The regulatory gene Ikaros expressed from the pluripotent stem cell compartment through various multipotent progenitors to mature lymphocytes was identified as a central regulator of lymphocyte specification (Georgopoulos et al. (1994) Cell 79, 143–156). An N-terminal deletion in the DNA binding domain of the Ikaros gene (DN−/−) resulted in an early and complete block in the development of all lymphocytes in the fetal and adult hemopoietic system. In mice heterozygous for this N-terminal mutation, proteins generated by the mutant Ikaros locus display a dominant interference effect towards wild type Ikaros isoforms, causing the rapid development of leukemias and lymphomas (Winandy et al. Cell 83, 289-99, 1995). The severe lymphoid defects detected in mice homozygous and heterozygous for this N-terminal deletion may be due to the combined lack of Ikaros activity as well as a dominant interference from its mutant proteins towards other factors with which Ikaros interacts to specify lymphoid identity and maintain homeostasis.

To examine this possibility and determine the direct effect of the loss of Ikaros activity in the hemo-lymphoid system its last translated exon was deleted. This exon includes a zinc finger dimerization and activation domains shared by all of the Ikaros proteins. Without these domains the Ikaros proteins are functionally inactive and do not display dominant negative effects on transcription. Moreover, these truncated forms are unstable and rapidly degraded in cells in which they are produced. Therefore, mice homozygous for this C-terminal Ikaros deletion are virtually null for any Ikaros protein. In contrast to the DN−/− mice which lack all fetal and adult lymphoid lineages, Ikaros C−/− mice display selective defects in their fetal and adult lymphoid compartments. These results provide direct evidence that Ikaros proteins are an absolute requirement for the development or differentiation of fetal HSCs into lymphoid lineages but their action is partially redundant for the development or differentiation of adult HSCs into some lymphoid lineages.

Fetal and postnatal B cell development were completely blocked in Ikaros C−/− mice. B cell precursors normally detected in the mid-gestation fetal liver were absent from the Ikaros C−/− hemopoietic organs (Hardy et al. (1991) J. Exp. Med. 173, 1213–1225). In spite of their ability to give rise to T cell progenitors, postnatal HSCs in Ikaros C−/− mutant mice were unable to generate even the earliest pro-B cells, normally found in the bone marrow of the wild type animals.

Therefore, B lymphocyte differentiation is completely blocked at the level of both fetal and postnatal HSCs.

During fetal development, HSC and their immediate progeny, originating from the aorta gonad mesonephros areas or from the liver primordium, colonize the thymus (Dieterlen-Lievre et al. (1994) Annals of the New York Academy of Sciences 718, 140-6; Dzierzak et al. (1995) Trends in Genetics 11, 359-66). The expansion of lymphoid precursors in the normal fetal thymus occurs in waves. The first wave enters the fetal thymus by day 13 and gives rise to two successive populations of fetal thymocytes (Havran et al. (1988) Nature 335, 443–445). The first population expresses the $V_\gamma 3$ TCR and comprise the majority of TCR expressing thymocytes between days 14 and 16. These cells migrate to the skin and constitute the $V_\gamma 3$ DETC compartment. The second population expresses the $V_\gamma 4$ TCR and comprise the majority of TCR expressing thymocytes between day 16 to 19 of gestation (Havran et al. (1988) Nature 335, 443–445). They migrate to the mucosal epithelia of the female reproductive tract and tongue. No thymocytes expressing either $V_\gamma 3$ or $V_\gamma 4$ TCR are evident in the fetal thymus after day 19 and they are virtually absent in the adult organ (Havran et al. (1988) Nature 335, 443–445). The second wave of lymphoid precursors enters the fetal thymus after day 15. They give rise to the majority of TCR expressing thymocytes in the late fetal and early postnatal thymus. The late fetal and postnatal waves of thymic progenitors give rise to $_\gamma\delta$ T cells that populate the spleen and lymph nodes. These $_\gamma\delta$ cells preferentially express the $V_\gamma 2$ TCR. They constitute a minute percentage (0.5–2%) of splenic and lymph node T cells (Ito et al. (1989) Proceedings of the National Academy of Sciences of the United States of America 86, 631-5). A fourth type of $_\gamma\delta$ T cells of potential extrathymic origin is generated postnatally (Lefrancois, L. (1991) Immunol Today 12. 436-8; Lefrancois et al. (1990) Cell 63, 333–340). These $_\gamma\delta$ T cells express the $V_\gamma 5$ TCR and CD8α/α co-receptor and reside only in the intestinal epithelium (Guy et al. (1991) J Exp Med 173, 471-81).

Figure 15:
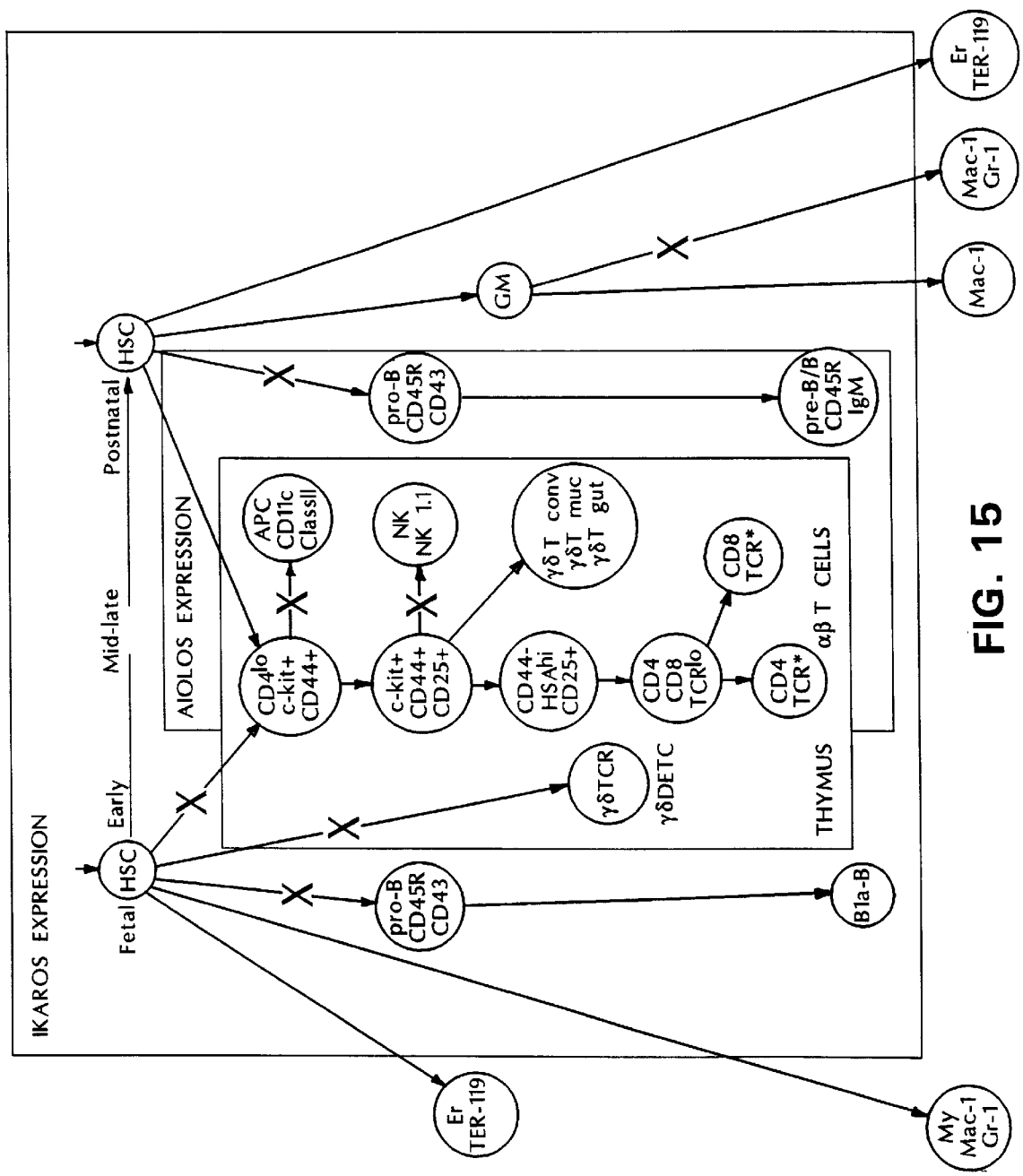
FIG. 15 is a schematic diagram depicting lymphocyte development. Lymphocyte development without Ikaros: essentials and redundancies in this regulatory network define a distinct molecular makeup for fetal and adult hemolymphoid progenitors. HSC=hemopoietic stem cells, GM=granulocyte-monocyte progenitors, Er=erythroid, TCR=T cell receptor, NK=Natural Killer, APC=antigen presenting cell. The differentiation antigens used to study development along various hemo-lymphoid lineages in Ikaros C−/− mice are shown. Arrows demarcate the proposed differentiation pathways. X on the arrows indicates a block in differentiation. Vertical arrows pointing to HSCs indicate a potentially distinct origin of fetal versus adult HSCs. The broken arrow between fetal and adult HSCs depicts a putative relationship. The thick arrow pointing towards CD4 T cells indicates their overproduction in the Ikaros C−/− thymus. The dashed arrow in the T cell pathway marks the partial block in the differentiation of $_\gamma\delta$ T cells. The asterisk on CD4 and CD8 T cells marks their hyperproliferative nature. The white area includes fetal and adult thymic development. Gray and black areas represent Ikaros and Aiolos expressions in the fetal and adult hemo-lymphoid systems.

The first and second waves of fetal thymocyte immigration or expansion do not occur in Ikaros C−/− mice (FIG. 15). Therefore, the thymus of these mutant mice is devoid of a lymphoid compartment throughout fetal life and for the first few days after birth. In contrast to the early and complete block in lymphoid differentiation manifested in the fetus, thymocyte precursors are detected in the Ikaros C−/− thymus a few days after birth. These thymocyte populations reach nearly normal numbers in the one month old Ikaros mutants.

Postnatal αβ T cell precursors give rise to CD4$^+$8$^-$ and CD4$^-$8$^+$ αβ T cells in Ikaros C−/− mice. However, a 2–3 fold increase in the proportion of CD4$^+$/αβ T cells was detected from the onset of T cell differentiation in the mutant thymus (FIG. 15). This increase in CD4$^+$ T cells was accompanied by a concomitant decrease in double positive thymocytes with no apparent change in CD8 single positive thymocytes. In the absence of a functional Ikaros gene, an increase in CD4 thymocytes may be due to deregulation of CD4 lineage commitment. Alternatively it may result from an inappropriate accumulation of CD4 T cells during their selection. Ligation of the TCR complex on the surface of immature thymocytes triggers the protein kinase C pathway and expression of the CD69 antigen (Testi et al. (1989) Journal of Immunology 143, 1123-8). Transitional stage intermediates and many of the mature single positive thymocytes express the CD69 activation marker on their surface (Bendelac et al. J Exp Med 175, 731-742, 1992; Swat et al. Eur J Immunol 23, 739–746, 1993). Among Ikaros C−/− mutant thymocytes, the great majority of CD4 single positives and their transitional stage intermediates (CD4$^+$CD8$^{lo/int}$) did not express CD69 suggesting inappropriate selection in this αβ T lineage. This defect was not observed for CD8$^+$ T cells which expressed lower levels of CD69 even in the wild type. Therefore, lack of Ikaros proteins in αβ T cell precursors does not block their ability to give rise to the CD4 and CD8 αβ T lineages but potentially interferes with selection along the CD4 T cell pathway (FIG. 15).

Ikaros C−/− thymocyte populations proliferated significantly more than their wild type counterparts when triggered through their TCR (Table 2). Deregulated expansion of double and single positive thymocytes with the same TCR specificity may occur after engagement of the pre-TCR or TCR complexes. Oligoclonal and monoclonal thymocyte populations predominate in the thymuses of older Ikaros C−/− mice. Augmented T cell proliferative responses followed by the rapid development of leukemias and lymphomas were also observed in mice heterozygous for the Ikaros DNA binding mutation (Winandy et al. Cell 83, 289-99, 1995). In these mutant mice, dominant negative Ikaros proteins can interfere with the activity of wild type isoforms but also with other factors resulting in deregulation of T cell homeostasis. Comparison of the hyperproliferative phenotype of the two distinct Ikaros mutations (DN−/− and C−/−) suggest that a profound decrease or lack of Ikaros activity leads to T cell hyperproliferation, aberrant expansion of thymic clones and T cell neoplasia (FIG. 15). These results indisputably establish Ikaros as a tumor suppressor gene essential in both differentiating and mature T cells. In the absence of Ikaros, thymocytes and mature T cells undergo aberrant expansion possibly after engagement of their TCR complex. The transition of such proliferating mutant T cells to a neoplastic state is either concomitant or rapidly follows TCR signaling.

Some $_\gamma\delta$ T cells were found in the early Ikaros C−/− thymus, indicating that this branch point in T cell differentiation is partly intact (FIG. 15). Since V$_\gamma$3 T cells that give rise to DETC arise only in the context of fetal progenitors and a fetal thymic microenvironment (Ikuta et al. (1991). J. Exp. Med. 174, 1279–1282; Ikuta et al. (1990) Cell 62, 863–874), no DETC were found in the epidermis of mutant mice (FIG. 15). Thymocyte progenitors that mature in the Ikaros C−/− thymus postnatally do not give rise to DETC. In sharp contrast, vaginal epithelial $_\gamma\delta$ T cells (V$_\gamma$4) which are proposed to be predominantly derived from the early wave of fetal T cell progenitors were present in a normal distribution and density in the Ikaros mutant mice (FIG. 15). Therefore, V$_\gamma$4 T cells can be readily generated from postnatal T cell progenitors (Ikuta et al. (1991). J. Exp. Med. 174, 1279–1282). Although $_\gamma\delta$ T cells were detected in the thymus albeit in reduced numbers, no significant $_\gamma\delta$ T cell population was seen in the spleen of the adult Ikaros C−/− mice. In addition, IELs bearing $_\gamma\delta$ TCRs and expressing the CD8 αα co-receptor were absent or significantly reduced. The number of CD8-$_\gamma\delta$ IELs was also drastically reduced. These studies support the existence of distinct migration and expansion requirements for distinct types of $_\gamma\delta$ T cells.

In the wild type thymus, the earliest T cell progenitor (CD44$^+$/c-kit$^+$/CD4$^{lo/-}$) gives rise to NK cells and thymic dendritic APCs (Wu et al. (1995) Eur J Immunol 25, 418–425). NK cells and thymic dendritic APCs were absent or significantly reduced in Ikaros C−/− mice, suggesting that the early branch points into these two pathways were blocked in the absence of Ikaros (FIG. 15).

Figure 14C:
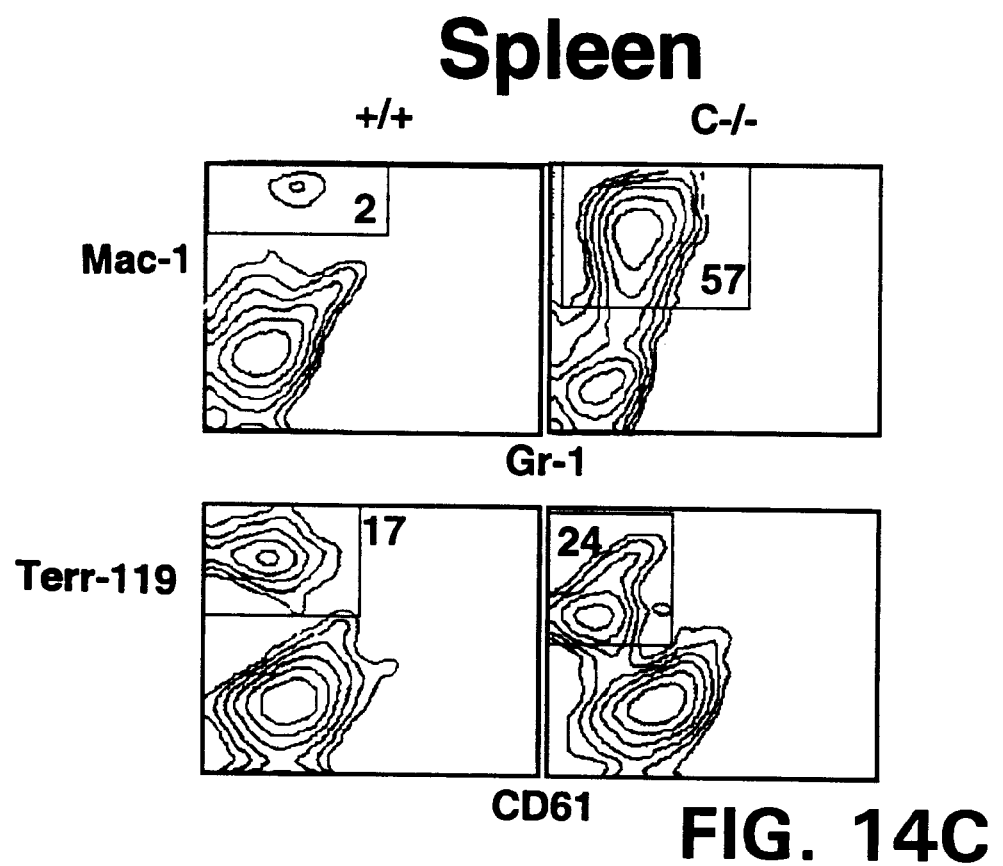

In spite of the multiple defects observed in the lymphoid compartment of the Ikaros mutant mice, both fetal and postnatal HSCs differentiate along the erythroid and myeloid pathways and give rise to some of their mature progeny. The percentage of granulocytes was lower in Ikaros C−/− bone marrow than in the wild type. This result suggests that the Ikaros mutation may have an effect on later stages of the myeloid pathway. This effect may reflect a block in granulocyte maturation caused by lack of growth factors normally provided by an intact microenvironment. Absence of lymphocytes in the bone marrow may be responsible for this myeloid lineage maturation defect in young homozygotes. Alternatively, lack of Ikaros activity in postnatal myeloid progenitors may directly affect granulocyte differentiation. The lack of mature granulocytes in Ikaros C−/− bone marrow does not appear to be caused by their early release. Mature granulocytes were not found in the spleen or peripheral blood of Ikaros C−/− mice (FIG. 14C).

Differences in the development of the postnatal T cell lineage observed between the two Ikaros mutations strongly suggest that Ikaros works in concert with another factor to determine at least T cell differentiation in the adult hemopoietic system. Aiolos, a gene with strong structural and functional similarities to Ikaros has been recently described. In contrast to Ikaros, Aiolos is not expressed in embryonic and fetal hemopoietic sites or in the mid-gestation thymus during the first wave of T cell differentiation (FIG. 15). Aiolos expression is first detected in the late gestation thymus and persists at high levels in the adult organ. Aiolos is also expressed in B lymphocytes and their immediate precursors. Within bone marrow derived multipotent progenitors, Aiolos expression is restricted to the more lymphoid committed stem cell compartment (Sca-1$^+$/c-kit$^+$/Sca-2$^+$). Aiolos expression is strongly upregulated when these progenitors become definitive T and B lymphocyte precursors. The Aiolos protein dimerizes with Ikaros isoforms through a highly conserved C-terminal zinc finger domain and modulates their activity in transcription.

That Aiolos is expressed in the bone marrow populations of the dominant negative Ikaros N−/− mice, suggests the presence of an early hemo-lymphoid progenitor in these animals. Lack of a functional Ikaros as well as Aiolos interference exerted by Ikaros mutant forms in hemo-lymphoid progenitors may account for the complete and early block in the development of all fetal and adult lymphoid lineages. In contrast, postnatal C−/− hemo-lymphoid progenitors which express Aiolos but have no functional Ikaros or any of its interfering forms can differentiate into the T cell pathway. However, Aiolos activity in these progenitor populations is not sufficient to allow proper T cell differentiation or rescue development into the B cell and NK lineages. Functional differences between Ikaros and Aiolos homo- and heterodimers may account for this partial rescue in T cell differentiation in adult Ikaros C−/− mice.

The lymphoid defects manifested in Ikaros null mice provide a unique insight into the complex regulatory network that controls lymphocyte differentiation and homeostasis in the fetal and adult hemopoietic system. The Ikaros gene is essential for the specification of all lymphoid lineages during fetal hemopoiesis but is partially redundant in adult lymphocytes. In its absence, other factors (e.g., Aiolos) which normally work in concert with Ikaros may substitute for some but not all of its functions in lymphoid lineage specification, differentiation and homeostasis.

All of the above-cited references and publications are hereby incorporated by reference.

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

GTAGGCACCT GTGGGAAGA AACT                                              24

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

TGAGAGCTGT CTCCTACTAT CGATT                                            25

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATTGTGGGGA CTGGGGGGGC                                                  20

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CACTACCTCT GGAGCACAGC AGAA                                             24

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
AGTAATGTTA AAGTAGAGAC TCAG                                              24

(2) INFORMATION FOR SEQ ID NO:6:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:6:

GGTGAACGGC CTTTCCAGTG C                                                 21

(2) INFORMATION FOR SEQ ID NO:7:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:7:

TCTGAGGCAT AGAGCTCTTA C                                                 21

(2) INFORMATION FOR SEQ ID NO:8:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:8:

CATAGGGCAT GTCTGACAGG CACT                                              24

(2) INFORMATION FOR SEQ ID NO:9:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:9:

GGGCCTTTGG GGACATCGAA GGTC                                              24

(2) INFORMATION FOR SEQ ID NO:10:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:10:

CATAGGGCAT GTCTGACAGG CACTTGT                                           27
```

(2) INFORMATION FOR SEQ ID NO:11:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:11:

CCAGCCTCTG AGCCCAGAAA GCGA                                              24

(2) INFORMATION FOR SEQ ID NO:12:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:12:

GTAGGCACCT GTGGGAAGA AACT                                               24

(2) INFORMATION FOR SEQ ID NO:13:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:13:

TGAGAGCTGT CTCCTACTAT CGATT                                             25

(2) INFORMATION FOR SEQ ID NO:14:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:14:

ATTGTGGGGA CTGGGGGGGC                                                   20

Other embodiments are within the following claims.

What is claimed is:

1. A method of making a proliferation-regulated cell comprising:
   providing a nonhuman mammal into which has been exogenously introduced an Ikaros-deregulated cell, said cell having a reduced concentration or activity of non-proliferative Ikaros dimers;
   allowing said Ikaros-deregulated cell to divide and give rise to a proliferation-deregulated cell, said proliferation-deregulated cell having a reduced concentration or activity of a non-proliferative dimer, which dimer includes any of isoform lK-1, IK-2, or IK-3; and
   isolating a proliferation-deregulated cell from the nonhuman mammal provided that if the exogenously introduced Ikaros-deregulated cell is other than autologous or syngeneric, the nonhuman mammal is immunocompromised.

2. The method of claim 1 wherein said proliferation deregulated cell expresses an Ikaros isoform which lacks one or more functional F1, F2, F3, or F4 zinc finger regions.

3. The method of claim 1 wherein said proliferation deregulated cell has a mutation which decreases the production of Ikaros isoform IK-1, IK-2, or IK-3.

4. The method of claim 1 wherein said proliferation-deregulated cell is homozygous or heterozygous for an Ikaros transgene, and is from a transgenic mouse which exhibits a deregulated Ikaros phenotype.

5. The method of claim 1, wherein the Ikaros-deregulated cell carries a mutation which inactivates one or both of the C terminal Zinc finger domains of an Ikaros gene and said mutation results in a reduced concentration or activity of at least one non-proliferative Ikaros dimer.

6. The method of claim 1, wherein the Ikaros-deregulated cell carries a mutation in the DNA binding region of an Ikaros gene and said mutation results in a reduced concentration or activity of at least one non-proliferative Ikaros dimer.

7. The method of claim 1, wherein said Ikaros-deregulated cell is a hematopoietic cell.

8. The method of claim 1, wherein said proliferation-deregulated cell is a T lymphocyte.

9. The method of claim 1, wherein said nonhuman mammal is a rodent.

10. The method of claim 1, wherein said nonhuman mammal is a mouse.

11. The method of claim 1, wherein said Ikaros-deregulated cell is a human cell.

12. The method of claim 1, wherein said Ikaros-deregulated cell is a nonhuman cell.

13. The method of claim 1, wherein said Ikaros-deregulated cell is a mouse cell.

14. A method of making a clonal population of cells comprising:
providing a nonhuman mammal into which has been exogenously introduced an Ikaros-deregulated cell, said cell having a reduced concentration or activity of non-proliferative Ikaros dimers; and
isolating one or more proliferation deregulated cells from the mammal, said cell or cells having a reduced concentration or activity of a non-proliferative dimer which dimer includes any of isoform IK-1, IK-2, or IK-3. provided that if one cell is isolated, the cell is allowed to proliferate into a clonal population of proliferation deregulated cells,
provided that if the exogenously introduced Ikaros-deregulated cell is other than autologous or syngeneic, the nonhuman mammal is immunocompromised.

15. The method of claim 14, wherein said proliferation deregulated cell or cells express an Ikaros isoform which lacks one or more functional F1, F2, F3, or F4 zinc finger regions.

16. The method of claim 14, wherein said proliferation deregulated cell or cells have a mutation which decreases the production of Ikaros isoform IK-1, IK-2, or IK-3.

17. The method of claim 14, wherein the proliferation-deregulated cell or cells are homozygous or heterozygous for an Ikaros transgene, and is from a transgenic mouse which exhibits a deregulated Ikaros phenotype.

18. The method of claim 14, wherein the Ikaros-deregulated cell carries a mutation which inactivates one or both of the C terminal Zinc finger domains of an Ikaros gene and said mutation results in a reduced concentration or activity of at least one non-proliferative Ikaros dimer.

19. The method of claim 14, wherein the Ikaros-deregulated cell carries a mutation in the DNA binding region of an Ikaros gene and said mutation results in a reduced concentration or activity of a least one non-proliferative Ikaros dimer.

20. The method of claim 14, wherein said Ikaros-deregulated cell is a hematopoietic cell.

21. The method of claim 14, wherein said clonal population is a clonal population of T lymphocytes.

22. The method of claim 14, wherein said mammal is a rodent.

23. The method of claim 14, wherein said mammal is a mouse.

24. The method of claim 14, wherein said Ikaros-deregulated cell is a human cell.

25. The method of claim 14, wherein said Ikaros-deregulated cell is a nonhuman cell.

26. The method of claim 14, wherein said Ikaros-deregulated cell is a mouse cell.

27. A method of making a T lymphocyte, or a substantially homogenous population of T lymphocytes, which recognize a selected antigen comprising:
providing a nonhuman mammal into which has been exogenously introduced an Ikaros-deregulated cell from a mammal, said cell having a reduced concentration or activity of non-proliferative Ikaros dimers said cell being heterozygous for an Ikaros mutation;
wherein one or both of the nonhuman mammal, or the mammal, is immunized with an antigen;
allowing said Ikaros-deregulated cell to divide and give rise to a proliferation-deregulated T lympocyte which specifically recognizes said antigen and wherein said proliferation-deregulated T lymphocyte has a reduced concentration or activity of a non-proliferative dimer which dimer includes any of isoform IK-1, IK-2,or IK-3;
isolating one or more proliferation-deregulated T lymphocytes from the nonhuman mammal,
provided that if the exogenously introduced Ikaros-deregulated cell is other than autologous or syngeniec, the nonhuman mammal is immunocompromised.

28. The method of claim 27, wherein said nonhuman mammal is immunized with said antigen.

29. The method of claim 27, wherein the mammal which donates the Ikaros-deregulated cell is immunized with an antigen.

30. The method of claim 27, wherein the antigen is an alloantigen.

31. The method of claim 27, wherein the antigen is xenoantigen.

32. The method of claim 27, wherein the antigen is an autoantigen.

33. The method of claim 27, wherein the antigen is an antigen which gives rise to an anti-idiotypic lymphocyte.

34. The method of claim 27, wherein said proliferation deregulated T lymphocyte expresses an Ikaros isoform which lacks one or more functional F1, F2, F3, or F4 zinc finger regions.

35. The method of claim 27, wherein said proliferation deregulated T-lymphocyte cell has a mutation which decreases the production of Ikaros isoform IK-1, IK-2, or IK-3.

36. The method of claim 27, wherein the proliferation-deregulated T-lymphocyte cell is homozygous or heterozygous for an Ikaros transgene, and is from a transgenic mouse which exhibits a deregulated Ikaros phenotype.

37. The method of claim 27, wherein the Ikaros-deregulated cell carries a mutation which inactivates one or both of the C terminal Zinc finger domains of an Ikaros gene and said mutation results in a reduced concentration or activity of at least one non-proliferative Ikaros dimer.

38. The method of claim 27, wherein the Ikaros-deregulated cell carries a mutation in the DNA binding region of an Ikaros gene and said mutation results in a reduced concentration or activity of at least one non-proliferative Ikaros dimer.

39. The method of claim 27, wherein said Ikaros-deregulated cell is a hematopoietic cell.

40. The method of claim 14, wherein said clonal population is a clonal population of T lymphocytes.

41. The method of claim 27, wherein said nonhuman mammal is a rodent.

42. The method of claim 27, wherein said nonhuman mammal is a mouse.

43. The method of claim 27, wherein said Ikaros-deregulated cell is a human cell.

44. The method of claim 27, wherein said Ikaros-deregulated cell is a nonhuman cell.

45. The method of claim 27, wherein said Ikaros-deregulated cell is a mouse cell.

46. A method of culturing a proliferation- or Ikaros-deregulated cell, comprising:

providing a nonhuman mammal;

providing an Ikaros-deregulated cell from a mammal other than said nonhuman mammal;

introducing into said nonhuman mammal said Ikaros-deregulated cell, said cell having a reduced concentration or activity of a non-proliferative Ikaros dimer which dimer includes any of isoform TK-1, K-2, or IK-3; and culturing said Ikaros-deregulated cell which can divide and give rise to a proliferation-deregulated cell in said nonhuman mammal provided that if the introduced cell is other than syngeneic, the nonhuman mammal is immunocompromised.

47. The method of claim 46, wherein said proliferation deregulated cell expresses an Ikaros isoform which lacks one or more functional F1, F2, F3, or F4 zinc finger regions.

48. The method of claim 46, wherein said proliferation- or Ikaors- deregulated cell has a mutation which decreases the production of Ikaros isoform IK-1, IK-2, or IK-3.

49. The method of claim 46, wherein the proliferation- or Ikaors-deregulated cell is homozygous or heterozygous for an Ikaros transgene, and is from a transgenic mouse which exhibits a deregulated Ikaros phenotype.

50. The method of claim 46, wherein the proliferation- or Ikaros-deregulated cell carries a mutation which inactivates one or both of the C terminal Zinc finger domains of an Ikaros gene and said mutation results in a reduced concentration or activity of non-proliferative Ikaros dimers.

51. The method of claim 46, wherein the proliferation- or Ikaros-deregulated cell carries a mutation in the DNA binding region of an Ikaros gene and said mutation results in a reduced concentration or activity of at least one non-proliferative Ikaros dimer.

52. The method of claim 46, wherein said Ikaros-deregulated cell is a hematopoietic cell.

53. The method of claim 46, wherein said proliferation-deregulated cell is a T-lymphocyte.

54. The method of claim 46, wherein said nonhuman mammal is a rodent.

55. The method of claim 46, wherein said nonhuman mammal is a mouse.

56. The method of claim 46, wherein said said proliferation- or Ikaros-deregulated cell is a human cell.

57. The method of claim 46, wherein said said proliferation- or Ikaros-deregulated cell is a nonhuman cell.

58. The method of claim 46, wherein said said proliferation- or Ikaros-deregulated cell is a mouse cell.

59. A method of making a proliferation-deregulated cell comprising:

providing a transgenic mouse whose somatic and germ cells comprise a transgene which reduces the concentration or activity of a non-proliferative dimer which dimer includes any of isoform IK-1, IK-2, or K-3 and wherein said transgene results in the production of an Ikaros deregulated somatic cell having a reduced concentration or activity of a non-proliferative dimer which dimer includes any of isoform IK-1, K-2, or IK-3;

allowing said Ikaros-deregulated somatic cell to divide in said transgenic mouse and give rise to a proliferation-deregulated cell; and isolating a proliferation-deregulated cell from the transgenic mouse.

60. The method of claim 59, wherein said proliferation deregulated cell expresses an Ikaros isoform which lacks one or more functional F1, F2, F3, or F4 zinc finger regions and the expression of said isoform results in a reduced concentration or activity of at least one non-proliferative Ikaros dimer.

61. The method of claim 59, wherein said proliferation deregulated cell has a transgenic mutation which decreases the production of Ikaros isoform IK-1, IK-2, or IK-3 and the mutation results in a reduced concentration or activity of at least one non-proliferative Ikaros dimer.

62. The method of claim 59, wherein the proliferation-deregulated cell is homozygous or heterozygous for an Ikaros transgene and wherein the expression of said transgene results in a reduced concentration or activity of at least one non-proliferative Ikaros dimer.

63. The method of claim 59, wherein the proliferation-deregulated cell carries a mutation which inactivates one or both of the C terminal Zinc finger domains of an Ikaros gene and said mutation results in a reduced concentration or activity of at least one non-proliferative Ikaros dimer.

64. The method of claim 59, wherein the proliferation deregulated cell carries a mutation in the DNA binding region of an Ikaros gene and said mutation results in a reduced concentration or activity of at least one non-proliferative Ikaros dimer.

65. The method of claim 59, wherein said Ikaros-deregulated cell is a hematopoietic cell.

66. The method of claim 59, wherein said proliferation-deregulated cell is a T lymphocyte.

67. A method of making a clonal population of cells comprising: providing a transgenic mouse whose somatic and germ cells comprise a transgene which reduces the concentration or activity of a non-proliferative dimer which dimer includes any of isoform IK-1, IK-2, or TK-3 and wherein said transgene results in the production of an Ikaros deregulated somatic cell having a reduced concentration or activity of a non-proliferative dimer which dimer includes any of isoform IK-1, IK-2, or IK-3;

allowing said Ikaros-deregulated somatic cell to divide in said transgenic mouse and give rise to a proliferation-deregulated cell; and isolating one or more cells from the transgenic mouse, said cell or cells having a reduced concentration or activity of a non-proliferative dimer which dimer includes any of isoform IK-1, IK-2, or T-3, provided that if one cell is isolated, the cell is allowed to proliferate into a clonal population of cells.

68. The method of claim 67, wherein said proliferation deregulated cell expresses an Ikaros isoform which lacks one or more functional F1, F2, F3, or F4 zinc finger regions and the expression of said isoform results in a reduced concentration or activity of at least one non-proliferative Ikaros dimer.

69. The method of claim 67, wherein said proliferation deregulated cell has a mutation which decreases the production of Ikaros isoform IK-1, IK-2, or IK-3 and results in a reduced concentration or activity of at least one non-proliferative Ikaros dimer.

70. The method of claim 67, wherein the proliferation-deregulated cell is homozygous or heterozygous for an Ikaros transgene and wherein the expression of said transgene results in a reduced concentration or activity of at least one non-proliferative Ikaros dimer.

71. The method of claim 67, wherein the proliferation deregulated cell carries a mutation which inactivates one or both of the C terminal Zinc finger domains of an Ikaros gene and said mutation results in a reduced concentration or activity of at least one non-proliferative Ikaros dimer.

72. The method of claim 67, wherein the proliferation deregulated cell carries a mutation in the DNA binding region of an Ikaros gene and said mutation results in a reduced concentration or activity of at least one non-proliferative Ikaros dimer.

73. The method of claim 67, wherein said Ikaros-deregulated cell is a hematopoietic cell.

74. The method of claim 67, wherein said clonal population is a clonal population of T lymphocytes.

75. A method of making a T lymphocyte, or a substantially homogenous population of T lymphocytes, which recognize a selected antigen comprising:

providing a transgenic mouse whose somatic and germ cells comprise a transgene which reduces the concentration or activity of a non-proliferative dimer which dimer includes any of isoform IK-1, IK-2, or IK-3, and wherein said transgene results in the production of an Ikaros deregulated somatic cell having a reduced concentration or activity of a non-proliferative dimer which dimer includes any of isoform IK-1, IK-2, IK-3;

allowing said Ikaros-deregulated somatic cell to divide in said transgenic mouse and give rise to a proliferation-deregulated cell and immunizing said mouse with an antigen; and isolating one or more T lymphocytes which specifically recognizes said antigen from the mouse, said one or more T lymphocyte having a reduced concentration or activity of a non-proliferative dimer which dimer includes any of isoform IK-1, IK-2, or IK-3.

76. The method of claim 75, wherein the antigen is an alloantigen.

77. The method of claim 75, wherein the antigen is xenoantigen.

78. The method of claim 75, wherein the antigen is an autoantigen.

79. The method of claim 75, wherein the antigen is an antigen which gives rise to an anti-idiotypic lymphocyte.

80. The method of claim 75, wherein said proliferation deregulated cell expresses an Ikaros isoform which lacks one or more functional F1, F2, F3, or F4 zing finger regions and the expression of said isoform results in a reduced concentration or activity of at least one non-proliferative Ikaros dimer.

81. The method of claim 75, wherein said proliferation deregulated cell has a mutation which decreases the production of Ikaros isoform IK-1, IK-2, or IK-3 and results in a reduced concentration or activity of at least one non-proliferative Ikaros dimer.

82. The method of claim 75, wherein the proliferation-deregulated cell is homozygous or heterozygous for an Ikaros transgene and wherein the expression of said transgene results in a reduced concentration or activity of at least one non-proliferative Ikaros dimer.

83. The method of claim 75, wherein the Ikaros deregulated somatic cell carries a mutation which inactivates one or both of the C terminal Zinc finger domains of all Ikaros gene and said mutation results in a reduced concentration or activity of non-proliferative Ikaros dimers.

84. The method of claim 75, wherein the Ikaros deregulated somatic cell carries a transgenic mutation in the DNA binding region of an Ikaros gene and said mutation results in a reduced concentration or activity of non-proliferative Ikaros dimers.

85. The method of claim 75, wherein said Ikaros-deregulated somatic cell is a hematopoietic cell.

86. The method of claim 75, wherein said population of T-lymphoytes and a clonal population of T lymphocytes.

* * * * *